(12) United States Patent
Shen et al.

(10) Patent No.: US 9,290,564 B2
(45) Date of Patent: Mar. 22, 2016

(54) COMPOSITIONS AND METHODS RELATED TO THE PREVENTION AND TREATMENT OF RABIES INFECTION

(75) Inventors: Enyun Shen, Beijing (CN); Shiqi Ren, Beijing (CN)

(73) Assignee: MOUNTGATE GROUP LIMITED, Tortola (VG)

( * ) Notice: Subject to any disclaimer, the term of this patent is extended or adjusted under 35 U.S.C. 154(b) by 0 days.

(21) Appl. No.: 14/402,644

(22) PCT Filed: May 24, 2012

(86) PCT No.: PCT/CN2012/076012
§ 371 (c)(1),
(2), (4) Date: Dec. 29, 2014

(87) PCT Pub. No.: WO2013/174003
PCT Pub. Date: Nov. 28, 2013

(65) Prior Publication Data
US 2015/0110781 A1    Apr. 23, 2015

(51) Int. Cl.
*C07K 16/10* (2006.01)
*G01N 33/569* (2006.01)
*A61K 39/00* (2006.01)

(52) U.S. Cl.
CPC .......... *C07K 16/10* (2013.01); *G01N 33/56983* (2013.01); *A61K 2039/505* (2013.01); *C07K 2317/21* (2013.01); *C07K 2317/24* (2013.01); *C07K 2317/76* (2013.01); *G01N 2333/145* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. |
| 3,817,837 A | 6/1974 | Rubenstein |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,939,350 A | 2/1976 | Kronick et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,275,149 A | 6/1981 | Litman et al. |
| 4,277,437 A | 7/1981 | Maggio |
| 4,366,241 A | 12/1982 | Tom et al. |
| 4,391,904 A | 7/1983 | Litman et al. |
| 4,474,893 A | 10/1984 | Reading |
| 4,522,811 A | 6/1985 | Eppstein et al. |
| 4,714,681 A | 12/1987 | Reading |
| 4,816,397 A | 3/1989 | Boss et al. |
| 4,816,567 A | 3/1989 | Cabilly et al. |
| 4,873,316 A | 10/1989 | Meade et al. |
| 4,925,648 A | 5/1990 | Hansen et al. |
| 4,946,778 A | 8/1990 | Ladner et al. |
| 5,028,530 A | 7/1991 | Lai et al. |
| 5,225,539 A | 7/1993 | Winter |
| 5,258,498 A | 11/1993 | Huston et al. |
| 5,304,389 A | 4/1994 | Kondo et al. |
| 5,314,995 A | 5/1994 | Fell et al. |
| 5,514,548 A | 5/1996 | Krebber et al. |
| 5,573,920 A | 11/1996 | Randle |
| 5,585,089 A | 12/1996 | Queen et al. |
| 5,601,819 A | 2/1997 | Wong et al. |
| 5,648,237 A | 7/1997 | Carter |
| 5,693,761 A | 12/1997 | Queen et al. |
| 5,693,762 A | 12/1997 | Queen et al. |
| 5,723,323 A | 3/1998 | Kauffman et al. |
| 5,741,957 A | 4/1998 | Deboer et al. |
| 5,763,192 A | 6/1998 | Kauffman et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,837,500 A | 11/1998 | Ladner et al. |
| 5,849,992 A | 12/1998 | Meade et al. |
| 5,871,907 A | 2/1999 | Winter et al. |
| 5,885,793 A | 3/1999 | Griffiths et al. |
| 5,969,108 A | 10/1999 | McCafferty et al. |
| 5,976,862 A | 11/1999 | Kauffman et al. |
| 6,106,835 A | 8/2000 | Chang |
| 6,225,447 B1 | 5/2001 | Winter et al. |
| 6,291,158 B1 | 9/2001 | Winter et al. |
| 6,291,159 B1 | 9/2001 | Winter et al. |
| 6,291,160 B1 | 9/2001 | Lerner et al. |

(Continued)

FOREIGN PATENT DOCUMENTS

| | | |
|---|---|---|
| EP | 0 120 694 A0 | 10/1984 |
| EP | 0 232 262 | 8/1987 |

(Continued)

OTHER PUBLICATIONS

Kashmiri et al. (Methods. 2005; 36:25-34).*
Tamura et al. (Journal of Immunology. 2000; 164 (3):1432-1441).*
Greenspan et al (Nature Biotechnology. 17; 10:936-937 (1999).*
Rudikoff et al (PNAS. 1982; 79: 1979-1983).*
Baldari, C. et al., "A novel leader peptide which allows efficient secretion of a fragment of human interleukin 1β in *Saccharomyces cerevisiae*" EMBO J., (Jan. 1987), vol. 6, No. 1, pp. 229-234.
Byrne, G.W. et al., "Multiplex gene regulation: A two-tiered approach to transgene regulation in transgenic mice," Proc. Natl. Acad. Sci. USA, (Jul. 1989), vol. 86, pp. 5473-5477.
Camper, Sally A. et al., "Postnatal repression of the α-fetoprotein gene is enhancer independent," Genes Dev, (Apr. 1989), vol. 3, pp. 537-546.

(Continued)

*Primary Examiner* — Shanon A Foley
(74) *Attorney, Agent, or Firm* — Foley & Lardner LLP

(57) ABSTRACT

The present disclosure relates generally to anti-rabies antibodies that can bind to and neutralize rabies virus. Antibodies of the present technology are useful alone or in combination with therapies known in the art for the treatment or prevention of rabies infection.

14 Claims, 40 Drawing Sheets

(56) References Cited

U.S. PATENT DOCUMENTS

| | | | |
|---|---|---|---|
| 6,291,161 | B1 | 9/2001 | Lerner et al. |
| 6,291,650 | B1 | 9/2001 | Winter et al. |
| 6,294,353 | B1 | 9/2001 | Pack et al. |
| 6,492,107 | B1 | 12/2002 | Kauffman et al. |
| 6,492,160 | B1 | 12/2002 | Griffiths et al. |
| 6,545,142 | B1 | 4/2003 | Winter et al. |
| 6,569,641 | B1 | 5/2003 | Kauffman et al. |
| 6,680,192 | B1 | 1/2004 | Lerner et al. |
| 6,692,935 | B1 | 2/2004 | Pack et al. |
| 6,753,136 | B2 | 6/2004 | Lohning |
| 2002/0199213 | A1 | 12/2002 | Tomizuka et al. |
| 2004/0058403 | A1 | 3/2004 | Harvey et al. |
| 2015/0110781 | A1* | 4/2015 | Shen et al. .................. 424/133.1 |

FOREIGN PATENT DOCUMENTS

| | | |
|---|---|---|
| EP | 0 264 166 | 4/1988 |
| EP | 0 368 684 B1 | 5/1990 |
| EP | 0 396 387 B1 | 11/1990 |
| EP | 0 451 216 B1 | 10/1991 |
| EP | 0 464 533 | 1/1992 |
| EP | 0 585 287 | 3/1994 |
| EP | 0 589 877 | 4/1994 |
| EP | 0 605 522 B1 | 7/1994 |
| EP | 0 616 640 | 9/1994 |
| EP | 0 682 040 B1 | 11/1995 |
| EP | 0 774 511 | 5/1997 |
| EP | 0 844 306 | 5/1998 |
| EP | 1 024 191 | 8/2000 |
| WO | WO-89/12624 A1 | 12/1989 |
| WO | WO-91/00360 | 1/1991 |
| WO | WO-91/14438 A1 | 10/1991 |
| WO | WO-92/05793 A1 | 4/1992 |
| WO | WO-92/08495 A1 | 5/1992 |
| WO | WO-92/08802 A1 | 5/1992 |
| WO | WO-92/22324 A1 | 12/1992 |
| WO | WO-93/17715 A1 | 9/1993 |
| WO | WO-02/34886 | 5/2002 |
| WO | WO-2011/080765 | 7/2011 |
| WO | WO-2011/137569 | 11/2011 |
| WO | WO-2011/137570 | 11/2011 |
| WO | WO-2011/137571 | 11/2011 |

OTHER PUBLICATIONS

Chothia, Cyrus et al., "Canoical Structures for the Hypervariable Regions of Immunoglobins" J. Mol. Biol., (1987), vol. 196, pp. 901-917.

Cote, Richard J. et al., "Generation of human monoclonal antibodies reactive with cellular antigens," Proc. Natl. Acad. Sci., (Apr. 1983), vol. 80, pp. 2026-2030.

Fountoulakis, Michael et al., "Interferon γ Receptor Extracellular Domain Expressed as IgG Fusion Protein in Chinese Hamster Ovary Cells," The Journal of Biological Chemistry, (Feb. 24, 1995), vol. 270, No. 8, pp. 3958-3964.

Gentz, Reiner et al., "Bioassay for trans-activation using purified human immunodeficiency virus tat-encoded protein: Trans-activation requires mRNA synthesis," Proc. Natl. Acad. Sci. USA, (Feb. 1989), vol. 86, No. 3, pp. 821-824.

Hanes, Jozef et al., "In vitro selection and evolution of functional proteins by using ribosome display," Proc. Natl. Acad. Sci., (May 1997), vol. 94, No. 10, pp. 4937-4942.

Harding, Clifford V. et al., "Turnover of Ia-peptide complexes is facilitated in viable antigen-presenting cells: Biosynthetic turnover of Ia vs. peptide exchange," Proc. Natl. Acad. Sci. USA, (Jun. 1989), vol. 86, Issue 11, pp. 4230-4234.

Harvey, Barrett R. et al., "Anchored periplasmic expression, a versatile technology for the isolation of high-affinity antibodies for *Escherichia coli*-expressed libraries," Proc. Natl. Acad. Sci., (Jun. 22, 2004), vol. 101, No. 25, pp. 9193-9198.

Hutchison, Clyde A. et al., "Mutagenesis at a Specific Position in a DNA Sequence," The Journal of Biological Chemistry, (Sep. 25, 1978), vol. 253, No. 18, pp. 6551-6560.

International Search Report and Written Opinion of the International Searching Authority received in International Application No. PCT/CN2012/076012 mailed Mar. 7, 2013, 14 pages.

Johanson, Kyung et al., "Binding Interactions of Human Interleukin 5 with Its Receptor α Subunit: Large Scale Production, Structural, and Functional Studies of *Drosophila*-Expressed Recombinant Proteins," J. Biol. Chem., (1995), vol. 270, No. 16, pp. 9459-9471.

Kaufman, Randal J. et al., "Translational efficiency of polycistronic mRNAs and their utilization to express heterologous genes in mammalian cells," EMBO J., (1987), vol. 6, No. 1, pp. 187-195.

Kieke, Michele C. et al., "Isolation of anti-T cell receptor scFv mutants by yeast surface display," Protein Engineering, (Nov. 1997), vol. 10, No. 11, pp. 1303-1310.

Kimura, Kouichi et al., "Diversification of transcriptional modulation: Large-scale identification and characterization of putative alternative promoters of human genes," Genome Res., (Jan. 2006), vol. 16, No. 1, pp. 55-65.

Kozbor, Danuta et al., "The Production of Monoclonal antibodies from human lymphocytes,"Immunology Today, (1983), vol. 4(3), pp. 72-79.

Mattheakis, Larry C. et al. "An in vitro polysome display system for identifying ligands from very large peptide libraries" Proc. Natl. Acad. Sci. USA, (Sep. 1994), vol. 91, No. 19, pp. 9022-9026.

Merryman, Chuck et al., "A Bifunctional tRNA for In Vitro Selection," Chemistry & Biology, (Jun. 2002), vol. 9, Issue 6, pp. 741-746.

Nemoto, Naoto et al., "In vitro virus Bonding of mRNA bearing puromycin at the 3'-terminal end to the C-terminal end of its encoded protein on the ribosome in vitro," FEBS Letters, (Sep. 1997), vol. 414, Issue 2, pp. 405-408.

Peters, William P. et al., "Neutrophil migration is defective during recombinant human granulocyte-macrophage colony-stimulating factor infusion after autologous bone marrow transplantation in humans," Blood, (Oct. 1988), vol. 72, No. 4, pp. 1310-1315.

Pinkert, Carl A. et al., "An albumin enhancer located 10 kb upstream functions along with its promoter to direct efficient, liver-specific expression in transgenic mice", Genes Dev., (May 1987), vol. 1, pp. 268-276.

Rassenti, Laura Z. et al., "Lack of Allelic Exclusion in B Cell Chronic Lymphocytic Leukemia," J. Exp. Med, (Apr. 1997), vol. 185, No. 8, pp. 1435-1445.

Roberts, Richard W. et al., "RNA-peptide fusions for the in vitro selection of peptides and proteins," Proc. Natl. Acad. Sci. USA, (Nov. 1997), vol. 94, No. 23, pp. 12297-12302.

Shu, Liming et al., "Secretion of a single-gene-encoded immunoglobulin from myeloma cells" Proc. Natl. Acad. Sci. USA, The National Academy of Sciences, (Sep. 1993), vol. 90, pp. 7995-7999.

Smith, Gale E. et al., "Production of Human Beta Interferon in Insect Cells Infected with a Baculovirus Expression Vector," Mol. Cell. Biol., (1983), vol. 3, No. 12, pp. 2156-2165.

Ward, E. Sally et al., "Binding activities of a repertoire of single immunoglobulin variable domains secreted from *Escherichia coli*", Nature, (1989), vol. 341, pp. 544-546.

Windhagen, Anja et al., "Modulation of Cytokine Patterns of Human Autoreactive T Cell Clones by a Single Amino Acid Substitution of Their Peptide Ligand," Immunity, (Apr. 1995), vol. 2, pp. 373-380.

Winoto, Astar et al., "A novel, inducible and T cell-specific enhancer located at the 3' end of the T cell receptor α locus," EMBO J, (Mar. 1989), vol. 8, No. 3, pp. 729-733.

Benmansour et al., "Antigenicity of Rabies Virus Glycoprotein," Journal of Virology, vol. 65, No. 8, pp. 4198-4203, 1991.

Buschoten et al., "Characterization of a New Virus-neutralizing Epitope that Denotes a Sequential Determinant on the Rabies Virus Glycoprotein," Journal of Virology, vol. 70, pp. 291-298, 1989.

Kramer et al., "The human antibody repertoire specific for rabies virus glycoprotein as selected from immune libraries," Eur. J. Immunol., vol. 35, pp. 2131-2145, 2005.

(56) References Cited

OTHER PUBLICATIONS

Lafon et al., "Antigenic Sites on the CVS Rabies Virus Glycoprotein: Analysis with Monoclonal Antibodies," J. Gen. Virol., vol. 64, pp. 843-851, 1983.

Lafon et al., "Investigation of the Antigenic Structure of Rabies Virus Glycoprotein by Monoclonal Antibodies," Dev. Biol. Stand., vol. 57, pp. 219-225, 1984.

Office Action on Japanese application 2015-512986 mailed Jun. 29, 2015 (English translation not provided).

* cited by examiner

FIG. 3A

Binding curves of 3D11E3 to RV glycoprotein which was treated by different methods

- 1% Triton
- 1% Triton + 0.1% SDS
- 1% Triton + 0.1% SDS + 0.05% ME

X-axis: Concentration of anti-rabies mAb (ng/mL)
Y-axis: RLU

FIG. 3B

Binding curves of 3H10D3 to RV glycoprotein which was treated by different methods

- 1% Triton
- 1% Triton + 0.1% SDS
- 1% Triton + 0.1% SDS + 0.05% ME

X-axis: Concentration of anti-rabies mAb (ng/mL)
Y-axis: RLU

FIG. 3C

Binding curves of 5A1C10 to RV glycoprotein which was treated by different methods

- 1%Triton
- 1%Triton+0.1%SDS
- 1%Triton+0.1%SDS+0.05%ME

FIG. 3D

Binding curves of 6F11C1 to RV glycoprotein which was treated by different methods

- 1%Triton
- 1%Triton+0.1%SDS
- 1%Triton+0.1%SDS+0.05%ME

FIG. 3E

Binding curves of 7G11A3 to RV glycoprotein which was treated by different methods

- 1% Triton
- 1% Triton + 0.1% SDS
- 1% Triton + 0.1% SDS + 0.05% ME

X-axis: Concentration of anti-rabies mAb (ng/mL)
Y-axis: RLU

JX09-27 (badger)

ZJ-LA (badger)

FIG. 5E

Competitive binding of 3H10D3-HRP to RV glycoprotein

- 3D11E3
- 3H10D3
- 5A1C10
- 6F11C1
- 7G11A3

Concentration of RVNA (ng/ml)

FIG. 5F

Competitive binding of 3H10D3-HRP to RV glycoprotein

- 3D11E3
- 3H10D3
- 5A1C10
- 6F11C1
- 7G11A3
- Irrelevant Ab

Concentration of RVNA (ng/ml)

Binding of 7G11A3 1H5 to Rapibur®

FIG. 15C

Capture activity of 7G11A32G11

- humanized, 8ng/ml
- chimeric, 8ng/ml (RLU vs Dilution of RV-GP: 1:3200, 1:1600, 1:800, 1:400, 1:200, 1:100, 1:50)

FIG. 15D

Detection activity of 7G11A32G11

- humanized, 200ng/ml
- chimeric, 200ng/ml (RLU vs Dilution of RV-GP: 1:3200, 1:1600, 1:800, 1:400, 1:200, 1:100, 1:50)

1) 5000 IU/kg RVNA cocktail and Vaccine 2) 1000 IU/kg RVNA cocktail and Vaccine 3) 200 IU/kg RVNA cocktail and Vaccine 4) 20 IU/kg HRIG and Vaccine 5) Only Vaccine 6) Negative control

SEQUENCE LISTING

<160> NUMBER OF SEQ ID NOS: 67

<210> SEQ ID NO 1
<211> LENGTH: 20
<212> TYPE: DNA
<213> ORGANISM: Artificial
<220> FEATURE:
<223> OTHER INFORMATION: Synthetic Primer

<400> SEQUENCE: 1
gccagtggat agaccgatgg                                                        20

<210> SEQ ID NO 2
<211> LENGTH: 16
<212> TYPE: DNA
<213> ORGANISM: Artificial
<220> FEATURE:
<223> OTHER INFORMATION: Synthetic Primer

<400> SEQUENCE: 2
acagtcactg agctgc                                                            16

<210> SEQ ID NO 3
<211> LENGTH: 21
<212> TYPE: DNA
<213> ORGANISM: Artificial
<220> FEATURE:
<223> OTHER INFORMATION: Synthetic Primer

<400> SEQUENCE: 3
gatggataca gttggtgcag c                                                      21

<210> SEQ ID NO 4
<211> LENGTH: 420
<212> TYPE: DNA
<213> ORGANISM: Mus musculus

<400> SEQUENCE: 4
atgggaggga tctggatctt tctcttcctc ctgtcaggaa ctgcaggtgc ccactctgag      60
atccagctgc agcagactgg acctgagctg gtgaagcctg ggcttcagt gaagatatcc      120 tgcaaggctt ctggttattc attcactgac tacatcatgc tctgggtgaa gcagagccat      180
ggaaagagcc ttgagtggat tggagatatt tatccttact atggtagtac tagctacaat      240
ctgaagttca gggcaaggc cacattgact gtagacaaat cttccagcac agcctacatg      300
cagctcaaca gtctgacatc tgaggactct gcagtctatt actgtgcaag gcagggcggg      360
gatggtaact acgtcctctt tgactactgg ggccaaggca ccactctcac agtctcctca      420

<210> SEQ ID NO 5
<211> LENGTH: 140
<212> TYPE: PRT
<213> ORGANISM: Mus Musculus

<400> SEQUENCE: 5

Met Gly Gly Ile Trp Ile Phe Leu Phe Leu Leu Ser Gly Thr Ala Gly
1               5                   10                  15

Ala His Ser Glu Ile Gln Leu Gln Gln Thr Gly Pro Glu Leu Val Lys
            20                  25                  30

Pro Gly Ala Ser Val Lys Ile Ser Cys Lys Ala Ser Gly Tyr Ser Phe
        35                  40                  45

Thr Asp Tyr Ile Met Leu Trp Val Lys Gln Ser His Gly Lys Ser Leu
    50                  55                  60

```
Glu Trp Ile Gly Asp Ile Tyr Pro Tyr Tyr Gly Ser Thr Ser Tyr Asn
 65                  70                  75                  80

Leu Lys Phe Lys Gly Lys Ala Thr Leu Thr Val Asp Lys Ser Ser Ser
                 85                  90                  95

Thr Ala Tyr Met Gln Leu Asn Ser Leu Thr Ser Glu Asp Ser Ala Val
            100                 105                 110

Tyr Tyr Cys Ala Arg Gln Gly Gly Asp Gly Asn Tyr Val Leu Phe Asp
        115                 120                 125

Tyr Trp Gly Gln Gly Thr Thr Leu Thr Val Ser Ser
130                 135                 140

<210> SEQ ID NO 6
<211> LENGTH: 381
<212> TYPE: DNA
<213> ORGANISM: Mus musculus

<400> SEQUENCE: 6
atggagtcac agactcaggt ctttgtatac atgttgctgt ggttgtctgg tgttgatgga      60
gacattgtga tgacccagtc tcaaaaattc atgtccacat cagtaggaga cagggtcagc     120
gtcacctgca aggccagtca gaatgtgggt actactgttg cctggtatca acagaaacca     180
ggacaatctc ctaaagcact gatttactcg gcatcctacc ggtacagtgg agtccctgat     240
cgcttcacag gcagtggatc tgggacagat ttcactctca ccatcagcaa tgtgcagtct     300
gaagacttgg cagaatattt ctgtcagcaa tataacagct atccattcac gttcggctcg     360
gggacaaagt tggaaataaa a                                               381

<210> SEQ ID NO 7
<211> LENGTH: 127
<212> TYPE: PRT
<213> ORGANISM: Mus musculus

<400> SEQUENCE: 7

Met Glu Ser Gln Thr Gln Val Phe Val Tyr Met Leu Leu Trp Leu Ser
  1               5                  10                  15

Gly Val Asp Gly Asp Ile Val Met Thr Gln Ser Gln Lys Phe Met Ser
                 20                  25                  30

Thr Ser Val Gly Asp Arg Val Ser Val Thr Cys Lys Ala Ser Gln Asn
             35                  40                  45

Val Gly Thr Thr Val Ala Trp Tyr Gln Gln Lys Pro Gly Gln Ser Pro
         50                  55                  60

Lys Ala Leu Ile Tyr Ser Ala Ser Tyr Arg Tyr Ser Gly Val Pro Asp
 65                  70                  75                  80

Arg Phe Thr Gly Ser Gly Ser Gly Thr Asp Phe Thr Leu Thr Ile Ser
                 85                  90                  95

Asn Val Gln Ser Glu Asp Leu Ala Glu Tyr Phe Cys Gln Gln Tyr Asn
            100                 105                 110

Ser Tyr Pro Phe Thr Phe Gly Ser Gly Thr Lys Leu Glu Ile Lys
        115                 120                 125

<210> SEQ ID NO 8
<211> LENGTH: 33
<212> TYPE: DNA
<213> ORGANISM: Artificial
<220> FEATURE:
<223> OTHER INFORMATION: Synthetic Primer

<400> SEQUENCE: 8
```

```
gcaactagta ccaccatggg agggatctgg atc                                     33
```

<210> SEQ ID NO 9
<211> LENGTH: 49
<212> TYPE: DNA
<213> ORGANISM: Artificial
<220> FEATURE:
<223> OTHER INFORMATION: Synthetic Primer

<400> SEQUENCE: 9

```
gggaagcttg ttttaaggac tcacctgagg agactgtgag agtggtgcc                    49
```

<210> SEQ ID NO 10
<211> LENGTH: 454
<212> TYPE: DNA
<213> ORGANISM: Artificial
<220> FEATURE:
<223> OTHER INFORMATION: Chimeric gene

<400> SEQUENCE: 10

```
actagtacca ccatgggagg gatctggatc tttctcttcc tcctgtcagg aactgcaggt        60
gcccactctg agatccagct gcagcagact ggacctgagc tggtgaagcc tggggcttca       120
gtgaagatat cctgcaaggc ttctggttat tcattcactg actacatcat gctctgggtg       180
aagcagagcc atggaaagag ccttgagtgg attggagata tttatcctta ctatggtagt       240
actagctaca atctgaagtt caagggcaag gccacattga ctgtagacaa atcttccagc       300
acagcctaca tgcagctcaa cagtctgaca tctgaggact ctgcagtcta ttactgtgca       360
aggcagggcg gggatggtaa ctacgtcctc tttgactact ggggccaagg caccactctc       420
acagtctcct caggtgagtc cttaaaacaa gctt                                   454
```

<210> SEQ ID NO 11
<211> LENGTH: 140
<212> TYPE: PRT
<213> ORGANISM: Artificial
<220> FEATURE:
<223> OTHER INFORMATION: Chimeric protein

<400> SEQUENCE: 11

```
Met Gly Gly Ile Trp Ile Phe Leu Phe Leu Leu Ser Gly Thr Ala Gly
1               5                   10                  15

Ala His Ser Glu Ile Gln Leu Gln Gln Thr Gly Pro Glu Leu Val Lys
            20                  25                  30

Pro Gly Ala Ser Val Lys Ile Ser Cys Lys Ala Ser Gly Tyr Ser Phe
        35                  40                  45

Thr Asp Tyr Ile Met Leu Trp Val Lys Gln Ser His Gly Lys Ser Leu
    50                  55                  60

Glu Trp Ile Gly Asp Ile Tyr Pro Tyr Tyr Gly Ser Thr Ser Tyr Asn
65                  70                  75                  80

Leu Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Gln Gly Gly Asp Gly Asn Tyr Val Leu Phe Asp
        115                 120                 125

Tyr Trp Gly Gln Gly Thr Thr Leu Thr Val Ser Ser
    130                 135                 140
```

<210> SEQ ID NO 12
<211> LENGTH: 33
<212> TYPE: DNA
<213> ORGANISM: Artificial
<220> FEATURE:
<223> OTHER INFORMATION: Synthetic primer

<400> SEQUENCE: 12
gctgctagca ccaccatgga gtcacagact cag                                33

<210> SEQ ID NO 13
<211> LENGTH: 50
<212> TYPE: DNA
<213> ORGANISM: Artificial
<220> FEATURE:
<223> OTHER INFORMATION: Synthetic primer

<400> SEQUENCE: 13
ggggaattcg caaaagtcta cttacgtttt atttccaact ttgtccccga              50

<210> SEQ ID NO 14
<211> LENGTH: 416
<212> TYPE: DNA
<213> ORGANISM: Artificial
<220> FEATURE:
<223> OTHER INFORMATION: Chimeric gene

<400> SEQUENCE: 14
gctagcacca ccatggagtc acagactcag gtctttgtat acatgttgct gtggttgtct    60
ggtgttgatg gagacattgt gatgacccag tctcaaaaat tcatgtccac atcagtagga  120
gacagggtca gcgtcacctg caaggccagt cagaatgtgg gtactactgt tgcctggtat  180
caacagaaac caggacaatc tcctaaagca ctgatttact cggcatccta ccggtacagt  240
ggagtccctg atcgcttcac aggcagtgga tctgggacag atttcactct caccatcagc  300
aatgtgcagt ctgaagactt ggcagaatat ttctgtcagc aatataacag ctatccattc  360
acgttcggct cggggacaaa gttggaaata aaacgtaagt agacttttgc gaattc       416

<210> SEQ ID NO 15
<211> LENGTH: 127
<212> TYPE: PRT
<213> ORGANISM: Artificial
<220> FEATURE:
<223> OTHER INFORMATION: Chimeric protein

<400> SEQUENCE: 15

Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Val Thr Cys Lys Ala Ser Gln Asn
        35                  40                  45

Val Gly Thr Thr Val Ala Trp Tyr Gln Gln Lys Pro Gly Gln Ser Pro
    50                  55                  60

Lys Ala Leu Ile Tyr Ser Ala Ser Tyr Arg Tyr Ser Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Glu Tyr Phe Cys Gln Gln Tyr Asn
            100                 105                 110

Ser Tyr Pro Phe Thr Phe Gly Ser Gly Thr Lys Leu Glu Ile Lys

<210> SEQ ID NO 16
<211> LENGTH: 455
<212> TYPE: DNA
<213> ORGANISM: Artificial
<220> FEATURE:
<223> OTHER INFORMATION: Humanized gene

<400> SEQUENCE: 16

```
actagtacca ccatggactg gacctggagg atcctctttt tggtggcagc agccacaggt      60
gcccactccc aggtccagct tgtgcagtct ggggctgaag tgaaaaagcc tggggcctca     120
gtgaaggttt cctgcaaggc ttctggatac tcattcactg actatatcat gctttgggtg     180
cgccaggccc ctggacaaag gcttgagtgg attggagata tctatcctta ctatggcagt     240
acaagctata atctgaagtt caagggcaag gccaccctca ccgtcgacac atccgcgagc     300
acagcctaca tggagctcag cagcctgaga tctgaagaca ccgctgtgta ttactgtgcc     360
aggcagggcg gcgatggaaa ctacgtcctc tttgactact ggggccaggg aaccctggtc     420
accgtctcct caggtgagtc tgctgtacta agctt                                455
```

<210> SEQ ID NO 17
<211> LENGTH: 140
<212> TYPE: PRT
<213> ORGANISM: Artificial
<220> FEATURE:
<223> OTHER INFORMATION: Humanized protein

<400> SEQUENCE: 17

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Thr Asp Tyr Ile Met Leu Trp Val Arg Gln Ala Pro Gly Gln Arg Leu
    50                  55                  60

Glu Trp Ile Gly Asp Ile Tyr Pro Tyr Tyr Gly Ser Thr Ser Tyr Asn
65                  70                  75                  80

Leu Lys Phe Lys Gly Lys Ala Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gln Gly Gly Asp Gly Asn Tyr Val Leu Phe Asp
        115                 120                 125

Tyr Trp Gly Gln Gly Thr Leu Val Thr Val Ser Ser
    130                 135                 140
```

<210> SEQ ID NO 18
<211> LENGTH: 416
<212> TYPE: DNA
<213> ORGANISM: Artificial
<220> FEATURE:
<223> OTHER INFORMATION: Humanized gene

<400> SEQUENCE: 18

```
gctagcacca ccatggagtc acagactcag gtctttgtgt acatgttgct gtggttgtct      60
ggtgttgatg gagacattca gatgacccag tctccatcct ccctgtccgc atcagtcgga     120
```

```
gacagggtca ccatcacctg caaggccagt cagaatgtgg gtactactgt tgcctggtat    180
caacagaaac caggaaaagc ccctaaagtc ctgatttact ccgcatccta tcggtacagt    240
ggagtccctt cacgcttcag tggcagtgga tctgggacag atttcactct caccatcagc    300
agtctgcagc tgaagactt tgcaacttat tactgtcagc aatataacag ctatccattc    360
acgttcggcc aggggacaaa gttggaaatc aaacgtaagt acttttttcc gaattc        416

<210> SEQ ID NO 19
<211> LENGTH: 127
<212> TYPE: PRT
<213> ORGANISM: Artificial
<220> FEATURE:
<223> OTHER INFORMATION: Humanized protein

<400> SEQUENCE: 19

Met Glu Ser Gln Thr Gln Val Phe Val Tyr Met Leu Leu Trp Leu Ser
1               5                   10                  15

Gly Val Asp Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asn
        35                  40                  45

Val Gly Thr Thr Val Ala Trp Tyr Gln Gln Lys Pro Gly Lys Ala Pro
    50                  55                  60

Lys Val Leu Ile Tyr Ser Ala Ser Tyr Arg Tyr Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Phe Thr Phe Gly Gln Gly Thr Lys Leu Glu Ile Lys
        115                 120                 125

<210> SEQ ID NO 20
<211> LENGTH: 416
<212> TYPE: DNA
<213> ORGANISM: Artificial
<220> FEATURE:
<223> OTHER INFORMATION: Humanized gene

<400> SEQUENCE: 20
gctagcacca ccatggagtc acagactcag gtctttgtgt acatgttgct gtggttgtct    60
ggtgttgatg gagacattca gatgacccag tctccatcct ccctgtccgc atcagtcgga    120
gacagggtca ccatcacctg caaggccagt cagaatgtgg gtactactgt tgcctggtat    180
caacagaaac caggaaaagc ccctaaagtc ctgatttact ccgcatccta tcggtacagt    240
ggagtccctt cacgcttcag tggcagtgga tctgggacag atttcactct caccatcagc    300
agtctgcagc tgaagactt tgcaacttat tactgtcagc aatataacag ctatccattc    360
acgttcggcc aggggacaaa gttggaaatc aaacgtaagt acttttttcc gaattc        416

<210> SEQ ID NO 21
<211> LENGTH: 127
<212> TYPE: PRT
<213> ORGANISM: Artificial
<220> FEATURE:
<223> OTHER INFORMATION: Humanized protein

<400> SEQUENCE: 21

Met Glu Ser Gln Thr Gln Val Phe Val Tyr Met Leu Leu Trp Leu Ser
```

```
 1               5                  10                 15
Gly Val Asp Gly Asp Ile Gln Met Thr Gln Ser Pro Ser Ser Leu Ser
             20                  25                 30
Ala Ser Val Gly Asp Arg Val Thr Ile Thr Cys Lys Ala Ser Gln Asn
             35                  40                 45
Val Gly Thr Thr Val Ala Trp Tyr Gln Gln Lys Pro Gly Lys Ala Pro
             50                  55                 60
Lys Val Leu Ile Tyr Ser Ala Ser Tyr Arg Tyr Ser Gly Val Pro Ser
65                   70                  75                 80
Arg Phe Ser Gly Ser Gly Ser Gly Thr Asp Phe Thr Leu Thr Ile Ser
                 85                  90                 95
Ser Leu Gln Pro Glu Asp Phe Ala Thr Tyr Tyr Cys Gln Gln Tyr Asn
               100                 105                110
Ser Tyr Pro Phe Thr Phe Gly Gln Gly Thr Lys Leu Glu Ile Lys
               115                 120                125
```

<210> SEQ ID NO 22
<211> LENGTH: 1413
<212> TYPE: DNA
<213> ORGANISM: Artificial
<220> FEATURE:
<223> OTHER INFORMATION: Recombinant plasmid

<400> SEQUENCE: 22

| | | | | |
|---|---|---|---|---|
| atgggaggga | tctggatctt | tctcttcctc | ctgtcaggaa | ctgcaggtgc | ccactctgag | 60 |
| atccagctgc | agcagactgg | acctgagctg | gtgaagcctg | gggcttcagt | gaagatatcc | 120 |
| tgcaaggctt | ctggttattc | attcactgac | tacatcatgc | tctgggtgaa | gcagagccat | 180 |
| ggaaagagcc | ttgagtggat | tggagatatt | tatccttact | atggtagtac | tagctacaat | 240 |
| ctgaagttca | agggcaaggc | cacattgact | gtagacaaat | cttccagcac | agcctacatg | 300 |
| cagctcaaca | gtctgacatc | tgaggactct | gcagtctatt | actgtgcaag | gcagggcggg | 360 |
| gatggtaact | acgtcctctt | tgactactgg | ggccaaggca | ccactctcac | agtctcctca | 420 |
| gcctccacca | agggcccatc | ggtcttcccc | ctggcaccct | cctccaagag | cacctctggg | 480 |
| ggcacagcgg | ccctgggctg | cctggtcaag | gactacttcc | ccgaaccggt | gacggtgtcg | 540 |
| tggaactcag | gcgccctgac | cagcggcgtg | cacaccttcc | cggctgtcct | acagtcctca | 600 |
| ggactctact | ccctcagcag | cgtggtgacc | gtgccctcca | gcagcttggg | cacccagacc | 660 |
| tacatctgca | acgtgaatca | caagcccagc | aacaccaagg | tggacaagaa | agttgagccc | 720 |
| aaatcttgtg | acaaaactca | cacatgccca | ccgtgcccag | cacctgaact | cctgggggga | 780 |
| ccgtcagtct | tcctcttccc | cccaaaaccc | aaggacaccc | tcatgatctc | ccggacccct | 840 |
| gaggtcacat | gcgtggtggt | ggacgtgagc | cacgaagacc | ctgaggtcaa | gttcaactgg | 900 |
| tacgtggacg | gcgtggaggt | gcataatgcc | aagacaaagc | cgcgggagga | gcagtacaac | 960 |
| agcacgtacc | gtgtggtcag | cgtcctcacc | gtcctgcacc | aggactggct | gaatggcaag | 1020 |
| gagtacaagt | gcaaggtctc | caacaaagcc | ctcccagccc | ccatcgagaa | aaccatctcc | 1080 |
| aaagccaaag | ggcagccccg | agaaccacag | gtgtacaccc | tgcccccatc | ccgggatgag | 1140 |
| ctgaccaaga | accaggtcag | cctgacctgc | ctggtcaaag | gcttctatcc | cagcgacatc | 1200 |
| gccgtggagt | gggagagcaa | tgggcagccg | gagaacaact | acaagaccac | gcctcccgtg | 1260 |
| ctggactccg | acggctcctt | cttcctctac | agcaagctca | ccgtggacaa | gagcaggtgg | 1320 |
| cagcagggga | acgtcttctc | atgctccgtg | atgcatgagg | ctctgcacaa | ccactacacg | 1380 | cagaagagcc tctccctgtc tccgggtaaa tga                                      1413

<210> SEQ ID NO 23
<211> LENGTH: 470
<212> TYPE: PRT
<213> ORGANISM: Artificial Sequence
<220> FEATURE:
<223> OTHER INFORMATION: Recombinant protein

<400> SEQUENCE: 23

Met Gly Gly Ile Trp Ile Phe Leu Phe Leu Leu Ser Gly Thr Ala Gly
1               5                   10                  15

Ala His Ser Glu Ile Gln Leu Gln Gln Thr Gly Pro Glu Leu Val Lys
            20                  25                  30

Pro Gly Ala Ser Val Lys Ile Ser Cys Lys Ala Ser Gly Tyr Ser Phe
        35                  40                  45

Thr Asp Tyr Ile Met Leu Trp Val Lys Gln Ser His Gly Lys Ser Leu
    50                  55                  60

Glu Trp Ile Gly Asp Ile Tyr Pro Tyr Tyr Gly Ser Thr Ser Tyr Asn
65                  70                  75                  80

Leu Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Gln Gly Gly Asp Gly Asn Tyr Val Leu Phe Asp
        115                 120                 125

Tyr Trp Gly Gln Gly Thr Thr Leu Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu

```
                355                 360                 365
Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 24
<211> LENGTH: 705
<212> TYPE: DNA
<213> ORGANISM: Artificial
<220> FEATURE:
<223> OTHER INFORMATION: Recombinant plasmid

<400> SEQUENCE: 24
atggagtcac agactcaggt ctttgtatac atgttgctgt ggttgtctgg tgttgatgga      60
gacattgtga tgacccagtc tcaaaaattc atgtccacat cagtaggaga cagggtcagc    120
gtcacctgca aggccagtca gaatgtgggt actactgttg cctggtatca acagaaacca    180
ggacaatctc ctaaagcact gatttactcg gcatcctacc ggtacagtgg agtccctgat    240
cgcttcacag gcagtggatc tgggacagat ttcactctca ccatcagcaa tgtgcagtct    300
gaagacttgg cagaatattt ctgtcagcaa tataacagct atccattcac gttcggctcg    360
gggacaaagt tggaaataaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga aaacacaaa gtctacgcct gcgaagtcac ccatcagggc    660
ctgagctcgc ccgtcacaaa gagcttcaac aggggagagt gttag                   705

<210> SEQ ID NO 25
<211> LENGTH: 234
<212> TYPE: PRT
<213> ORGANISM: Artificial
<220> FEATURE:
<223> OTHER INFORMATION: Recombinant protein

<400> SEQUENCE: 25

Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Val Thr Cys Lys Ala Ser Gln Asn
        35                  40                  45

Val Gly Thr Thr Val Ala Trp Tyr Gln Gln Lys Pro Gly Gln Ser Pro
    50                  55                  60
```

Lys Ala Leu Ile Tyr Ser Ala Ser Tyr Arg Tyr Ser Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Glu Tyr Phe Cys Gln Gln Tyr Asn
            100                 105                 110

Ser Tyr Pro Phe Thr Phe Gly Ser Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 26
<211> LENGTH: 1413
<212> TYPE: DNA
<213> ORGANISM: Artificial
<220> FEATURE:
<223> OTHER INFORMATION: Recombinant plasmid

<400> SEQUENCE: 26

```
atggactgga cctggaggat cctcttttg gtggcagcag ccacaggtgc ccactcccag      60
gtccagcttg tgcagtctgg ggctgaagtg aaaaagcctg ggcctcagt gaaggtttcc    120
tgcaaggctt ctggatactc attcactgac tatatcatgc tttgggtgcg ccaggcccct   180
ggacaaaggc ttgagtggat ggagatatc tatccttact atggcagtac aagctataat    240
ctgaagttca agggcaaggc caccctcacc gtcgacacat ccgcgagcac agcctacatg   300
gagctcagca gcctgagatc tgaagacacc gctgtgtatt actgtgccag caggggcggc   360
gatggaaact acgtcctctt tgactactgg ggccagggaa ccctggtcac cgtctcctca   420
gcctccacca agggcccatc ggtcttcccc ctggcaccct cctccaagag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
ggactctact ccctcagcag cgtggtgacc gtgccctcca gcagcttggg cacccagacc   660
tacatctgca acgtgaatca caagcccagc aacaccaagg tggacaagaa agttgagccc   720
aaatcttgtg acaaaactca cacatgccca ccgtgcccag cacctgaact cctggggga   780
ccgtcagtct tcctcttccc cccaaaaccc aaggacaccc tcatgatctc ccggaccccct   840
gaggtcacat gcgtggtggt ggacgtgagc cacgaagacc ctgaggtcaa gttcaactgg   900
tacgtggacg gcgtggaggt gcataatgcc aagacaaagc cgcgggagga gcagtacaac   960
agcacgtacc gtgtggtcag cgtcctcacc gtcctgcacc aggactggct gaatggcaag  1020
gagtacaagt gcaaggtctc caacaaagcc ctcccagccc ccatcgagaa aaccatctcc  1080
```

```
aaagccaaag ggcagccccg agaaccacag gtgtacaccc tgcccccatc ccgggatgag    1140
ctgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa tga                                 1413

<210> SEQ ID NO 27
<211> LENGTH: 470
<212> TYPE: PRT
<213> ORGANISM: Artificial
<220> FEATURE:
<223> OTHER INFORMATION: Recombinant protein

<400> SEQUENCE: 27

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Thr Asp Tyr Ile Met Leu Trp Val Arg Gln Ala Pro Gly Gln Arg Leu
    50                  55                  60

Glu Trp Ile Gly Asp Ile Tyr Pro Tyr Tyr Gly Ser Thr Ser Tyr Asn
65                  70                  75                  80

Leu Lys Phe Lys Gly Lys Ala Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gln Gly Gly Asp Gly Asn Tyr Val Leu Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300
```

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
    355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Leu Tyr Ser Lys
        420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
450                 455                 460

Ser Leu Ser Pro Gly Lys
465             470

<210> SEQ ID NO 28
<211> LENGTH: 705
<212> TYPE: DNA
<213> ORGANISM: Artificial
<220> FEATURE:
<223> OTHER INFORMATION: Recombinant plasmid

<400> SEQUENCE: 28
atggagtcac agactcaggt ctttgtgtac atgttgctgt ggttgtctgg tgttgatgga      60
gacattcaga tgacccagtc tccatcctcc ctgtccgcat cagtcggaga cagggtcacc     120
atcacctgca aggccagtca gaatgtgggt actactgttg cctggtatca acagaaacca     180
ggaaaagccc ctaaagcact gatttactcc gcatcctatc ggtacagtgg agtcccttca     240
cgcttcagtg gcagtggatc tgggacagat ttcactctca ccatcagcag tctgcagcct     300
gaagactttg caacttatta ctgtcagcaa tataacagct atccattcac gttcggccag     360
gggacaaagt tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac agggagagt gttag                     705

<210> SEQ ID NO 29
<211> LENGTH: 234
<212> TYPE: PRT
<213> ORGANISM: Artificial
<220> FEATURE:
<223> OTHER INFORMATION: Recombinant Protein

<400> SEQUENCE: 29

Met Glu Ser Gln Thr Gln Val Phe Val Tyr Met Leu Leu Trp Leu Ser
1               5                   10                  15

Gly Val Asp Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asn
        35                  40                  45

Val Gly Thr Thr Val Ala Trp Tyr Gln Gln Lys Pro Gly Lys Ala Pro
50                  55                  60

Lys Ala Leu Ile Tyr Ser Ala Ser Tyr Arg Tyr Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Phe Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 30
<211> LENGTH: 705
<212> TYPE: DNA
<213> ORGANISM: Artificial
<220> FEATURE:
<223> OTHER INFORMATION: Recombinant plasmid

<400> SEQUENCE: 30
atggagtcac agactcaggt ctttgtgtac atgttgctgt ggttgtctgg tgttgatgga      60
gacattcaga tgacccagtc tccatcctcc ctgtccgcat cagtcggaga cagggtcacc     120
atcacctgca aggccagtca gaatgtgggt actactgttg cctggtatca acagaaacca     180
ggaaaagccc ctaaagtcct gatttactcc gcatcctatc ggtacagtgg agtcccttca     240
cgcttcagtg gcagtggatc tgggacagat ttcactctca ccatcagcag tctgcagcct     300
gaagactttg caacttatta ctgtcagcaa tataacagct atccattcac gttcggccag     360
gggacaaagt tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg     600 ctgagcaaag cagactacga gaaacacaaa gtctacgcct gcgaagtcac ccatcagggc     660
ctgagctcgc ccgtcacaaa gagcttcaac aggggagagt gttag                     705

<210> SEQ ID NO 31

<211> LENGTH: 234
<212> TYPE: PRT
<213> ORGANISM: Artificial
<220> FEATURE:
<223> OTHER INFORMATION: Recombinant protein

<400> SEQUENCE: 31

Met Glu Ser Gln Thr Gln Val Phe Val Tyr Met Leu Leu Trp Leu Ser
1               5                   10                  15

Gly Val Asp Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asn
        35                  40                  45

Val Gly Thr Thr Val Ala Trp Tyr Gln Gln Lys Pro Gly Lys Ala Pro
    50                  55                  60

Lys Val Leu Ile Tyr Ser Ala Ser Tyr Arg Tyr Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Phe Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 32
<211> LENGTH: 417
<212> TYPE: DNA
<213> ORGANISM: Mus musculus

<400> SEQUENCE: 32
atgaactttg tgctcagcct gattttcctt gccctcattt taagaggtgt cccgtgtgaa      60
gtgcagctgg tggagtctgg gggaggctta gtgaagcctg agggtccct gatactctcc     120 tgtgcagcct caggattcac tttcagtggc tttgccatgt cttgggttcg ccagactccg     180
gagaagaggc tggagtgggt cgcaaccatt agtagtggtg gtacttatac ctactctcca     240
gacagtgtga tgggtcgatt caccatctcc agagacaatg ccaagaacac cctgtacctg     300
caaatgagca gtctgaggtc tgaggacacg gccatgtatt actgtgcaag acgattacgt     360
cggaattact actctatgga ctactggggt caaggaacct cagtcaccgt ctcctca       417

<210> SEQ ID NO 33
<211> LENGTH: 139
<212> TYPE: PRT

<213> ORGANISM: Mus musculus

<400> SEQUENCE: 33

| | | | | | | | | | | | | | | |
|---|---|---|---|---|---|---|---|---|---|---|---|---|---|---|
| Met | Asn | Phe | Val | Leu | Ser | Leu | Ile | Phe | Leu | Ala | Leu | Ile | Leu | Arg | Gly |
| 1 | | | | 5 | | | | | 10 | | | | | 15 | |
| Val | Pro | Cys | Glu | Val | Gln | Leu | Val | Glu | Ser | Gly | Gly | Gly | Leu | Val | Lys |
| | | | 20 | | | | | 25 | | | | | 30 | | |
| Pro | Gly | Gly | Ser | Leu | Ile | Leu | Ser | Cys | Ala | Ala | Ser | Gly | Phe | Thr | Phe |
| | | 35 | | | | | 40 | | | | | 45 | | | |
| Ser | Gly | Phe | Ala | Met | Ser | Trp | Val | Arg | Gln | Thr | Pro | Glu | Lys | Arg | Leu |
| | 50 | | | | | 55 | | | | | 60 | | | | |
| Glu | Trp | Val | Ala | Thr | Ile | Ser | Ser | Gly | Gly | Thr | Tyr | Thr | Tyr | Ser | Pro |
| 65 | | | | | 70 | | | | | 75 | | | | | 80 |
| Asp | Ser | Val | Met | Gly | Arg | Phe | Thr | Ile | Ser | Arg | Asp | Asn | Ala | Lys | Asn |
| | | | | 85 | | | | | 90 | | | | | 95 | |
| Thr | Leu | Tyr | Leu | Gln | Met | Ser | Ser | Leu | Arg | Ser | Glu | Asp | Thr | Ala | Met |
| | | | 100 | | | | | 105 | | | | | 110 | | |
| Tyr | Tyr | Cys | Ala | Arg | Arg | Leu | Arg | Arg | Asn | Tyr | Tyr | Ser | Met | Asp | Tyr |
| | | 115 | | | | | 120 | | | | | 125 | | | |
| Trp | Gly | Gln | Gly | Thr | Ser | Val | Thr | Val | Ser | Ser | | | | | |
| | 130 | | | | | 135 | | | | | | | | | |

<210> SEQ ID NO 34
<211> LENGTH: 396
<212> TYPE: DNA
<213> ORGANISM: Mus musculus

<400> SEQUENCE: 34

```
atgaagctgc tgttctgct agtggtgctg ctattgttca cgagtccagc ctcaagcagt      60
gatgttgttc tgacccaagc tccactctct ctgcctgtca atattggaga tcaagcctct     120
atctcttgca gtctactaa gagtcttctg aatagtgatg gattcactta tttggactgg     180
tacctgcaga agccaggcca gtctccacag ctcctaatat atttggtttc taatcgattt     240
tctggagttc cagacaggtt cagtggcagt gggtcaggaa cagatttcac actcaagatc     300
agcagagtgg aggctgagga tttgggaatt tatttttgct tccagagtaa ctatcttcca     360
ttcacgttcg gctcggggac aaagttggaa ataaaa                               396
```

<210> SEQ ID NO 35
<211> LENGTH: 132
<212> TYPE: PRT
<213> ORGANISM: Mus musculus

<400> SEQUENCE: 35

| | | | | | | | | | | | | | | |
|---|---|---|---|---|---|---|---|---|---|---|---|---|---|---|---|
| Met | Lys | Leu | Pro | Val | Leu | Leu | Val | Leu | Leu | Phe | Thr | Ser | Pro | | |
| 1 | | | | 5 | | | | | 10 | | | | | 15 | |
| Ala | Ser | Ser | Ser | Asp | Val | Val | Leu | Thr | Gln | Ala | Pro | Leu | Ser | Leu | Pro |
| | | | 20 | | | | | 25 | | | | | 30 | | |
| Val | Asn | Ile | Gly | Asp | Gln | Ala | Ser | Ile | Ser | Cys | Lys | Ser | Thr | Lys | Ser |
| | | | 35 | | | | | 40 | | | | | 45 | | |
| Leu | Leu | Asn | Ser | Asp | Gly | Phe | Thr | Tyr | Leu | Asp | Trp | Tyr | Leu | Gln | Lys |
| | 50 | | | | | 55 | | | | | 60 | | | | |
| Pro | Gly | Gln | Ser | Pro | Gln | Leu | Leu | Ile | Tyr | Leu | Val | Ser | Asn | Arg | Phe |
| 65 | | | | | 70 | | | | | 75 | | | | | 80 |
| Ser | Gly | Val | Pro | Asp | Arg | Phe | Ser | Gly | Ser | Gly | Ser | Gly | Thr | Asp | Phe |
| | | | | 85 | | | | | 90 | | | | | 95 | |

Thr Leu Lys Ile Ser Arg Val Glu Ala Glu Asp Leu Gly Ile Tyr Phe
            100                 105                 110

Cys Phe Gln Ser Asn Tyr Leu Pro Phe Thr Phe Gly Ser Gly Thr Lys
        115                 120                 125

Leu Glu Ile Lys
    130

<210> SEQ ID NO 36
<211> LENGTH: 33
<212> TYPE: DNA
<213> ORGANISM: Artificial
<220> FEATURE:
<223> OTHER INFORMATION: Synthetic priemr

<400> SEQUENCE: 36
gcaactagta ccaccatgaa ctttgtgctc agc                         33

<210> SEQ ID NO 37
<211> LENGTH: 47
<212> TYPE: DNA
<213> ORGANISM: Artificial
<220> FEATURE:
<223> OTHER INFORMATION: Synthetic primer

<400> SEQUENCE: 37
gggaagcttg agaggccatt cttacctgag gagacggtga ctgaggt          47

<210> SEQ ID NO 38
<211> LENGTH: 448
<212> TYPE: DNA
<213> ORGANISM: Artificial
<220> FEATURE:
<223> OTHER INFORMATION: Chimeric gene

<400> SEQUENCE: 38
actagtacca ccatgaactt tgtgctcagc ctgattttcc ttgccctcat tttaagaggt    60
gtcccgtgtg aagtgcagct ggtggagtct gggggaggct tagtgaagcc tggagggtcc   120
ctgatactct cctgtgcagc ctcaggattc actttcagtg gctttgccat gtcttgggtt   180
cgccagactc cggagaagag gctggagtgg gtcgcaacca ttagtagtgg tggtacttat   240
acctactctc cagacagtgt gatgggtcga ttcaccatct ccagagacaa tgccaagaac   300
accctgtacc tgcaaatgag cagtctgagg tctgaggaca cggccatgta ttactgtgca   360
agacgattac gtcggaatta ctactctatg gactactggg gtcaaggaac ctcagtcacc   420
gtctcctcag gtgagtcctt aaaagctt                                      448

<210> SEQ ID NO 39
<211> LENGTH: 139
<212> TYPE: PRT
<213> ORGANISM: Artificial
<220> FEATURE:
<223> OTHER INFORMATION: Chmeric protein

<400> SEQUENCE: 39

Met Asn Phe Val Leu Ser Leu Ile Phe Leu Ala Leu Ile Leu Arg Gly
1               5                   10                  15

Val Pro Cys Glu Val Gln Leu Val Glu Ser Gly Gly Gly Leu Val Lys
            20                  25                  30

Pro Gly Gly Ser Leu Ile Leu Ser Cys Ala Ala Ser Gly Phe Thr Phe
        35                  40                  45

Ser Gly Phe Ala Met Ser Trp Val Arg Gln Thr Pro Glu Lys Arg Leu

```
                50                  55                  60
Glu Trp Val Ala Thr Ile Ser Ser Gly Gly Thr Tyr Thr Tyr Ser Pro
 65                  70                  75                  80

Asp Ser Val Met Gly Arg Phe Thr Ile Ser Arg Asp Asn Ala Lys Asn
                 85                  90                  95

Thr Leu Tyr Leu Gln Met Ser Ser Leu Arg Ser Glu Asp Thr Ala Met
                100                 105                 110

Tyr Tyr Cys Ala Arg Arg Leu Arg Arg Asn Tyr Tyr Ser Met Asp Tyr
            115                 120                 125

Trp Gly Gln Gly Thr Ser Val Thr Val Ser Ser
        130                 135
```

<210> SEQ ID NO 40
<211> LENGTH: 431
<212> TYPE: DNA
<213> ORGANISM: Artificial
<220> FEATURE:
<223> OTHER INFORMATION: Chimeric gene

<400> SEQUENCE: 40

```
gctagcacca ccatgaagct gcctgttctg ctagtggtgc tgctattgtt cacgagtcca      60
gcctcaagca gtgatgttgt tctgacccaa gctccactct ctctgcctgt caatattgga     120
gatcaagcct ctatctcttg caagtctact aagagtcttc tgaatagtga tggattcact     180
tatttggact ggtacctgca gaagccaggc cagtctccac agctcctaat atatttggtt     240
tctaatcgat ttctggagt  tccagacagg ttcagtggca gtgggtcagg aacagatttc     300
acactcaaga tcagcagagt ggaggctgag gatttgggaa tttattttg  cttccagagt     360
aactatcttc cattcacgtt cggctcgggg acaaagttgg aaataaaacg taagtagact     420
tttgcgaatt c                                                           431
```

<210> SEQ ID NO 41
<211> LENGTH: 132
<212> TYPE: PRT
<213> ORGANISM: Artificial
<220> FEATURE:
<223> OTHER INFORMATION: Chimeric protein

<400> SEQUENCE: 41

```
Met Lys Leu Pro Val Leu Leu Val Val Leu Leu Leu Phe Thr Ser Pro
 1               5                  10                  15

Ala Ser Ser Ser Asp Val Val Leu Thr Gln Ala Pro Leu Ser Leu Pro
                20                  25                  30

Val Asn Ile Gly Asp Gln Ala Ser Ile Ser Cys Lys Ser Thr Lys Ser
             35                  40                  45

Leu Leu Asn Ser Asp Gly Phe Thr Tyr Leu Asp Trp Tyr Leu Gln Lys
         50                  55                  60

Pro Gly Gln Ser Pro Gln Leu Leu Ile Tyr Leu Val Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Leu Gly Ile Tyr Phe
                100                 105                 110

Cys Phe Gln Ser Asn Tyr Leu Pro Phe Thr Phe Gly Ser Gly Thr Lys
            115                 120                 125

Leu Glu Ile Lys
        130
```

<210> SEQ ID NO 42
<211> LENGTH: 453
<212> TYPE: DNA
<213> ORGANISM: Artificial
<220> FEATURE:
<223> OTHER INFORMATION: Humanized gene

<400> SEQUENCE: 42

```
actagtacca ccatggaatt ggggctgagc tgggttttcc ttgttgctat tctggaaggc      60
gtccagtgtg aagtgcagct cgtggagtct gggggaggcc tcgtccagcc tgggggctcc     120
ctgatcctct cctgtgcagc ctctggattc acctttagtg gctttgccat gagctgggtc     180
cgccaggctc cagggaaggg gctcgagtgg gttgccacca ttagtagtgg cggaacttat     240
acctactctc cagactctgt gatgggccga ttcaccatct ccagagacaa cgccaagaac     300
tcactgtatc tgcaaatgaa cagcctgaga gccgaggaca cagctgtgta ttactgtgcc     360
agacgactgc gtcggaatta ctactctatg gactactggg gccaagggac aatggtcacc     420
gtctcctcag gtaagatggg ctttcctaag ctt                                  453
```

<210> SEQ ID NO 43
<211> LENGTH: 139
<212> TYPE: PRT
<213> ORGANISM: Artificial
<220> FEATURE:
<223> OTHER INFORMATION: Humanized protein

<400> SEQUENCE: 43

```
Met Glu Leu Gly Leu Ser Trp Val Phe Leu Val Ala Ile Leu Glu Gly
1               5                   10                  15
Val Gln Cys Glu Val Gln Leu Val Glu Ser Gly Gly Gly Leu Val Gln
            20                  25                  30
Pro Gly Gly Ser Leu Ile Leu Ser Cys Ala Ala Ser Gly Phe Thr Phe
        35                  40                  45
Ser Gly Phe Ala Met Ser Trp Val Arg Gln Ala Pro Gly Lys Gly Leu
    50                  55                  60
Glu Trp Val Ala Thr Ile Ser Ser Gly Gly Thr Tyr Thr Tyr Ser Pro
65                  70                  75                  80
Asp Ser Val Met Gly Arg Phe Thr Ile Ser Arg Asp Asn Ala Lys Asn
                85                  90                  95
Ser Leu Tyr Leu Gln Met Asn Ser Leu Arg Ala Glu Asp Thr Ala Val
            100                 105                 110
Tyr Tyr Cys Ala Arg Arg Leu Arg Arg Asn Tyr Tyr Ser Met Asp Tyr
        115                 120                 125
Trp Gly Gln Gly Thr Met Val Thr Val Ser Ser
    130                 135
```

<210> SEQ ID NO 44
<211> LENGTH: 432
<212> TYPE: DNA
<213> ORGANISM: Artificial
<220> FEATURE:
<223> OTHER INFORMATION: Humanized gene

<400> SEQUENCE: 44

```
gctagcacca ccatgaggct ccctgctcag ctcctggggc tgctgatgct ctgggtctct     60
ggatccagtg gggatattgt gatgactcag tctccactct cctgcccgt caccctgga     120
gagcctgcct ccatctcctg caagtctact aagagcctcc tgaatagtga tggattcact    180
```

```
tatttggatt ggtacctgca gaagccaggg cagtctccac agctcctgat ctatttggtt    240
tctaatcggt tttccggggt cccagacaga ttcagtggca gtggatcagg cacagatttt    300
acactgaaaa tcagcagagt ggaggctgag gatgttggcg tttattactg cttccaaagt    360
aactatcttc ctttcacttt cggcggcgga accaaagtcg agatcaaacg taagtgcact    420
ttcctagaat tc                                                        432
```

```
<210> SEQ ID NO 45
<211> LENGTH: 132
<212> TYPE: PRT
<213> ORGANISM: Artificial
<220> FEATURE:
<223> OTHER INFORMATION: Humanized protein

<400> SEQUENCE: 45

Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Pro
            20                  25                  30

Val Thr Pro Gly Glu Pro Ala Ser Ile Ser Cys Lys Ser Thr Lys Ser
        35                  40                  45

Leu Leu Asn Ser Asp Gly Phe Thr Tyr Leu Asp Trp Tyr Leu Gln Lys
    50                  55                  60

Pro Gly Gln Ser Pro Gln Leu Leu Ile Tyr Leu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Ser Asn Tyr Leu Pro Phe Thr Phe Gly Gly Gly Thr Lys
        115                 120                 125

Val Glu Ile Lys
    130
```

```
<210> SEQ ID NO 46
<211> LENGTH: 1410
<212> TYPE: DNA
<213> ORGANISM: Artificial
<220> FEATURE:
<223> OTHER INFORMATION: Recombinant plasmid

<400> SEQUENCE: 46
atgaactttg tgctcagcct gattttcctt gccctcattt taagaggtgt cccgtgtgaa     60
gtgcagctgg tggagtctgg gggaggctta gtgaagcctg agggtccct gatactctcc    120 tgtgcagcct caggattcac tttcagtggc tttgccatgt cttgggttcg ccagactccg    180
gagaagaggc tggagtgggt cgcaaccatt agtagtggtg gtacttatac ctactctcca    240
gacagtgtga tgggtcgatt caccatctcc agagacaatg ccaagaacac cctgtacctg    300
caaatgagca gtctgaggtc tgaggacacg gccatgtatt actgtgcaag acgattacgt    360
cggaattact actctatgga ctactggggt caaggaacct cagtcaccgt ctcctcagcc    420
tccaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
```

```
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag acaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggatgagctg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                     1410
```

<210> SEQ ID NO 47
<211> LENGTH: 469
<212> TYPE: PRT
<213> ORGANISM: Artificial
<220> FEATURE:
<223> OTHER INFORMATION: Recombinant protein

<400> SEQUENCE: 47

```
Met Asn Phe Val Leu Ser Leu Ile Phe Leu Ala Leu Ile Leu Arg Gly
1               5                   10                  15

Val Pro Cys Glu Val Gln Leu Val Glu Ser Gly Gly Gly Leu Val Lys
            20                  25                  30

Pro Gly Gly Ser Leu Ile Leu Ser Cys Ala Ala Ser Gly Phe Thr Phe
        35                  40                  45

Ser Gly Phe Ala Met Ser Trp Val Arg Gln Thr Pro Glu Lys Arg Leu
    50                  55                  60

Glu Trp Val Ala Thr Ile Ser Ser Gly Gly Thr Tyr Thr Tyr Ser Pro
65                  70                  75                  80

Asp Ser Val Met Gly Arg Phe Thr Ile Ser Arg Asp Asn Ala Lys Asn
                85                  90                  95

Thr Leu Tyr Leu Gln Met Ser Ser Leu Arg Ser Glu Asp Thr Ala Met
            100                 105                 110

Tyr Tyr Cys Ala Arg Arg Leu Arg Arg Asn Tyr Tyr Ser Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220
```

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
        260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
        340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 48
<211> LENGTH: 720
<212> TYPE: DNA
<213> ORGANISM: Artificial
<220> FEATURE:
<223> OTHER INFORMATION: Recombinant plasmid

<400> SEQUENCE: 48
atgaagctgc ctgttctgct agtggtgctg ctattgttca cgagtccagc ctcaagcagt     60
gatgttgttc tgacccaagc tccactctct ctgcctgtca atattggaga tcaagcctct    120
atctcttgca gtctactaa gagtcttctg aatagtgatg gattcactta tttggactgg    180
tacctgcaga agccaggcca gtctccacag ctcctaatat atttggtttc taatcgattt    240
tctggagttc cagacaggtt cagtggcagt gggtcaggaa cagatttcac actcaagatc    300
agcagagtgg aggctgagga tttgggaatt tattttttgct tccagagtaa ctatcttcca    360
ttcacgttcg gctcggggac aaagttggaa ataaaacgaa ctgtggctgc accatctgtc    420
ttcatcttcc cgccatctga tgagcagttg aaatctggaa cctgaataac ttctatccca    480
gagaggccaa agtacagtgg aaggtggata acgccctcca atcgggtaac tcccaggaga    540
gtgtcacaga gcaggacagc aaggacagca cctacagcct cagcagcacc ctgacgctga    600
gcaaagcaga ctacgagaaa cacaaagtct acgcctgcgt cacccatcag ggcctgagct    660

```
cgcccgtcac aaagagcttc aacaggggag agtgttagga atgcctctgt tgtgtgcctg    720
```

<210> SEQ ID NO 49
<211> LENGTH: 239
<212> TYPE: PRT
<213> ORGANISM: Artificial
<220> FEATURE:
<223> OTHER INFORMATION: Recombinant protein

<400> SEQUENCE: 49

```
Met Lys Leu Pro Val Leu Leu Val Val Leu Leu Phe Thr Ser Pro
1               5                   10                  15

Ala Ser Ser Ser Asp Val Val Leu Thr Gln Ala Pro Leu Ser Leu Pro
            20                  25                  30

Val Asn Ile Gly Asp Gln Ala Ser Ile Ser Cys Lys Ser Thr Lys Ser
        35                  40                  45

Leu Leu Asn Ser Asp Gly Phe Thr Tyr Leu Asp Trp Tyr Leu Gln Lys
    50                  55                  60

Pro Gly Gln Ser Pro Gln Leu Leu Ile Tyr Leu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Ile Tyr Phe
            100                 105                 110

Cys Phe Gln Ser Asn Tyr Leu Pro Phe Thr Phe Gly Ser Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 50
<211> LENGTH: 1410
<212> TYPE: DNA
<213> ORGANISM: Artificial
<220> FEATURE:
<223> OTHER INFORMATION: Recombinant plasmid

<400> SEQUENCE: 50

```
atggaattgg ggctgagctg ggttttcctt gttgctattc tggaaggcgt ccagtgtgaa    60
gtgcagctcg tggagtctgg gggaggcctc gtccagcctg ggggctccct gagactctcc   120
tgtgcagcct ctggattcac ctttagtggc tttgccatga gctgggtccg ccaggctcca   180
gggaaggggc tcgagtgggt tgccaccatt agtagtggcg aacttatac ctactctcca    240 gactctgtga tgggccgatt caccatctcc agagacaacg ccaagaactc actgtatctg   300
caaatgaaca gcctgagagc cgaggacaca gctgtgtatt actgtgccag acgactgcgt   360
```

```
cggaattact actctatgga ctactggggc caagggacaa tggtcaccgt ctcctcagcc    420
tccaccaagg gcccatcggt cttcccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg acccctgag    840 gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggatgagctg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga                                    1410
```

<210> SEQ ID NO 51
<211> LENGTH: 469
<212> TYPE: PRT
<213> ORGANISM: Artificial
<220> FEATURE:
<223> OTHER INFORMATION: Recombinant protein

<400> SEQUENCE: 51

```
Met Glu Leu Gly Leu Ser Trp Val Phe Leu Val Ala Ile Leu Glu Gly
 1               5                  10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Gly Phe Ala Met Ser Trp Val Arg Gln Ala Pro Gly Lys Gly Leu
        50                  55                  60

Glu Trp Val Ala Thr Ile Ser Ser Gly Gly Thr Tyr Thr Tyr Ser Pro
 65                  70                  75                  80

Asp Ser Val Met Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Arg Arg Leu Arg Arg Asn Tyr Tyr Ser Met Asp Tyr
        115                 120                 125

Trp Gly Gln Gly Thr Met Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175
```

```
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Ser Leu Gly Thr Gln Thr Tyr Ile Cys Asn Val
    210                 215                 220
Asn His Lys Pro Ser Asn Thr Lys Val Asp Lys Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Lys Ser Leu Ser Leu Ser Pro
        435                 440                 445
Gly Lys Gly Asn Val Phe Ser Cys Ser Val Met His Glu Ala Leu His
    450                 455                 460
Asn His Tyr Thr Gln
465
```

<210> SEQ ID NO 52
<211> LENGTH: 1410
<212> TYPE: DNA
<213> ORGANISM: Artificial
<220> FEATURE:
<223> OTHER INFORMATION: Recombinant plasmid

<400> SEQUENCE: 52

```
atggaattgg ggctgagctg ggttttcctt gttgctattc tggaaggcgt ccagtgtgaa    60
gtgcagctcg tggagtctgg gggaggcctc gtccagcctg ggggctccct gatcctctcc   120
tgtgcagcct ctggattcac ctttagtggc tttgccatga gctgggtccg ccaggctcca   180
gggaaggggc tcgagtgggt tgccaccatt agtagtggcg aacttatac ctactctcca    240 gactctgtga tggccgatt caccatctcc agagacaacg ccaagaactc actgtatctg    300
caaatgaaca gcctgagagc cgaggacaca gctgtgtatt actgtgccag acgactgcgt   360
```

```
cggaattact actctatgga ctactggggc caagggacaa tggtcaccgt ctcctcagcc      420
tccaccaagg gcccatcggt cttcccctg gcaccctcct ccaagagcac ctctgggggc       480
acagcggccc tgggctgcct ggtcaaggac tacttcccg aaccggtgac ggtgtcgtgg        540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggatgagctg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                      1410
```

<210> SEQ ID NO 53
<211> LENGTH: 469
<212> TYPE: PRT
<213> ORGANISM: Artificial
<220> FEATURE:
<223> OTHER INFORMATION: Recombinant protein

<400> SEQUENCE: 53

```
Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
                20                  25                  30

Pro Gly Gly Ser Leu Ile Leu Ser Cys Ala Ala Ser Gly Phe Thr Phe
            35                  40                  45

Ser Gly Phe Ala Met Ser Trp Val Arg Gln Ala Pro Gly Lys Gly Leu
        50                  55                  60

Glu Trp Val Ala Thr Ile Ser Ser Gly Gly Thr Tyr Thr Tyr Ser Pro
65                  70                  75                  80

Asp Ser Val Met Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Arg Leu Arg Arg Asn Tyr Tyr Ser Met Asp Tyr
        115                 120                 125

Trp Gly Gln Gly Thr Met Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175
```

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465

<210> SEQ ID NO 54
<211> LENGTH: 720
<212> TYPE: DNA
<213> ORGANISM: Artificial
<220> FEATURE:
<223> OTHER INFORMATION: Recombinant plasmid

<400> SEQUENCE: 54
atgaggctcc ctgctcagct cctggggctg ctgatgctct gggtctctgg atccagtggg      60
gatattgtga tgactcagtc tccactctcc ctgcccgtca cccctggaga gcctgcctcc     120
atctcctgca agtctactaa gagcctcctg aatagtgatg gattcactta tttggattgg     180
tacctgcaga agccagggca gtctccacag ctcctgatct atttggtttc taatcggttt     240
tccggggtcc cagacagatt cagtggcagt ggatcaggca cagattttac actgaaaatc     300
agcagagtgg aggctgagga tgttggcgtt tattactgct tccaaagtaa ctatcttcct     360

```
ttcactttcg gcggcggaac caaagtcgag atcaaacgaa ctgtggctgc accatctgtc      420
ttcatcttcc cgccatctga tgagcagttg aaatctggaa ctgcctctgt tgtgtgcctg      480
ctgaataact tctatcccag agaggccaaa gtacagtgga aggtggataa cgccctccaa      540
tcgggtaact cccaggagag tgtcacagag caggacagca aggacagcac ctacagcctc      600
agcagcaccc tgacgctgag caaagcagac tacgagaaac acaaagtcta cgcctgcgaa      660
gtcacccatc agggcctgag ctcgcccgtc acaaagagct tcaacagggg agagtgttag      720
```

<210> SEQ ID NO 55
<211> LENGTH: 239
<212> TYPE: PRT
<213> ORGANISM: Artificial
<220> FEATURE:
<223> OTHER INFORMATION: Recombinant protein

<400> SEQUENCE: 55

```
Met Arg Leu Pro Ala Gln Leu Leu Gly Leu Leu Met Leu Trp Val Ser
 1               5                  10                  15

Gly Ser Ser Gly Asp Ile Val Met Thr Gln Ser Pro Leu Ser Leu Pro
            20                  25                  30

Val Thr Pro Gly Glu Pro Ala Ser Ile Ser Cys Lys Ser Thr Lys Ser
        35                  40                  45

Leu Leu Asn Ser Asp Gly Phe Thr Tyr Leu Asp Trp Tyr Leu Gln Lys
    50                  55                  60

Pro Gly Gln Ser Pro Gln Leu Leu Ile Tyr Leu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Ser Asn Tyr Leu Pro Phe Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 56
<211> LENGTH: 5
<212> TYPE: PRT
<213> ORGANISM: Artificial
<220> FEATURE:
<223> OTHER INFORMATION: CDR peptide

<400> SEQUENCE: 56

Asp Tyr Ile Met Leu

<210> SEQ ID NO 57
<211> LENGTH: 17
<212> TYPE: PRT
<213> ORGANISM: Artificial
<220> FEATURE:
<223> OTHER INFORMATION: CDR peptide

<400> SEQUENCE: 57

Asp Ile Tyr Pro Tyr Tyr Gly Ser Thr Ser Tyr Asn Leu Lys Phe Lys
1               5                   10                  15
Gly

<210> SEQ ID NO 58
<211> LENGTH: 12
<212> TYPE: PRT
<213> ORGANISM: Artificial
<220> FEATURE:
<223> OTHER INFORMATION: CDR Peptide

<400> SEQUENCE: 58

Gln Gly Gly Asp Gly Asn Tyr Val Leu Phe Asp Tyr
1               5                   10

<210> SEQ ID NO 59
<211> LENGTH: 5
<212> TYPE: PRT
<213> ORGANISM: Artificial
<220> FEATURE:
<223> OTHER INFORMATION: CDR Peptide

<400> SEQUENCE: 59

Gly Phe Ala Met Ser
1               5

<210> SEQ ID NO 60
<211> LENGTH: 17
<212> TYPE: PRT
<213> ORGANISM: Artificial
<220> FEATURE:
<223> OTHER INFORMATION: CDR Peptide

<400> SEQUENCE: 60

Thr Ile Ser Ser Gly Gly Thr Tyr Thr Tyr Ser Pro Asp Ser Val Met
1               5                   10                  15
Gly

<210> SEQ ID NO 61
<211> LENGTH: 11
<212> TYPE: PRT
<213> ORGANISM: Artificial
<220> FEATURE:
<223> OTHER INFORMATION: CDR peptide

<400> SEQUENCE: 61

Arg Leu Arg Arg Asn Tyr Tyr Ser Met Asp Tyr
1               5                   10

<210> SEQ ID NO 62
<211> LENGTH: 11
<212> TYPE: PRT
<213> ORGANISM: Artificial
<220> FEATURE:
<223> OTHER INFORMATION: CDR peptide

```
<400> SEQUENCE: 62

Lys Ala Ser Gln Asn Val Gly Thr Thr Val Ala
1               5                   10

<210> SEQ ID NO 63
<211> LENGTH: 7
<212> TYPE: PRT
<213> ORGANISM: Artificial
<220> FEATURE:
<223> OTHER INFORMATION: CDR Peptide

<400> SEQUENCE: 63

Ser Ala Ser Tyr Arg Tyr Ser
1               5

<210> SEQ ID NO 64
<211> LENGTH: 9
<212> TYPE: PRT
<213> ORGANISM: Artificial
<220> FEATURE:
<223> OTHER INFORMATION: CDR peptide

<400> SEQUENCE: 64

Gln Gln Tyr Asn Ser Tyr Pro Phe Thr
1               5

<210> SEQ ID NO 65
<211> LENGTH: 16
<212> TYPE: PRT
<213> ORGANISM: Artificial
<220> FEATURE:
<223> OTHER INFORMATION: CDR peptide

<400> SEQUENCE: 65

Lys Ser Thr Lys Ser Leu Leu Asn Ser Asp Gly Phe Thr Tyr Leu Asp
1               5                   10                  15

<210> SEQ ID NO 66
<211> LENGTH: 7
<212> TYPE: PRT
<213> ORGANISM: Artificial
<220> FEATURE:
<223> OTHER INFORMATION: CDR peptide

<400> SEQUENCE: 66

Leu Val Ser Asn Arg Phe Ser
1               5

<210> SEQ ID NO 67
<211> LENGTH: 9
<212> TYPE: PRT
<213> ORGANISM: Artificial
<220> FEATURE:
<223> OTHER INFORMATION: CDR peptide

<400> SEQUENCE: 67

Phe Gln Ser Asn Tyr Leu Pro Phe Thr
1               5
```

COMPOSITIONS AND METHODS RELATED TO THE PREVENTION AND TREATMENT OF RABIES INFECTION

CROSS-REFERENCE TO RELATED APPLICATIONS

This application is the U.S. National Stage of International Application No. PCT/CN2012/076012, with international filing date May 24, 2012, the contents of which is incorporated herein by reference in its entirety.

TECHNICAL FIELD

This technology relates generally to the preparation of anti-rabies antibodies and uses of the same. In particular, the present technology relates to the preparation of rabies virus neutralizing antibodies and their use in the prevention and treatment of rabies infection.

BACKGROUND

The following description is provided to assist the understanding of the reader. None of the information provided or references cited is admitted to be prior art to the present methods.

Rabies is a viral infection with nearly worldwide distribution that affects principally wild and domestic animals, but also affects humans. The infection causes a devastating and, if untreated, nearly invariably fatal encephalitis. More than 70,000 people die each year from rabies infections, and millions more require post-exposure treatment.

The rabies virus is an enveloped, single-stranded RNA virus of the Rhabdovirus family and *Lyssavirus* genus. The genome of rabies virus codes five proteins: RNA-dependent RNA polymerase (L); a nucleoprotein (N); a phosphorylated protein (P); a matrix protein (M) located on the inner side of the viral protein envelope; and an external surface glycoprotein (G). The G protein (62-67 kDa) is a type-I glycoprotein composed of 505 amino acids, with two to four potential N-glycosylation sites, of which only one or two are glycosylated depending on the viral strain. The G protein forms protrusions covering the outer surface of the virion envelope and is known to induce the production virus-neutralizing antibodies (See Gaudin et al., 1999).

Rabies infection can be treated or prevented by both passive and active immunizations. Rabies post-exposure prophylaxis (PEP) includes prompt local wound care and administration of both passive (anti-rabies immunoglobulins) and active (vaccines) immunizations. Currently, the anti-rabies immunoglobulins (RIG) are prepared from the serum of either human (HRIG) or equine (ERIG) subjects. The use of immunoglobulins from these sources poses several difficulties, however, including disease transmission, cost, and in the case of equine immunoglobulin, adverse reactions such as anaphylactic shock. To overcome these disadvantages it has been suggested to use monoclonal antibodies capable of neutralizing rabies virus in post-exposure prophylaxis.

Rabies virus-neutralizing murine monoclonal antibodies are known in the art (See Schumacher et al., 1989). However, the use of murine antibodies in vivo is limited due to problems associated with administration of murine antibodies to humans, such as short serum half life, an inability to trigger certain human effector functions and elicitation of an unwanted dramatic immune response against the murine antibody in a human (the "human anti-mouse antibody" (HAMA) reaction). Currently, there is a need for new human rabies virus-neutralizing monoclonal antibodies having improved post-exposure prophylactic potential. It is advantageous that antibodies administered in conjunction with rabies vaccines not interfere with the antigenicity of the vaccine, thereby reducing its efficacy.

SUMMARY

The present technology relates generally to rabies virus neutralizing antibodies that bind to rabies virus glycoprotein. One advantage of these antibodies is that they have the capacity to reduce the infectivity of rabies virus, but do not interfere with the efficacy of a rabies vaccine. Currently available neutralizing antibodies for rabies simultaneously inhibit the efficacy of vaccination when they neutralize the viruses. Therefore, the dose of the conventional antibodies must be limited, which in turn only provides a minimum protection during the first week of infection. By contrast, the antibodies described herein overcome this problem by exhibiting superior neutralizing activity while not interfering with the efficacy of vaccination. Thus, the antibodies can be used in combination with a rabies vaccine to provide a treatment for acute infection as well as long-lasting immunity.

In one aspect, the present technology provides an isolated antibody that binds to rabies virus glycoprotein wherein the antibody comprises one or more heavy chain CDR amino acid sequences selected from the group consisting of DYIML (SEQ ID NO:56), DIYPYYGSTSYNLKFKG (SEQ ID NO:57), QGGDGNYVLFDY (SEQ ID NO:58), GFAMS (SEQ ID NO:59), TISSGGTYTYSPDSVMG (SEQ ID NO:60), and RLRRNYYSMDY (SEQ ID NO:61), or a variant thereof having one or more conservative amino acid substitutions; and the antibody comprises one or more light chain CDR amino acid sequences selected from the group consisting of KASQNVGTTVA (SEQ ID NO:62), SASYRYS (SEQ ID NO:63), QQYNSYPFT (SEQ ID NO:64), KSTKSLLNSDGFTYLD (SEQ ID NO:65), LVSNRFS (SEQ ID NO:66), and FQSNYLPFT (SEQ ID NO:67), or a variant thereof having one or more conservative amino acid substitutions.

In one embodiment, the antibody comprises heavy chain CDR sequences: DYIML (SEQ ID NO:56), DIYPYYGSTSYNLKFKG (SEQ ID NO:57), and QGGDGNYVLFDY (SEQ ID NO:58) and comprises light chain CDR sequences: KASQNVGTTVA (SEQ ID NO:62), SASYRYS (SEQ ID NO:63), and QQYNSYPFT (SEQ ID NO:64). In one embodiment, the antibody comprises heavy chain CDR sequences: GFAMS (SEQ ID NO:59), TISSGGTYTYSPDSVMG (SEQ ID NO:60), and RLRRNYYSMDY (SEQ ID NO:61) and comprises light chain CDR sequences: KSTKSLLNSDGFTYLD (SEQ ID NO:65), LVSNRFS (SEQ ID NO:66), and FQSNYLPFT (SEQ ID NO:67).

In one aspect, the present technology provides an isolated antibody that binds to rabies virus glycoprotein, wherein the antibody has the same antigen binding specificity as an antibody produced by a hybridoma cell line selected from the group consisting of CGMCC Accession Nos. 4805 and 4806.

In one embodiment, the antibody is capable of reducing the infectivity of rabies virus and does not interfere with the immunogenicity of a rabies vaccine. In one embodiment, the antibody is selected from a group consisting of a monoclonal antibody, a murine antibody, a chimeric antibody, and a humanized antibody.

In one embodiment, the present technology provides a pharmaceutical composition comprising a RVNA antibody or a cocktail of one or more RVNA antibodies and a pharmaceutically acceptable carrier. In one embodiment, the pharmaceutical composition comprises a cocktail of antibodies wherein a first antibody comprises heavy chain CDR sequences: DYIML (SEQ ID NO:56), DIYPYYGSTSYN-LKFKG (SEQ ID NO:57), and QGGDGNYVLFDY (SEQ ID NO:58) and comprises light chain CDR sequences: KASQNVGTTVA (SEQ ID NO:62), SASYRYS (SEQ ID NO:63), and QQYNSYPFT (SEQ ID NO:64); and wherein a second antibody comprises heavy chain CDR sequences: GFAMS (SEQ ID NO:59), TISSGGTYTYSPDSVMG (SEQ ID NO:60), and RLRRNYYSMDY (SEQ ID NO:61) and comprises light chain CDR sequences: KSTKSLLNSDG-FTYLD (SEQ ID NO:65), LVSNRFS (SEQ ID NO:66), and FQSNYLPFT (SEQ ID NO:67).

In one embodiment, the present technology provides the use of an RVNA antibody described herein in the manufacture of a medicament for treating rabies infection in a subject in need thereof. In one embodiment, the antibody reduces the infectivity of rabies virus but does not interfere with the immunogenicity of a rabies vaccine.

In one embodiment, the present technology provides a method for treating rabies infection in a subject in need thereof comprising administering to the subject an effective amount of one or more of the RVNA antibodies described herein. In one embodiment, the antibody is administered to the subject before, after, or simultaneously with a rabies vaccine. In one embodiment, the antibody is administered to the subject before, after, or simultaneously with an anti-rabies immunoglobulin.

In one aspect, the present technology provides a kit for treating rabies infection in a subject in need thereof comprising one more antibodies that bind to rabies virus glycoprotein and instructions for use of the antibody, wherein: the antibody comprises one or more heavy chain CDR amino acid sequences selected from the group consisting of DYIML (SEQ ID NO:56), DIYPYYGSTSYNLKFKG (SEQ ID NO:57), QGGDGNYVLFDY (SEQ ID NO:58), GFAMS (SEQ ID NO:59), TISSGGTYTYSPDSVMG (SEQ ID NO:60), and RLRRNYYSMDY (SEQ ID NO:61), or a variant thereof having one or more conservative amino acid substitutions; and the antibody comprises one or more light chain CDR amino acid sequences selected from the group consisting of KASQNVGTTVA (SEQ ID NO:62), SASYRYS (SEQ ID NO:63), QQYNSYPFT (SEQ ID NO:64), KSTKSLLNS-DGFTYLD (SEQ ID NO:65), LVSNRFS (SEQ ID NO:66), and FQSNYLPFT (SEQ ID NO:67), or a variant thereof having one or more conservative amino acid substitutions.

In one aspect, the present technology provides a kit for detecting rabies virus in a sample comprising an antibody that binds to rabies virus glycoprotein and instructions for use of the antibody, wherein: the antibody comprises one or more heavy chain CDR amino acid sequences selected from the group consisting of DYIML (SEQ ID NO:56), DIY-PYYGSTSYNLKFKG (SEQ ID NO:57), QGGDGNYV-LFDY (SEQ ID NO:58), GFAMS (SEQ ID NO:59), TISSG-GTYTYSPDSVMG (SEQ ID NO:60), and RLRRNYYSMDY (SEQ ID NO:61), or a variant thereof having one or more conservative amino acid substitutions; and the antibody comprises one or more light chain CDR amino acid sequences selected from the group consisting of KASQNVGTTVA (SEQ ID NO:62), SASYRYS (SEQ ID NO:63), QQYNSYPFT (SEQ ID NO:64), KSTKSLLNSDG-FTYLD (SEQ ID NO:65), LVSNRFS (SEQ ID NO:66), and FQSNYLPFT (SEQ ID NO:67), or a variant thereof having one or more conservative amino acid substitutions. In one embodiment, the antibody is coupled to one or more detectable labels. In one embodiment, the kit further comprises a secondary antibody that binds specifically to the rabies virus glycoprotein antibody. In one embodiment, the secondary antibody is coupled to one or more detectable labels.

In another aspect, the present technology provides an isolated nucleic acid encoding the RVNA antibodies described herein. In yet another aspect, the present technology provides a host cell comprising the isolated nucleic acid encoding the RVNA antibodies described herein.

BRIEF DESCRIPTION OF THE DRAWINGS

FIGS. 3A-4E are a series of graphs showing exemplary results of indirect CLEIA in which the five illustrative RVNAs bind to the rabies virus glycoprotein that was treated with different detergents. FIG. 3A: Binding capacity of 3D11E3 to RV glycoprotein; FIG. 3B: Binding capacity of 3H10D3 to RV glycoprotein; FIG. 3C: Binding capacity of 5A1C10 to RV glycoprotein; FIG. 3D: Binding capacity of 6F11C1 to RV glycoprotein; FIG. 3E: Binding capacity of 7G11A3 to RV glycoprotein.

FIGS. 4A-4J are a series of graphs showing the percent survival of mice challenged with a variety of rabies viruses in a mouse neutralization test (MNT). FIG. 4A: YNI (human); FIG. 4B: DRV (deer); FIG. 4C: HN35 (Human); FIG. 4D: SC-CD09 (dog); FIG. 4E: GN07 (dog); FIG. 4F: ZJ-HZ09 (dog); FIG. 4G: BD06 (dog); FIG. 4H: JX08-45 (badger); FIG. 4I: JX09-27 (badger); FIG. 4J: ZJ-LA (badger).

FIGS. 6A-6E are a series of graphs showing serum RVNA titers in non-challenged BALB/c mice. The mice in each treatment group (n=6 per group) were vaccinated with rabies vaccine and treated on day 0 with: FIG. 6A: 50 µg/dose 7G11A3; FIG. 6B: 50 µg/dose 3D11E3; FIG. 6C: 50 µg/dose 3H10D3; or FIG. 6D: 20 IU/kg human rabies immune globulin (BRIG). The mice in the control group (FIG. 6E) received only Rabipur® vaccine. On days 1, 3, 7, 14 and 28, blood was collected from mice orbit and mixed the 6 mice serum to 3 sera in each group. The RVNA titer in each serum sample was determined by a rapid fluorescent focus inhibition test, and geometric mean titers were calculated and plotted against time. The long lines represent means and the short lines represent max and min, respectively.

FIGS. 15A-15F are a series of graphs showing the binding curves of the humanized and chimeric RVNAs 2G11 to RV glycoprotein as determined by CLEIA. The chimeric and humanized 2G11 were used as capture and detection antibody, respectively. The glycoprotein was diluted to 1:50, 1:100, 1:200, 1:400, 1:800 and 1:1600 and then added in the micro-plate. Murine RV 3D10-HRP and mouse anti-human IgG-HRP were used as the enzyme conjugate. Related luminescence unit (RLU) represents the chemiluminescence signal.

DETAILED DESCRIPTION

Figure 1:
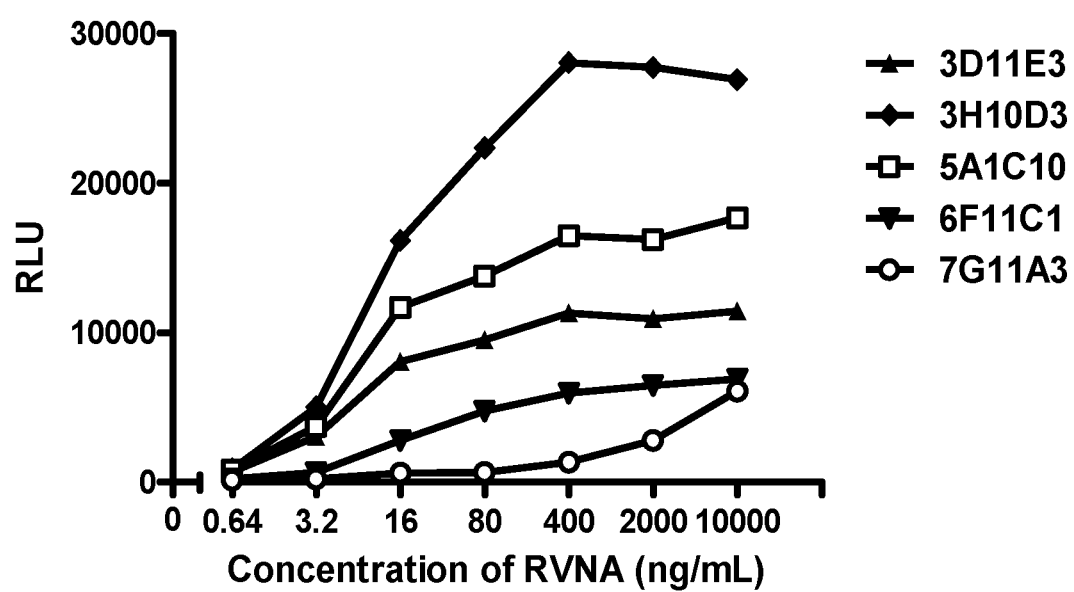
FIG. 1 is a graph showing exemplary binding curves of five illustrative rabies virus neutralizing antibodies (RVNAs) to RV glycoprotein.

The details of one or more embodiments of the present technology are set forth in the accompanying description below. In practicing the present methods, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art. The definitions of certain terms as used in this specification are provided below. Definitions of other terms may be found in the *Illustrated Dictionary of Immunology*, 2nd Edition (Cruse, J. M. and Lewis, R. E., Eds., Boca Raton, Fla.: CRC Press, 1995).

As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, intracranially, intrathecally, or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, the term "antibody" means a polypeptide comprising a framework region from an immunoglobulin gene or fragments thereof that specifically binds and recognizes an antigen, e.g., a rabies glycoprotein. Use of the term antibody is meant to include whole antibodies, including single-chain whole antibodies, and antigen-binding fragments thereof. The term "antibody" includes bispecific antibodies and multispecific antibodies so long as they exhibit the desired biological activity or function. The term antibody also refers to antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods, e.g., but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., Nature 341: 544-546, 1989), which consists of a $V_H$ domain; and (vi) an isolated complementarity determining region (CDR). As such "antibody fragments" can comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. Single-chain antibody molecules may comprise a polymer with a number of individual molecules, for example, dimmer, trimer or other polymers.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region).

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. In one embodiment, an "epitope" of the rabies virus glycoprotein is a region of the protein to which the anti-rabies antibodies of the present technology specifically bind.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated, e.g., rabies infection. The amount of a composition of the present technology administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present technology can also be administered in combination with one or more additional therapeutic compounds. For example, the compositions of the present technology may be incorporated into post-exposure prophylaxis for individuals exposed to rabies virus, and administered in combination with anti-therapeutics known in the art such as anti-rabies vaccines. The antibodies of the present technology are suitable for administration in combination with rabies vaccines including but not limited to purified chick embryo cell vaccine (PCECV; RabAvert®, Novartis, Basel, Switzerland; Rabipur®, Chiron Behring GmbH & Co., Liederbach, Germany), human diploid cell vaccine (HDCV; Imovax®, Sanofi Pasteur, Swiftwater, Pa., USA), rabies vaccine adsorbed (RVA), and human rabies immune globulin (HRIG). In some embodiments, "effective amount" refers to the quantity of anti-rabies antibody of the present technology which is partially or fully effective in neutralizing rabies virus.

As used herein, the term "rabies" refers to viruses of the Lyssavirus genus, in the family Rhabdoviridae, order Mononegavirales. Lyssaviruses have helical symmetry, with a length of about 180 nm and a cross-sectional diameter of about 75 nm. These viruses are enveloped and have a single stranded RNA genome with negative-sense. The genetic information is packaged as a ribonucleoprotein complex in which RNA is tightly bound by the viral nucleoprotein. The RNA genome of the virus encodes five genes whose order is highly conserved: nucleoprotein (N), phosphoprotein (P), matrix protein (M), glycoprotein (G) and the viral RNA polymerase (L).

As used herein, the term "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones et al., Nature 321:522-525 (1986); Reichmann et al., Nature 332:323-329 (1988); and Presta, Curr. Op. Struct. Biol. 2:593-596 (1992).

As used herein, the term "hypervariable region" refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the $V_H$ (Chothia and Lesk J. Mol. Biol. 196: 901-917 (1987)).

As used herein, the terms "identical" or percent "identity", when used in the context of two or more nucleic acids or polypeptide sequences, refers to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual see, e.g., NCBI web site). Such sequences are then said to be "substantially identical." This term also refers to, or can be applied to, the complement of a test sequence. The term also includes sequences that have deletions and/or additions, as well as those that have substitutions. As described below, the algorithms can account for gaps and the like. In some embodiments, identity exists over a region that is at least about 25 amino acids or nucleotides in length, or 50-100 amino acids or nucleotides in length.

An "isolated" or "purified" polypeptide or biologically-active portion thereof is substantially free of cellular material or other contaminating polypeptides from the cell or tissue source from which the polypeptide is derived, or substantially free from chemical precursors or other chemicals when chemically synthesized. For example, an isolated anti-rabies antibody would be free of materials that would interfere with diagnostic or therapeutic uses of the agent. Such interfering materials may include enzymes, hormones and other proteinaceous and nonproteinaceous solutes. Alternatively, an isolated rabies glycoprotein, which is immunoreactive with an anti-rabies antibody of the present technology, would be substantially free of materials that would interfere with diagnostic or therapeutic uses of the polypeptide.

As used herein, the terms "immunologically cross-reactive" and "immunologically-reactive" are used interchangeably to mean an antigen which is specifically reactive with an antibody which was generated using the same ("immunologically-reactive") or different ("immunologically cross-reactive") antigen. Generally, the antigen is a rabies glycoprotein, a variant or subsequence thereof.

As used herein, the term "immunologically-reactive conditions" means conditions which allow an antibody, generated to a particular epitope of an antigen, to bind to that epitope to a detectably greater degree than the antibody binds to substantially all other epitopes, generally at least two times above background binding, or at least five times above background. Immunologically-reactive conditions are dependent upon the format of the antibody binding reaction and typically are those utilized in immunoassay protocols. See Harlow & Lane, Antibodies, A Laboratory Manual (Cold Spring Harbor Publications, New York, 1988) for a description of immunoassay formats and conditions.

As used herein, the term "medical condition" includes, but is not limited to, e.g, any condition or disease manifested as one or more physical and/or psychological symptoms for which treatment and/or prevention is desirable, and includes previously and newly identified diseases and other disorders. For example, a medical condition may be a rabies infection.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., Nature 256:495 (1975), or may be made by recombinant DNA methods (See, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example.

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well-known in the art. Such modifications are well described in basic texts and in more detailed monographs, as well as in a voluminous research literature. In a particular embodiment, the polypeptide contains polypeptide sequences from a rabies antibody protein.

As used herein, "post exposure prophylaxis" or "PEP" refers to a treatment regime that is indicated for persons possibly exposed to a rabid animal. Possible exposures include bite exposure (i.e., any penetration of the skin by teeth) including animal bites, and non-bite exposure. PEP typically comprises the administration of anti-rabies antibodies in conjunction with a rabies vaccine, such as purified chick embryo cell (PCEC) vaccine (RabAvert®, Novartis, Basel, Switzerland; Rabipur®, Chiron Behring GmbH & Co., Liederbach, Germany), human diploid cell vaccine (HDCV; Imovax®, Sanofi Pasteur, Swiftwater, Pa., USA), rabies vaccine adsorbed (RVA). PEP often includes the administration of human rabies immune globulin (HRIG), an anti-rabies gamma globulin concentrated from plasma of hyperimmunized human donors. BRIG is an immunizing agent typically administered to an individual following exposure to rabies virus.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed or not expressed at all.

As used herein, the term "specific binding" means the contact between an anti-rabies antibody and an antigen with a binding affinity of at least $10^{-6}$ M. In some embodiments, antibodies specifically bind with affinities of at least about $10^{-7}$ M, $10^{-8}$ M, $10^{-9}$ M, $10^{-10}$ M, $10^{-11}$ M, or $10^{-12}$ M.

As used herein, the term "subject" refers to a human or non-human animal, e.g., domestic animals (e.g., dogs, cats and the like), farm animals (e.g., cows, sheep, pigs, horses and the like), wild animals, (bats, raccoons, foxes, skunks, squirrels, chipmunks, mice, rabbits, and the like), and laboratory animals (e.g., monkey, rats, mice, rabbits, guinea pigs and the like).

As used herein, the term "substitution" is one of mutations that is generally used in the art. Those substitution variants have at least one amino acid residue in the anti-rabies antibody molecule replaced by a different residue. The sites of greatest interest for substitutional mutagenesis include the hypervariable regions, but FR alterations are also contemplated. Substitutions may be conservative, that is, one amino acid is replaced with one of similar shape and charge. Conservative substitutions are well-known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a non-polar or uncharged amino acid, and vice versa.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for rabies or a rabies-related disorder if, after receiving a therapeutic amount of rabies virus neutralizing antibody according to the methods of the present technology, the subject shows observable and/or measurable reduction in, or absence of, one or more signs and symptoms of the rabies infection/condition. It is also to be appreciated that the various modes of treatment or prevention of medical conditions as described are intended to mean "substantial", which includes total but also less than total treatment or prevention, and wherein some biologically or medically relevant result is achieved.

I. Compositions of the Present Technology

The present disclosure generally provides anti-rabies antibodies, which can bind to rabies glycoprotein and neutralize the infectivity of a rabies virus. The antibodies are useful for treating or preventing rabies infecting human and non-human subjects exposed to rabies virus. Accordingly, the various aspects of the present methods relate to the preparation, characterization, and manipulation of anti-rabies antibodies. Antibodies of the present technology are useful alone or in combination with rabies therapies known in the art for treating or preventing rabies infection. The present disclosure further relates to methods for administering anti-rabies antibodies of the present technology to a subject in need thereof.

The present disclosure encompasses anti-rabies antibodies that bind to rabies virus glycoprotein. In select embodiments, the antibodies comprise the antibodies summarized in Table 1.

TABLE 1

Anti-Rabies Antibodies

| Antibody | Type | Description |
|---|---|---|
| 3D11E3 | Murine Monoclonal Antibody | Binds to rabies glycoprotein epitope II |
| 3H10D3 | Murine Monoclonal Antibody | Binds to rabies glycoprotein epitope III |
| 5A1C10 | Murine Monoclonal Antibody | Binds to rabies glycoprotein epitope IV |
| 6F11C1 | Murine Monoclonal Antibody | Binds to rabies glycoprotein epitope I |
| 7G11A3 | Murine Monoclonal Antibody | Binds to rabies glycoprotein epitope I |

Deposits of biological materials of the present technology were made with the China General Microbiological Culture Collection Center (CGMCC), China Committee for Culture Collection of Microorganisms, P.O. Box 2714, Beijing 100080, The People's Republic of China as detailed in Table 2 below.

TABLE 2

Biological Deposits

| Name of Deposit | Materials | Date | Accession Number |
|---|---|---|---|
| RV3D11E31A9 | Mouse-mouse hybridoma | May 12, 2011 | CGMCC 4805 |
| RV7G11A32G11 | Mouse-mouse hybridoma | May 12, 2011 | CGMCC 4806 |
| RV5A1C103C4 | Mouse-mouse hybridoma | Nov. 10, 2011 | CGMCC 5471 |

The present technology includes antibodies that specifically bind epitopes which are conformational epitopes as well as nonconformational or linear epitopes. As noted above, conformational epitopes or nonconformational epitopes are distinguished in that the binding to the former but not the latter is lost in the presence of denaturing solvents.

Anti-rabies antibodies within the scope of the present technology include, e.g., but are not limited to, monoclonal, polyclonal, chimeric, humanized, diabody, and human monoclonal and human polyclonal antibodies which specifically bind the rabies glycoprotein, a homolog, derivative or a fragment thereof. Antibodies useful for the methods disclosed herein include, e.g., but are not limited to, IgG (including $IgG_1$, $IgG_2$, $IgG_3$, and $IgG_4$), IgA (including $IgA_1$ and $IgA_2$), IgD, IgE, or IgM, and IgY.

In one embodiment, the anti-rabies antibodies of the present technology bind specifically to rabies glycoprotein. In one embodiment, the antibodies are capable to reducing the infectivity of rabies virus and do not reduce the immunogenicity of a rabies vaccine. In select embodiments, the antibodies are monoclonal antibodies, murine antibodies, chimeric antibodies, or humanized antibodies.

In some embodiments, antibodies of the present technology comprise one or more heavy chain CDR amino acid sequences selected from the group consisting of DYIML (SEQ ID NO:57), DIYPYYGSTSYNLKFKG (SEQ ID NO:58), QGGDGNYVLFDY (SEQ ID NO:59), GFAMS (SEQ ID NO:60), TISSGGTYTYSPDSVMG (SEQ ID NO:61), RLRRNYYSMDY (SEQ ID NO:62), or a variant thereof having one or more conservative amino acid substitutions. In some embodiments, antibodies of the present technology comprise one or more light chain CDR amino acid sequences selected from the group consisting of KASQNVGTTVA (SEQ ID NO:63), SASYRYS (SEQ ID NO:64), QQYNSYPFT (SEQ ID NO:65), KSTKSLLNSDGFTYLD (SEQ ID NO:66), LVSNRFS (SEQ ID NO:67), FQSNYLPFT (SEQ ID NO:68), or a variant thereof having one or more conservative amino acid substitutions.

In some embodiments, the present technology comprises a nucleic acid encoding a rabies virus neutralizing antibody or fragment thereof. In some embodiments, the technology encompasses a host cell or nucleic acid encompassing the isolated nucleic acid encoding the antibody.

The present technology further includes antibodies which are anti-idiotypic to the antibodies of the present technology. The antibodies of the present technology can be monospecific, bispecific, trispecific or of greater multispecificity. Multispecific antibodies can be specific for different epitopes of the rabies glycoprotein or can be specific for both the rabies glycoprotein as well as for heterologous compositions, such as a heterologous polypeptide or solid support material. See, e.g., WO 93/17715; WO 92/08802; WO 91/00360; WO 92/05793; Tutt et al., *J. Immunol.* 147: 60-69 (1991); U.S. Pat. Nos. 5,573,920, 4,474,893, 5,601,819, 4,714,681, 4,925,648; 6,106,835; Kostelny et al., *J. Immunol.* 148: 1547-1553 (1992). The antibodies can be from any animal origin including birds and mammals. In some embodiments, the antibodies are human, murine, rabbit, goat, guinea pig, camel, horse, or chicken. In some embodiments, the antibodies are chimeric. In some embodiments, the antibodies are humanized.

The antibodies of the present technology can be used either alone or in combination with other compositions. For example, the rabies virus neutralizing antibodies can be used in combination with one or more anti-rabies therapies known in the art, such as those discussed above. Antibodies of the present technology may be administered to subject in need thereof prior to, subsequent to, or simultaneous to the administration of one or more additional rabies therapies, such as a rabies vaccine are included.

The antibodies of the present technology can further be recombinantly fused to a heterologous polypeptide at the N- or C-terminus or chemically conjugated (including covalently and non-covalently conjugations) to polypeptides or other compositions. For example, the antibodies can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

A. Methods of Preparing Anti-Rabies Antibodies of the Present Technology

The preparation of anti-rabies antibodies specific for rabies virus glycoprotein is illustrated in Example 1, infra. It should be understood that not only are naturally-occurring antibodies suitable for use in accordance with the present disclosure, recombinantly engineered antibodies and antibody fragments, e.g., antibody-related polypeptides, which are directed to rabies glycoprotein and fragments thereof are also suitable. Anti-rabies antibodies that can be subjected to the techniques set forth herein include monoclonal and polyclonal antibodies, and antibody fragments such as Fab, Fab', $F(ab')_2$, Fd, scFv, diabodies, antibody light chains, antibody heavy chains and/or antibody fragments. Methods useful for the high yield production of antibody Fv-containing polypeptides, e.g., Fab' and $F(ab')_2$ antibody fragments have been described. See U.S. Pat. No. 5,648,237.

Monoclonal Antibody.

In one embodiment of the present technology, the antibody is an anti-rabies monoclonal antibody. For example, in some embodiments, the anti-rabies monoclonal antibody may be a human or a mouse anti-rabies monoclonal antibody. For preparation of monoclonal antibodies directed towards a particular rabies glycoprotein, or derivatives, fragments, analogs or homologs thereof, any technique that provides for the production of antibody molecules by continuous cell line culture can be utilized. Such techniques include, but are not limited to, the hybridoma technique (See, e.g., Kohler & Milstein, 1975. Nature 256: 495-497); the trioma technique; the human B-cell hybridoma technique (See, e.g., Kozbor, et al., 1983. Immunol. Today 4: 72) and the EBV hybridoma technique to produce human monoclonal antibodies (See, e.g., Cole, et al., 1985. In: MONOCLONAL ANTIBODIES AND CANCER THERAPY, Alan R. Liss, Inc., pp. 77-96). Human monoclonal antibodies can be utilized in the practice of the present technology and can be produced by using human hybridomas (See, e.g., Cote, et al., 1983. Proc. Natl. Acad. Sci. USA 80: 2026-2030) or by transforming human B-cells with Epstein Barr Virus in vitro (See, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the rabies glycoprotein. Alternatively, hybridomas expressing anti-rabies monoclonal antibodies can be prepared by immunizing a subject and then isolating hybridomas from the subject's spleen using routine methods. See, e.g., Milstein et al., (Galfre and Milstein, *Methods Enzymol* (1981) 73: 3-46). Screening the hybridomas using standard methods will produce monoclonal antibodies of varying specificity (i.e., for different epitopes) and affinity. A selected monoclonal antibody with the desired properties, e.g., rabies binding, can be used as expressed by the hybridoma, it can be bound to a molecule such as polyethylene glycol (PEG) to alter its properties, or a cDNA encoding it can be isolated, sequenced and manipulated in various ways. Synthetic dendromeric trees can be added a reactive amino acid side chains, e.g., lysine to enhance the immunogenic properties of the rabies glycoprotein. Also, CPG-dinucleotide technique can be used to enhance the immunogenic properties of the rabies glycoprotein. Other manipulations include substituting or deleting particular amino acyl residues that contribute to instability of the antibody during storage or after administration to a subject, and affinity maturation techniques to improve affinity of the antibody of the rabies glycoprotein.

In one embodiment, the antibody of the present technology is an anti-rabies monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, N.Y., 349 (1988); Hammerling et al., *Monoclonal Antibodies And T-Cell Hybridomas,* 563-681 (1981). Other methods for producing hybridomas and monoclonal antibodies are well-known to those of skill in the art.

Phage Display Technique.

The antibodies of the present technology can be produced through the application of recombinant DNA and phage display technology. For example, anti-rabies antibodies, can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g., human or murine) by selecting directly with antigen, typically antigen bound or captured to a solid surface or bead. Phage used in these methods are typically filamentous phage including fd and M13 with Fab, Fv or disulfide stabilized Fv antibody domains are recombinantly fused to either the phage gene III or gene VIII protein. In addition, methods can be adapted for the construction of Fab expression libraries (See, e.g., Huse, et al., *Science* 246: 1275-1281, 1989) to allow rapid and effective identification of monoclonal Fab fragments with the desired specificity for a rabies virus polypeptide, e.g., a polypeptide or derivatives, fragments, analogs or homologs thereof. Other examples of phage display methods that can be used to make the antibodies of the present technology include those known in the art. Methods useful for displaying polypeptides on the surface of bacteriophage particles by attaching the polypeptides via disulfide bonds have been described by Lohning, U.S. Pat. No. 6,753,136. After phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and $F(ab')_2$ fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See, e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Anti Rabies Antibodies.

As noted above, the antibodies of the present technology can be produced through the application of recombinant DNA technology. Recombinant polynucleotide constructs encoding an anti-rabies antibody of the present technology typically include an expression control sequence operably-linked to the coding sequences of anti-rabies antibody chains, including naturally-associated or heterologous promoter regions. As such, another aspect of the technology includes vectors containing one or more nucleic acid sequences encoding an anti-rabies antibody of the present technology. For recombinant expression of one or more the polypeptides of the technology, the nucleic acid containing all or a portion of the nucleotide sequence encoding the anti-rabies antibody is inserted into an appropriate cloning vector, or an expression vector (i.e., a vector that contains the necessary elements for the transcription and translation of the inserted polypeptide coding sequence) by recombinant DNA techniques well-known in the art and as detailed below. Methods for producing diverse populations of vectors have been described by Lerner et al., U.S. Pat. Nos. 6,291,160; 6,680,192.

In general, expression vectors useful in recombinant DNA techniques are often in the form of plasmids. In the present specification, "plasmid" and "vector" can be used interchangeably as the plasmid is the most commonly used form of vector. However, the present technology is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression in that subject of a compound. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the anti-rabies antibody, and the collection and purification of the anti-rabies antibody, e.g., cross-reacting anti-rabies antibodies. See generally, U.S. Application No. 20020199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments.

The recombinant expression vectors of the present technology comprise a nucleic acid encoding a compound with rabies binding properties in a form suitable for expression of the nucleic acid in a host cell, which means that the recombinant expression vectors include one or more regulatory sequences, selected on the basis of the host cells to be used for expression that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., anti-rabies antibody), include, e.g., but are not limited to, 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding an anti-rabies antibody of the present technology is operably-linked to an ara B promoter and expressible in a host cell. See U.S. Pat. No. 5,028,530. The expression vectors of the present technology can be introduced into host cells to thereby produce polypeptides or peptides, including fusion polypeptides, encoded by nucleic acids as described herein (e.g., anti-rabies antibody, etc.).

Another aspect of the present technology pertains to anti-rabies antibody-expressing host cells, which contain a nucleic acid encoding one or more anti-rabies antibodies. The recombinant expression vectors of the present technology can be designed for expression of an anti-rabies antibody in prokaryotic or eukaryotic cells. For example, an anti-rabies antibody can be expressed in bacterial cells such as *Escherichia coli*, insect cells (using baculovirus expression vectors), fungal cells, e.g., yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g., using T7 promoter regulatory sequences and T7 polymerase. Methods useful for the preparation screening of polypeptides having predetermined property, e.g., anti-rabies antibody, via expression of stochastically generated polynucleotide sequences has been described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) Gene 69: 301-315) and pET 11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., an anti-rabies antibody, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (See, e.g., Wada, et al., 1992. Nucl. Acids Res. 20: 2111-2118). Such alteration of nucleic acid sequences of the present technology can be carried out by standard DNA synthesis techniques.

In another embodiment, the anti-rabies antibody expression vector is a yeast expression vector. Examples of vectors for expression in yeast *Saccharomyces cerevisiae* include pYepSec1 (Baldari, et al., 1987. EMBO J. 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif.), and picZ (Invitrogen Corp, San Diego, Calif.). Alternatively, an anti-rabies antibody can be expressed in insect cells using baculovirus expression vectors. Baculovirus vectors available for expression of polypeptides, e.g., anti-rabies antibody, in cultured insect cells (e.g., SF9 cells) include the pAc series (Smith, et al., *Mot Cell. Biol.* 3: 2156-2165, 1983) and the pVL series (Lucklow and Summers, 1989. *Virology* 170: 31-39).

In yet another embodiment, a nucleic acid encoding an anti-rabies antibody of the present technology is expressed in mammalian cells using a mammalian expression vector. Examples of mammalian expression vectors include, e.g., but are not limited to, pCDM8 (See. *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells useful for expression of the anti-rabies antibody of the present technology. See, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), in particular promoters of T cell receptors (Winoto and Baltimore, EMBO J. 8: 729-733, 1989) and immunoglobulins (Banerji, et al., 1983. *Cell* 33: 729-740; Queen and Baltimore, *Cell* 33: 741-748, 1983.), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Another aspect of the present methods pertains to host cells into which a recombinant expression vector of the present technology has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an anti-rabies antibody can be expressed in bacterial cells such as *E. coli*, insect cells, yeast or mammalian cells. Mammalian cells are a suitable host for expressing nucleotide segments encoding immunoglobulins or fragments thereof. See Winnacker, *From Genes To Clones*, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. In some embodiments, the cells are nonhuman. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Illustrative expression control sequences are promoters derived from endogenous genes, cytomegalovirus, SV40, adenovirus, bovine papillomavirus, and the like. Co et al., *J Immunol.* 148: 1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation, biolistics or viral-based transfection can be used for other cellular hosts. Other methods used to transform mammalian cells include the use of polybrene, protoplast fusion, liposomes, electroporation, and microinjection (See generally, Sambrook et al., *Molecular Cloning*). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well-known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the anti-rabies antibody or can be introduced on a separate vector. Cells stably transfected with the introduced nucleic acid can be identified by drug selection (e.g., cells that have incorporated the selectable marker gene will survive, while the other cells die).

A host cell that includes an anti-rabies antibody of the present technology, such as a prokaryotic or eukaryotic host cell in culture, can be used to produce (i.e., express) recombinant anti-rabies antibody. In one embodiment, the method comprises culturing the host cell (into which a recombinant expression vector encoding the anti-rabies antibody has been introduced) in a suitable medium such that the anti-rabies antibody is produced. In another embodiment, the method further comprises the step of isolating the anti-rabies antibody from the medium or the host cell. Once expressed, collections of the anti-rabies antibody, e.g., the anti-rabies antibodies or the anti-rabies antibody-related polypeptides are purified from culture media and host cells. The anti-rabies antibody can be purified according to standard procedures of the art, including HPLC purification, column chromatography, gel electrophoresis and the like. In one embodiment, the anti-rabies antibody is produced in a host organism by the method of Boss et al., U.S. Pat. No. 4,816,397. Usually, anti-rabies antibody chains are expressed with signal sequences and are thus released to the culture media. However, if the anti-rabies antibody chains are not naturally secreted by host cells, the anti-rabies antibody chains can be released by treatment with mild detergent. Purification of recombinant polypeptides is well-known in the art and include ammonium sulfate precipitation, affinity chromatography purification technique, column chromatography, ion exchange purification technique, gel electrophoresis and the like (See generally Scopes, Protein Purification (Springer-Verlag, N.Y., 1982).

Polynucleotides encoding anti-rabies antibodies, e.g., the anti-rabies antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Due to the degeneracy of nucleic acid coding sequences, other sequences which encode substantially the same amino acid sequences as those of the naturally occurring proteins may be used in the practice of the present technology. These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present technology tolerates sequence homology variations of up to 25% as calculated by standard methods ("Current Methods in Sequence Comparison and Analysis," Macromolecule Sequencing and Synthesis, Selected Methods and Applications, pp. 127-149, 1998, Alan R. Liss, Inc.) so long as such a variant forms an operative antibody which recognizes rabies or rabies-like glycoproteins. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present technology are proteins or fragments or derivatives thereof which are differentially modified during or after translation, e.g., by glycosylation, proteolytic cleavage, linkage to an antibody molecule or other cellular ligands, etc. Any technique for mutagenesis known in the art can be used, including but not limited to in vitro site directed mutagenesis, *J. Biol. Chem.* 253:6551, use of Tab linkers (Pharmacia), and the like.

Single Chain Antibodies.

In one embodiment, the anti-rabies antibody of the present technology is a single chain anti-rabies antibody. According to the present technology, techniques can be adapted for the production of single-chain antibodies specific to a rabies glycoprotein (See, e.g., U.S. Pat. No. 4,946,778). Examples of techniques which can be used to produce single-chain Fvs and antibodies of the present technology include those described in U.S. Pat. Nos. 4,946,778 and 5,258,498; Huston et al., *Methods in Enzymology*, 203: 46-88, 1991; Shu, L. et al., *Proc. Natl. Acad. Sci. USA*, 90: 7995-7999, 1993; and Skerra et al., *Science* 240: 1038-1040, 1988.

Chimeric and Humanized Antibodies.

In one embodiment, the anti-rabies antibody of the present technology is a chimeric anti-rabies antibody. In one embodiment, the anti-rabies antibody of the present technology is a humanized anti-rabies antibody. In one embodiment of the present technology, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-rabies antibodies, such as chimeric and humanized monoclonal antibodies, comprising both human and non-human portions, can be made using standard recombinant DNA techniques, and are within the scope of the present technology. For some uses, including in vivo use of the anti-rabies antibody of the present technology in humans as well as use of these agents in vitro detection assays, it is possible to use chimeric, humanized, or human anti-rabies antibodies. Such chimeric and humanized monoclonal antibodies can be produced by recombinant DNA techniques known in the art.

In one embodiment, the present technology allows the construction of humanized anti-rabies antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present technology provides for a humanized anti-rabies antibodies, heavy and light chain immunoglobulins.

CDR Antibodies.

In one embodiment, the anti-rabies antibody of the present technology is an anti-rabies CDR antibody. Generally the donor and acceptor antibodies used to generate the anti-rabies CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently all three CDRs in all variable domains of the acceptor antibody will be replaced with the corresponding donor CDRs, though one need replace only as many as necessary to permit adequate binding of the resulting CDR-grafted antibody to MetAp3. Methods for generating CDR-grafted and humanized antibodies are taught by Queen et al. U.S. Pat. No. 5,585,089, U.S. Pat. No. 5,693,761; U.S. Pat. No. 5,693,762; and Winter U.S. Pat. No. 5,225,539; and EP 0682040. Methods useful to prepare $V_H$ and $V_L$ polypeptides are taught by Winter et al., U.S. Pat. Nos. 4,816,397; 6,291,158; 6,291,159; 6,291,161; 6,545,142; EP 0368684; EP0451216; EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-rabies CDR grafted antibody by replacing certain residues of a given FR to make the FR more similar to the corresponding FR of the donor antibody. Suitable locations of the substitutions include amino acid residues adjacent to the CDR, or which are capable of interacting with a CDR (See, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-rabies CDR antibody significantly compared to the same antibody with a fully human FR.

Fusion Proteins.

In one embodiment, the anti-rabies antibody of the present technology is a fusion protein. The anti-rabies antibodies of the present technology, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present technology can also be engineered to improve characteristics of the anti-rabies antibodies. For instance, a region of additional amino acids, particularly charged amino acids, can be added to the N-terminus of the anti-rabies antibody to improve stability and persistence during purification from the host cell or subsequent handling and storage. Also, peptide moieties can be added to an anti-rabies antibody to facilitate purification. Such regions can be removed prior to final preparation of the anti-rabies antibody. The addition of peptide moieties to facilitate handling of polypeptides are familiar and routine techniques in the art. The anti-rabies antibody of the present technology can be fused to marker sequences, such as a peptide which facilitates purification of the fused polypeptide. In select embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., *Cell* 37: 767, 1984. Thus, any of these above fusions can be engineered using the polynucleotides or the polypeptides of the present technology. Also, the fusion protein can show an increased half-life in vivo.

Fusion proteins having disulfide-linked dimeric structures (due to the IgG) can be more efficient in binding and neutralizing other molecules, than the monomeric secreted protein or protein fragment alone. Fountoulakis et al., *J. Biochem.* 270: 3958-3964, 1995.

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, e.g., improved pharmacokinetic properties. See EP-A 0232 262. Alternatively, deleting the Fc part after the fusion protein has been expressed, detected, and purified, would be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8: 52-58, 1995; Johanson et al., *J. Biol. Chem.,* 270: 9459-9471, 1995.

Labeled Anti Rabies Antibodies.

In one embodiment, the anti-rabies antibody of the present technology is coupled with a label moiety, i.e., detectable group. The particular label or detectable group conjugated to the anti-rabies antibody is not a critical aspect of the technology, so long as it does not significantly interfere with the specific binding of the anti-rabies antibody of the present technology to the rabies glycoprotein or the rabies-like glycoprotein. The detectable group can be any material having a detectable physical or chemical property. Such detectable labels have been well-developed in the field of immunoassays and imaging, in general, most any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^{3}H$, $^{14}C$, $^{35}S$, $^{125}I$, $^{121}I$, $^{131}I$, $^{112}In$, $^{99}mTc$), other imaging agents such as microbubbles (for ultrasound imaging), $^{18}F$, $^{11}C$, $^{15}O$, (for Positron emission tomography), $^{99m}TC$, $^{111}In$ (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that described the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals ($6^{th}$ Ed., Molecular Probes, Inc., Eugene Oreg.).

The label can be coupled directly or indirectly to the desired component of an assay according to methods well-known in the art. As indicated above, a wide variety of labels can be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-rabies antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labeling moieties, include, but are not limited to, e.g., luciferin, and 2,3-dihydrophthalazinediones, e.g., luminol. For a review of various labeling or signal-producing systems which can be used, see U.S. Pat. No. 4,391,904.

Means of detecting labels are well-known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-rabies antibodies. In this case, antigen-coated particles are agglutinated by samples comprising the target antibodies. In this format, none of the components need be labeled and the presence of the target antibody is detected by simple visual inspection.

B. Identifying and Characterizing the Anti-Rabies Antibodies of the Present Technology Methods useful to identify and screen antibodies against rabies and rabies-related polypeptides for those that possess the desired specificity to a rabies glycoprotein include any immunologically-mediated techniques known within the art. Components of an immune response can be detected in vitro by various methods that are well-known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A; et al., *Immunity,* 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.,* 86: 4230-4, 1989); (4) mast cells can be incubated with reagents that cross-link their Fc-epsilon receptors and histamine release measured by enzyme immunoassay (Siraganian et al., *TIPS,* 4: 432-437, 1983); and (5) enzyme-linked immunosorbent assay (ELISA).

Similarly, products of an immune response in either a model organism (e.g., mouse) or a human subject can also be detected by various methods that are well-known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72: 1310-5, 1988); (3) the proliferation of peripheral blood mononuclear cells (PBMCs) in response to mitogens or mixed lymphocyte reaction can be measured using $^3$H-thymidine; (4) the phagocytic capacity of granulocytes, macrophages, and other phagocytes in PBMCs can be measured by placing PBMCs in wells together with labeled particles (Peters et al., *Blood,* 72: 1310-5, 1988); and (5) the differentiation of immune system cells can be measured by labeling PBMCs with antibodies to CD molecules such as CD4 and CD8 and measuring the fraction of the PBMCs expressing these markers.

In one embodiment, anti-rabies antibodies of the present technology are selected using display of rabies peptides on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. No. 5,871,907; U.S. Pat. No. 5,969,108; U.S. Pat. No. 6,225,447; U.S. Pat. No. 6,291,650; U.S. Pat. No. 6,492,160.

In one embodiment, anti-rabies antibodies of the present technology are selected using display of rabies peptides on the surface of a yeast host cell. Methods useful for the isolation of scFv polypeptides by yeast surface display have been described by Kieke et al., *Protein Eng.* 1997 November; 10(11): 1303-10.

In one embodiment, anti-rabies antibodies of the present technology are selected using ribosome display. Methods useful for identifying ligands in peptide libraries using ribosome display have been described by Mattheakis et al., *Proc. Natl. Acad. Sci. USA* 91: 9022-26, 1994; and Hanes et al., *Proc. Natl. Acad. Sci. USA* 94: 4937-42, 1997.

In one embodiment, anti-rabies antibodies of the present technology are selected using tRNA display of rabies peptides. Methods useful for in vitro selection of ligands using tRNA display have been described by Merryman et al., *Chem. Biol.,* 9: 741-46, 2002.

In one embodiment, anti-rabies antibodies of the present technology are selected using RNA display. Methods useful for selecting peptides and proteins using RNA display libraries have been described by Roberts et al. *Proc. Natl. Acad. Sci. USA,* 94: 12297-302, 1997; and Nemoto et al., *FEBS Lett.,* 414: 405-8, 1997. Methods useful for selecting peptides and proteins using unnatural RNA display libraries have been described by Frankel et al., *Curr. Opin. Struct. Biol.,* 13: 506-12, 2003.

In one embodiment, anti-rabies antibodies of the present technology are expressed in the periplasm of gram negative bacteria and mixed with labeled rabies glycoprotein. See WO 02/34886. In clones expressing recombinant polypeptides with affinity for the rabies glycoprotein, the concentration of the labeled rabies glycoprotein bound to the anti-rabies antibodies is increased and allows the cells to be isolated from the rest of the library as described in Harvey et al., *Proc. Natl. Acad. Sci.* 22: 9193-98 2004 and U.S. Pat. Publication No. 2004/0058403.

After selection of the desired anti-rabies antibodies, it is contemplated that it can be produced in large volume by any technique known to those skilled in the art, e.g., prokaryotic or eukaryotic cell expression and the like. The anti-rabies antibodies which are, e.g., but not limited to, anti-rabies hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of Rabies Virus Binding.

In one embodiment, a rabies binding assay refers to an assay format wherein a rabies glycoprotein and an anti-rabies antibody are mixed under conditions suitable for binding between the rabies or rabies-like glycoprotein and the anti-rabies antibody and assessing the amount of binding between the rabies or rabies-like glycoprotein and the anti-rabies antibody. The amount of binding is compared with a suitable control, which can be the amount of binding in the absence of the rabies glycoprotein, the amount of the binding in the presence of non-specific immunoglobulin composition, or both. The amount of binding can be assessed by any suitable method. Binding assay methods include, e.g., ELISA, radioimmunoassays, scintillation proximity assays, fluorescence energy transfer assays, liquid chromatography, membrane filtration assays, and the like. Biophysical assays for the direct measurement of rabies glycoprotein binding to anti-rabies antibody are, e.g., nuclear magnetic resonance, fluorescence, fluorescence polarization, surface plasmon resonance (BIA-COR chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate anti-rabies antibody is at least 1 percent greater than the binding observed in the absence of the candidate anti-rabies antibody, the candidate anti-rabies antibody is useful as an anti-rabies antibody of the present technology.

Co-crystals of the rabies glycoproteins and the anti-rabies antibodies are also provided by the present technology as a method of determining molecular interactions. Conditions suitable for binding between an anti-rabies antibody and a rabies glycoprotein will depend on the compound and its ligand and can be readily determined by one of ordinary skill in the art.

Measurement of Rabies Virus Neutralization.

As used here, "rabies virus neutralization" refers to reduction of the infectivity of rabies virus through the binding of an anti-rabies antibody. The capacity of anti-rabies antibodies of the present technology to neutralize a rabies virus may be assessed in vitro or in vivo using methods known in the art. Illustrative in vitro methods include the rapid fluorescent focus inhibition test (RFFIT), as described in Smith et al., "A rapid fluorescent focus inhibition test (RFFIT) for determining rabies virus-neutralizing antibody," in: Meslin F-X, Kaplan M M, Koprowski H, eds. Laboratory techniques in rabies. 4th ed. Geneva, Switzerland:World Health Organization 1996; 181-192. Illustrative in vivo methods include but are not limited to mouse neutralization test (MNT), such as described in Hasse, et al., 13(2) J. Biol. Stand. 123-28 (1985). Illustrative results of RFFIT and MNT are shown in the Examples, infra. In some embodiments, the infectivity of the rabies virus is neutralized at least 5%, at least 10%, at least 15%, at least 25%, at least 50%, at least 60%, at least 75%, at least 85%, at least 90%, at least 95%, at least 99%, at least 99.5%, at least 99.9%, or at least 100%.

Measurement of Rabies Vaccine Interference.

The anti-rabies antibodies of the present technology have the capacity to neutralize rabies virus in a subject in need thereof, without interfering with the efficacy of a rabies vaccine. This aspect of the present technology is of particular value because typical rabies therapies comprise the co-administration of rabies vaccines and antibodies. The degree to which an anti-rabies antibody interferes with the efficacy of a rabies vaccine may be assessed using methods known in the art, such as those demonstrated in the Examples, infra. Briefly, rabies vaccine may be administered to animal subjects in conjunction with or in the absence of anti-rabies antibodies. Following a period of time sufficient for the vaccine to elicit an immune response in the subjects, vaccine-specific titers of subjects administered the vaccine alone are compared to those of subjects administered the vaccine in conjunction with the antibody. The degree to which an anti-rabies antibody interferes with the efficacy of the vaccine is reflected in a reduced vaccine-specific antibody titer. Illustrative results of such an experiment are shown in the Examples, infra. In some embodiments, the antibody interferes with the immune response induced by the rabies vaccine less than 0.1%, less than 0.5%, less than 1%, less than 2%, less than 5%, less than 10%, less than 20%, less than 25%, less than 50%, or less than 75% compared to a control subject that was administered the vaccine but not administered the antibody.

Measurement of Post-Exposure Prophylaxis.

Anti-rabies antibodies may be evaluated for post-exposure prophylaxis in subjects exposed to rabies virus using methods known in the art such as those demonstrated in the Examples, infra. Briefly, animal subjects exposed to rabies virus may be administered one or more candidate anti-rabies antibodies as a component of post-exposure treatment. The antibody may be administered alone or in conjunction with known rabies therapies such as a vaccine. After a period of time sufficient for rabies infection to ensue, the survival rate of subjects administered the antibody is compared to appropriate controls, in which no candidate antibodies were administered. Reduction in rabies virus infectivity is reflected by an increased rate or length of time of survival of subjects administered the candidate antibody as compared to controls. Illustrative results of such experiments are shown in the Examples, infra.

II. Uses of the Anti-Rabies Antibodies of the Present Technology

A. Diagnostic Uses of Anti-Rabies Antibodies

The anti-rabies antibodies of the present technology are useful in diagnostic methods. As such, the present technology provides methods using the antibodies in the diagnosis of rabies infection in a subject. Anti-rabies antibodies of the present technology may be selected such that they have any level of epitope binding specificity and very high binding affinity to a rabies glycoprotein. In general, the higher the binding affinity of an antibody the more stringent wash conditions can be performed in an immunoassay to remove non-specifically bound material without removing target polypeptide. Accordingly, anti-rabies antibodies of the present technology useful in diagnostic assays usually have binding affinities of at least $10^8$, $10^9$, $10^{10}$, $10^{11}$ or $10^{12}$ M. Further, it is desirable that anti-rabies antibodies used as diagnostic reagents have a sufficient kinetic on-rate to reach equilibrium under standard conditions in at least 12 h, at least five (5) h, or at least one (1) hour.

Anti-rabies antibodies can be used to detect an immunoreactive rabies or an immunoreactive rabies-like glycoprotein in a variety of standard assay formats. Such formats include immunoprecipitation, Western blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject.

B. Prophylactic and Therapeutic Use of Anti-Rabies Antibodies

The anti-rabies antibodies of the present technology are useful in post-exposure prophylaxis (PEP) therapy for subjects exposed to rabies virus. Possible exposures include bite exposure (i.e., any penetration of the skin by teeth) including animal bites, and non-bite exposure. Non-bite exposure includes contact with infected animals or animal products, such as but not limited to hair, e.g., blood, tissue, urine, feces, and saliva. PEP therapy typically comprises the administration of anti-rabies antibodies to a subject in need thereof in combination with a rabies vaccine.

The compositions of the present technology may be employed in conjunction with other molecules useful in prophylaxis and/or treatment of rabies exposure or infection. For example, they may be co-administered with one or more vaccines against rabies virus. Alternatively, the antibodies of the present technology may be administered before or after the one or more vaccines. The antibodies may be administered in conjunction with rabies vaccines, including but not limited to, e.g., purified chick embryo cell vaccine (PCECV; RabAvert®, Novartis, Basel, Switzerland; Rabipur®, Chiron Behring GmbH & Co., Liederbach, Germany), human diploid cell vaccine (HDCV; Imovax®, Sanofi Pasteur, Swiftwater, Pa., USA), and rabies vaccine adsorbed (RVA). Additionally or alternatively, the compositions of the present technology may further be administered in conjunction with human rabies immune globulin (BRIG) or equine rabies immune globulin (ERIG).

The compositions of the present technology may optionally be administered as a single bolus to a subject in need thereof. Alternatively, the dosing regimen may comprise multiple administrations performed at various times post-exposure. For example, the dosing regimen may comprise five doses of rabies vaccine intramuscularly and/or intraperitoneally on days 0, 3, 7, 14 and 28 after exposure. The site of administration may vary relative to the site of rabies exposure. For example, compositions of the present technology may be administered into and around the wounds on day 0 or otherwise as soon as possible after exposure, with the remaining volume given intramuscularly at a site distant from the site. Alternatively, all of the composition may be administered at a site distant to the site of exposure. Compositions of the present technology may be administered at the same site or a different site as administration of a rabies vaccine.

Administration can be carried out by any suitable route, including orally, intranasally, parenterally (intravenously, intramuscularly, intraperitoneally, or subcutaneously), rectally, intracranially, intrathecally, or topically. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

In some embodiments, antibodies of the present technology comprise pharmaceutical formulations which may be administered to subjects in need thereof in one or more doses. Dosage regimens can be adjusted to provide the desired response (e.g., a therapeutic response or a prophylactic response).

Typically, an effective amount of the compositions of the present technology, sufficient for achieving a therapeutic or prophylactic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For administration of anti-rabies antibodies, the dosage ranges from about 0.0001 to 100 mg/kg, and more usually 0.01 to 5 mg/kg every week, every two weeks or every three weeks, of the host body weight. For example dosages can be 1 mg/kg body weight or 10 mg/kg body weight every week, every two weeks or every three weeks or within the range of 1-10 mg/kg every week, every two weeks or every three weeks. In one embodiment, a single dosage of antibody range from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Anti-rabies antibodies may be administered on multiple occasions. Intervals between single dosages can be hourly, daily, weekly, monthly or yearly. Intervals can also be irregular as indicated by measuring blood levels of antibody in the subject. In some methods, dosage is adjusted to achieve a serum antibody concentration in the subject of from about 75 μg/mL to about 125 μg/mL, 100 μg/mL to about 150 μg/mL, from about 125 μg/mL to about 175 μg/mL, or from about 150 μg/mL to about 200 μg/mL. Alternatively, anti-rabies antibodies can be administered as a sustained release formulation, in which case less frequent administration is required. Dosage and frequency vary depending on the half-life of the antibody in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, or until the subject shows partial or complete amelioration of symptoms of disease. Thereafter, the patent can be administered a prophylactic regime.

Toxicity.

Optimally, an effective amount (e.g., dose) of anti-rabies antibody described herein will provide therapeutic benefit without causing substantial toxicity to the subject. Toxicity of the anti-rabies antibody described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the anti-rabies antibody described herein lies within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

Formulations of Pharmaceutical Compositions.

According to the methods of the present technology, the anti-rabies antibody can be incorporated into pharmaceutical compositions suitable for administration. The pharmaceutical compositions generally comprise recombinant or substantially purified native antibody and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the composition are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the anti-rabies antibody, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. The anti-rabies antibody named in this technology can be present in unsalified or unesterified form, or in salified and/or esterified form, and the naming of such anti-rabies antibody is intended to include both the original (unsalified and unesterified) compound and its pharmaceutically-acceptable salts and esters. Also, certain embodiments of the present technology can be present in more than one stereoisomeric form, and the naming of such anti-rabies antibody is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present technology.

Examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well-known in the art. Except insofar as any conventional media or compound is incompatible with the anti-rabies antibody, use thereof in the compositions is contemplated. Supplementary active compounds can also be incorporated into the compositions.

A pharmaceutical composition of the present technology is formulated to be compatible with its intended route of administration. The anti-rabies antibody compositions of the present technology can be administered by parenteral, topical, intravenous, oral, subcutaneous, intraarterial, intradermal, transdermal, rectal, intracranial, intrathecal, intraperitoneal, intranasal; or intramuscular routes, or as inhalants. The anti-rabies antibody can optionally be administered in combination with other agents that are at least partly effective in treating various diseases including various actin- or microfilament-related diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be desirable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the anti-rabies antibody in the required amount in an appropriate solvent with one or a combination of ingredients enumerated above, as required, followed by filtered sterilization. Generally, dispersions are prepared by incorporating the anti-rabies antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The antibodies of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the anti-rabies antibody can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the anti-rabies antibody is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the anti-rabies antibody is formulated into ointments, salves, gels, or creams as generally known in the art.

The anti-rabies antibody can also be prepared as pharmaceutical compositions in the form of suppositories (e.g., with conventional suppository bases such as cocoa butter and other glycerides) or retention enemas for rectal delivery.

In one embodiment, the anti-rabies antibody is prepared with carriers that will protect the anti-rabies antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

C. Kits

The present technology provides kits for the diagnosis, prophylaxis, and/or treatment of rabies infection, comprising at least one antibody of the present technology, or a functional variant thereof. Optionally, the above described components of the kits of the present technology are packed in suitable containers and labeled for diagnosis, prophylaxis, and/or treatment rabies. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic, prophylactic or diagnostic products, that contain information about, for example, the indications, usage, dosage, manufacture, administration, contraindications and/or warnings concerning the use of such therapeutic, prophylactic or diagnostic products.

The kits are useful for detecting the presence of an immunoreactive rabies glycoprotein or an immunoreactive rabies-like glycoprotein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more anti-rabies antibodies capable of binding a rabies glycoprotein or a rabies-like glycoprotein in a biological sample (e.g., an antibody or antigen-binding fragment thereof having the same antigen-binding specificity of antibodies produced by a deposited cell line selected from the group consisting of: CGMCC Accession Nos: 4805 and 4806); means for determining the amount of the rabies glycoprotein or rabies-like glycoprotein in the sample; and means for comparing the amount of the immunoreactive rabies glycoprotein or the immunoreactive rabies-like glycoprotein in the sample with a standard. One or more of the anti-rabies antibodies may be labeled. The kit components, (e.g., reagents) can be packaged in a suitable container. The kit can further comprise instructions for using the kit to detect the immunoreactive rabies glycoprotein or the rabies-like glycoprotein.

For antibody-based kits, the kit can comprise, e.g., 1) a first antibody, e.g., attached to a solid support, which binds to a rabies glycoprotein corresponding to the present technology; and, optionally; 2) a second, different antibody which binds to either the rabies glycoprotein or to the first antibody and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a rabies virus glycoprotein in vitro or in vivo, or for treatment or prevention of rabies infection in an individual in need thereof. In several embodiments, the use of the reagents can be according to the methods of the present technology.

EXAMPLES

The following EXAMPLES are presented in order to more fully illustrate the select embodiments of the present technology. These EXAMPLES should in no way be construed as limiting the scope of the present technology, as defined by the appended claims.

The following examples demonstrate the preparation, characterization, and use of illustrative anti-rabies antibodies of the present technology. Example 1 describes the preparation of murine monoclonal antibodies. Examples 2-7 demonstrate the specificity of the illustrative antibodies for rabies virus glycoprotein, the capacity of the antibodies to neutralize rabies virus, competition among the antibodies for binding to rabies virus glycoprotein, the degree to which the antibodies effect the immunogenicity of a rabies vaccine, and the capacity of a combination of the antibodies to neutralize rabies virus. Examples 8-15 demonstrate the production of chimeric and humanized versions of two of the illustrative antibodies, and characterization of their binding specificities, capacities to neutralize rabies virus, and use in post-exposure protection against rabies virus infection.

Example 1

Preparation and Characterization of Murine Rabies Virus Neutralizing Antibodies

The murine rabies virus neutralizing antibodies may be obtained by culturing a hybridoma which, in turn, may be obtained by immunizing a mouse with rabies glycoprotein and subsequently fusing the spleen cells or lymph node cells from the mouse with mouse myeloma cells. The procedure for the preparation of the anti-rabies antibodies is detailed below with reference to the above described steps. This method for preparing an antibody of the present invention is intended only to be illustrative of the methods of preparation and is not limited thereto. Other known procedures may be followed.

The present technology utilizes a rabies girus glycoprotein (GenBank Accession No. ABY1950) as an immunogen to induce an antibody capable of neutralizing rabies virus. The immunogen prepared is mixed with an adjuvant, such as Freund's complete or incomplete adjuvant and administered to a mouse. Suitable administration routes to immunize an experimental animal include the subcutaneous, intraperitoneal, intravenous, intradermal, and intramuscular injections, with subcutaneous and intraperitoneal injections being preferred. Immunizations are optionally performed by a single dose or, by several repeated doses at appropriate intervals. The antibody production of immunized animals is determined by serum levels of an antigen-specific antibody. When high titers of antibody is achieved, animals can be used as a source for preparation of antibody-producing cells. In general, the antibody-producing cells may be collected at 3-5 days after the last injection with an immunogen.

Lymphocytes and plasma cells obtained from any suitable part of the animal are precursor cells to produce the antibody. Lymphocyte or plasma cell sources include spleen, lymph nodes, peripheral blood, or any appropriate combination thereof, with spleen cells being the most common source. After the last booster injection, single lymphocyte suspension is prepared from lymphoid tissue in which antibody producing cells are present. The fusion technique includes washing spleen and myeloma cells with serum-free medium (such as RPMI 1640) or phosphate buffered saline (hereinafter referred to as "PBS") so that the number ratio of spleen cells to myeloma cells is approximately between 5:1 and 10:1, and then centrifuged. After the supernatant has been discarded and the pelleted cells sufficiently loosened, 1 ml of serum-free medium containing 50%(w/v) polyethylene glycol (m.w. 1,000 to 4,000) is added dropwise with mixing. Subsequently, 10 ml of serum-free medium is slowly added and then centrifuged. The supernatant is discarded again, and the pelleted cells are suspended in an appropriate amount of HAT medium containing a solution of hypoxanthine, aminopterin and thymidine (hereinafter referred to as "HAT").

Cells from established mouse cell lines serve as the source of myeloma cells for fusion, including P3X63Ag8U.1 (P3-U1), P3/NSI/1-Ag4-1(NS-1), SP2/0-Ag14 (SP-2), P3X63Ag8.653 and P3X63Ag8 (X63), which can be acquired from ATCC. The cell line selected is serially transferred into an appropriate medium, such as 8-azaguanine medium. 8-azaguanine medium includes Iscove's Modified Dulbecco's Medium (hereinafter referred to as "IMDM") or Dulbecco's, Modified Eagle Medium (hereinafter referred to as "DMEM"). RPMI-1640 medium supplemented with glutamine, 2-mercaptoethanol, gentamicin, fetal calf serum (hereinafter referred to as "FCS"), and 8-azaguanine.

After fusion, any unfused myeloma cells and any myeloma-myeloma fusions are unable to survive in HAT medium. On the other hand, fusions of antibody producing cells with each other, as well as hybridomas of antibody producing cells with myeloma cells can survive, the former only having a limited life. Accordingly, continued incubation in HAT medium results in selection of only the desired hybridomas. The resulting hybridomas grow into colonies that are then transferred into HAT medium lacking aminopterin (HT medium). Thereafter, aliquots of the culture supernatant are removed to determine antibody titer by, for example, ELISA. Hybridomas which have been shown to produce specific antibodies are then transferred to another plate for cloning.

The mouse-mouse hybridomas RV3D11E31A9 and RV7G11A32G11, which are a basis for antibodies of the present technology, were deposited with CGMCC on May 12, 2011, and have the accession numbers CGMCC 4805 and 4806, respectively.

After obtaining stable antibody-producing hybridoma, culture of selected hybridoma may be expanded. The supernatant from the large-scale culture is then harvested and purified by a suitable method, such as affinity chromatography and gel filtration. The hybridoma may also be grown intraperitoneally in a syngeneic mouse, such as a BALB/c mouse or a nu/nu mouse, to obtain ascites containing an anti-rabies monoclonal antibody in large quantities.

Example 2

Binding Activity of Murine Rabies Virus Neutralizing Antibodies

The binding activity of five rabies virus neutralizing antibodies (RVNAs) to rabies virus RV glycoprotein was studied in this Example. The murine RVNAs and other biological materials used in Examples 1-6 are shown in Table 3. Animals used in these studies included BALB/c mice, female, 6~8 weeks, weighing 20 to 30 grams, SPF grade and Syrian hamsters, 2~3 months, weighing 100 grams, SPF grade.

TABLE 3

Bioreagents

| Category | Name | Con. (mg/ml) | Manufacturer |
|---|---|---|---|
| Anti-rabies antibody | 3D11E3 | 2.15 | See Example 1 |
| Anti-rabies antibody | 3H10D3 | 0.88 | See Example 1 |
| Anti-rabies antibody | 5A1C10 | 1.38 | See Example 1 |
| Anti-rabies antibody | 6F11C1 | 2.45 | See Example 1 |
| Anti-rabies antibody | 7G11A3 | 2.62 | See Example 1 |
| Secondary antibody | Goat anti-mouse IgG2a-HRP | — | Southernbiotech |
| Secondary antibody | Goat anti-mouse IgG2b-HRP | — | Southernbiotech |
| Secondary antibody | Goat anti-mouse Ig(H + L)-HRP | — | Southernbiotech |
| Rabies globulin | Human rabies immune globulin | 100 IU/ml | Shuanglin Pharmaceutical |
| Rabies vaccine | Rabies vaccine | — | Rabipur ®, Chiron Behring |

Binding curves of the five RVNAs to RV glycoprotein as determined by indirect chemiluminescence enzyme immunoassay (CLEIA) are shown in FIG. 1. The glycoprotein was diluted to 1:500 in PBS and then coated the microplate. Five clones of RVNA were diluted to 10000, 2000, 400, 80, 16, 3.2 and 0.64 ng/mL, respectively. Goat anti-mouse IgG2a-HRP and goat anti-mouse IgG2b-HRP were used as the enzyme conjugated secondary antibody. Relative luminescence unit (RLU) represents the chemiluminescence signal.

These results show that anti-rabies antibodies of the present technology specifically bind rabies virus glycoprotein, and that they are useful in methods related to such specific binding, including methods for detecting rabies virus glycoprotein in a sample, or treating or preventing rabies infection in a subject in need thereof and methods for providing post-exposure protection against rabies infection to a subject in need thereof.

Example 3

Neutralizing Potency of Murine RVNAs and Epitope Characterization

The in vitro neutralizing potency of the five RVNAs and the neutralizing epitope recognized by the RVNAs was determined as described herein. To prepare the CVS-11 virus, monolayers of neuroblastoma cells were infected with challenge virus standard-11 (CVS-11) or other viruses at a multiplicity of infection (MOI) of 0.3 for 15 min at 37° C./0.5% $CO_2$. The virus inoculum was then removed, fresh medium was added to the cells, and incubation was continued for 40 h at 37° C./0.5% $CO_2$. The culture supernatants were collected and stored at −80° C. until further use.

Standard rapid fluorescent focus inhibition test (RFFITs) for neutralization were performed as described previously in Smith et al. (A rapid fluorescent focus inhibition test (RFFIT) for determining rabies virus-neutralizing antibody. In: Meslin F-X, Kaplan M M, Koprowski H, eds. Laboratory techniques in rabies. 4th ed. Geneva, Switzerland:World Health Organization 1996; 181-192). To determine the neutralizing potency of each RVNA, their 50% neutralizing titers were compared with the 50% neutralizing titer of standard (standard GB), which was defined as 21.4 IU/mL. The results of the RFFIT test using CVS-11 rabies virus is shown in Table 4.

TABLE 4

In vitro neutralizing potency of RVNAs.

| No. | Clone | Neutralizing Potency (IU/mg) |
|---|---|---|
| 1 | 3D11E3 | 3676 |
| 2 | 3H10D3 | 3101 |
| 3 | 5A1C10 | 2110 |
| 4 | 6F11C1 | 4244 |
| 5 | 7G11A3 | 701 |

Figure 2:
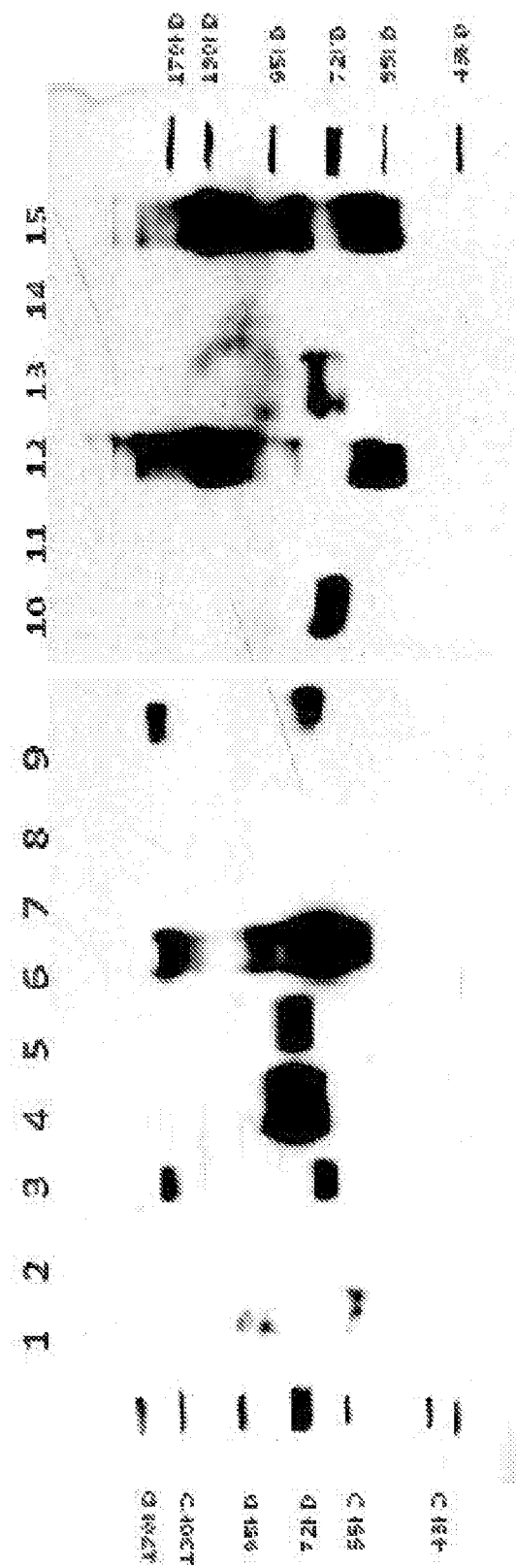
FIG. 2 is a Western Blot showing the five RVNAs recognize the linear epitope or conformational epitope on rabies virus glycoprotein (RVGP). The lanes are as follows: lane 1: 50 µL reducing RVGP with 7G11A3; lane 2: 5 µL reducing RVGP with 7G11A3; lane 3: 5 µL non-reducing RVGP with 7G11A3; lane 4: 50 µL reducing RVGP with 5A1C10; lane 5: 5 µL reducing RVGP with 5A1C10; lane 6: 5 µL non-reducing RVGP with 5A1C10; lane 7: 50 µL reducing RVGP with 6F11C1; lane 8: 5 µL reducing RVGP with 6F11C1; lane 9: 5 µL non-reducing RVGP with 6F11C1; lane 10: 50 µL reducing RVGP with 3H10D3; lane 11: 5 µL reducing RVGP with 3H10D3; lane 12: 5 µL non-reducing RVGP with 3H10D3; lane 13: 50 µL reducing RVGP with 3D11E3; lane 14: 5 µL reducing RVGP with 3D11E3; lane 15: 5 µL non-reducing RVGP with 3D11E3.
Figure 4A:
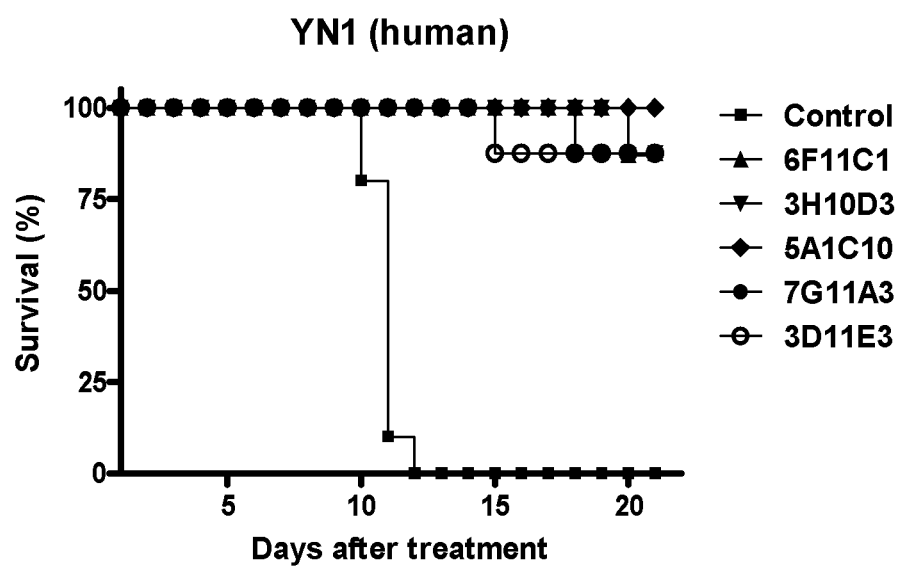
Figure 4B:
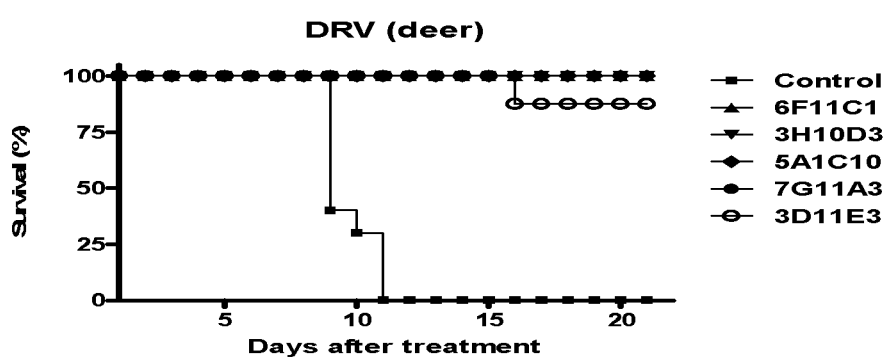
Figure 4C:
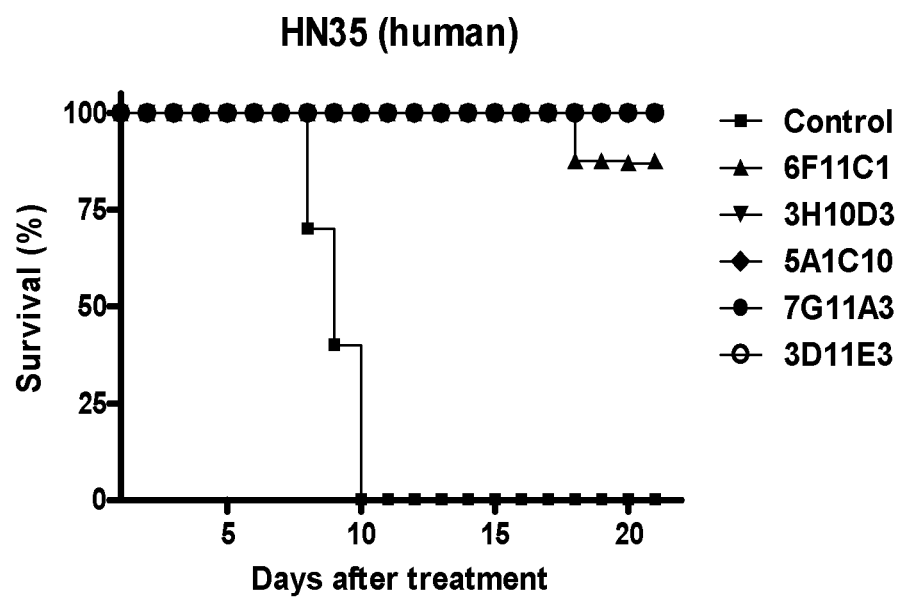
Figure 4D:
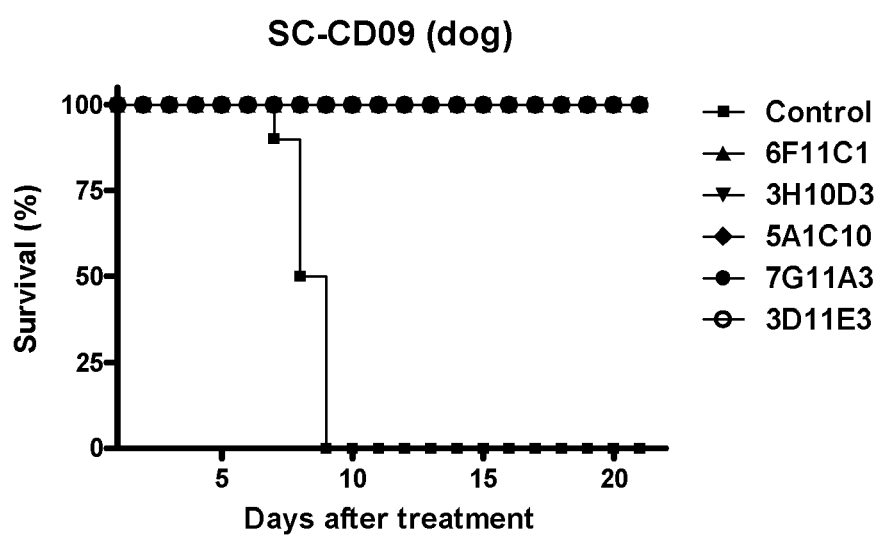
Figure 4E:
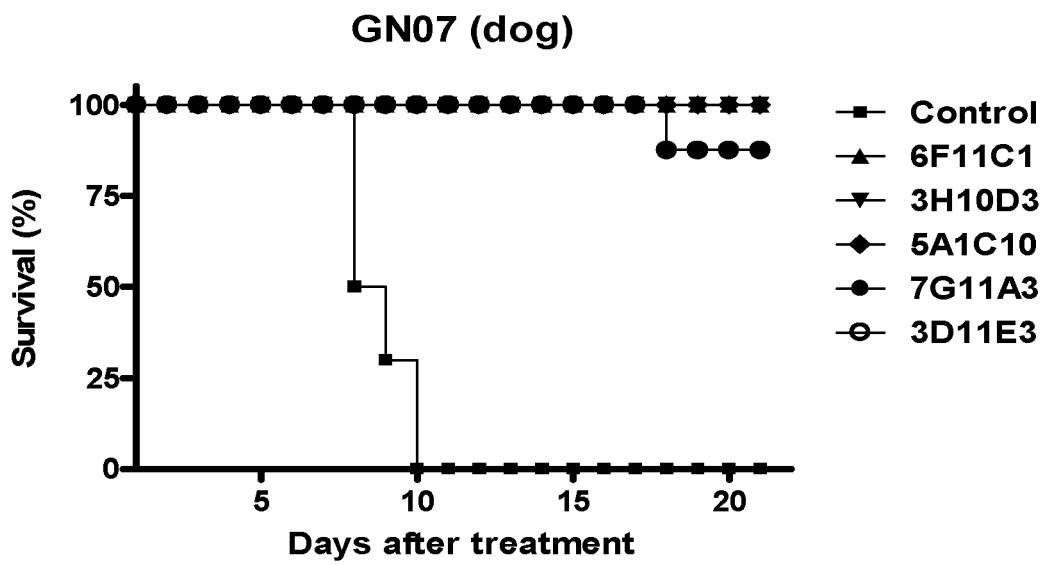
Figure 4F:
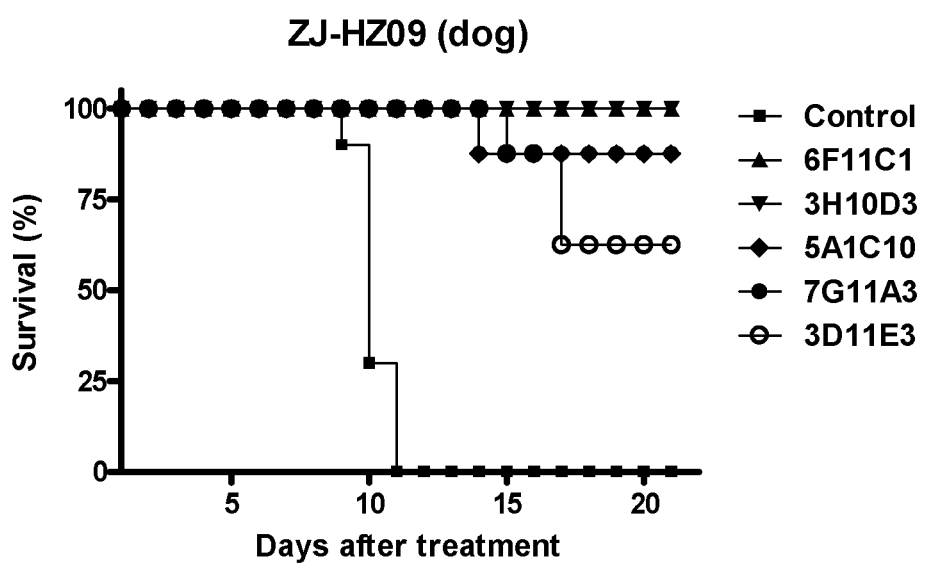
Figure 4G:
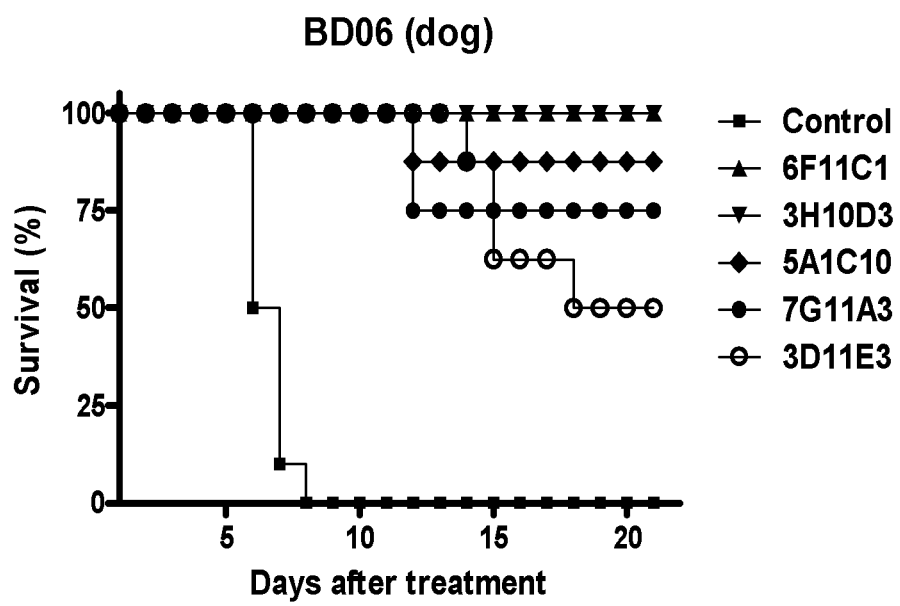
Figure 4H:
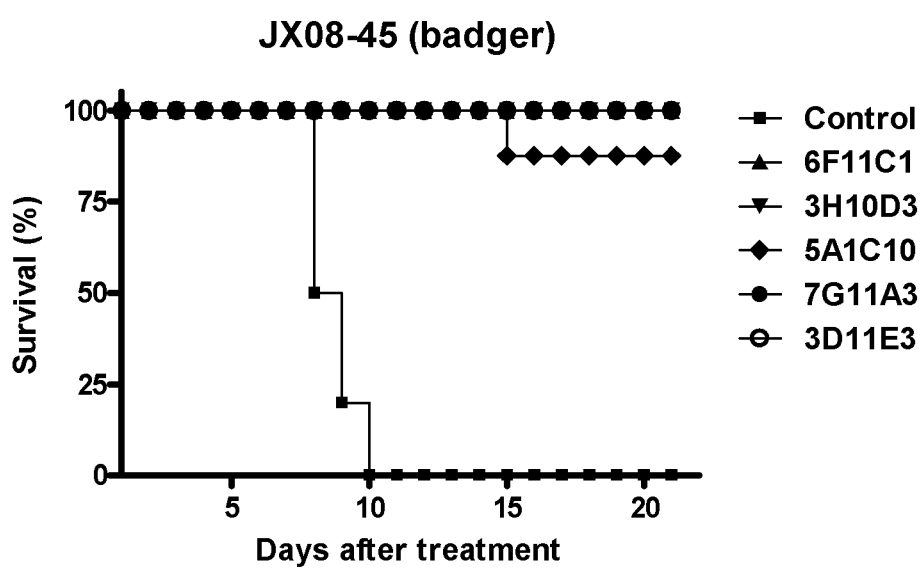
Figure 4I:
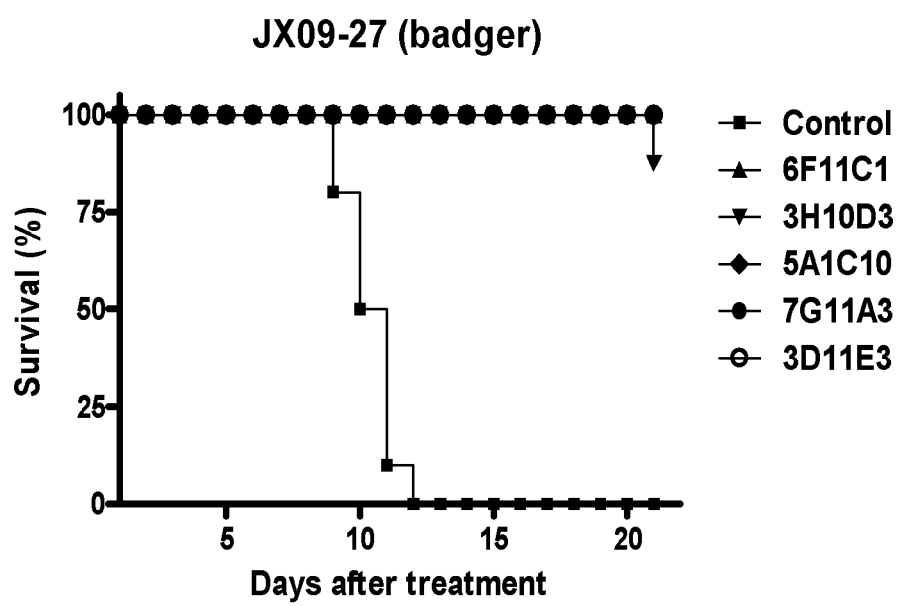
Figure 4J:
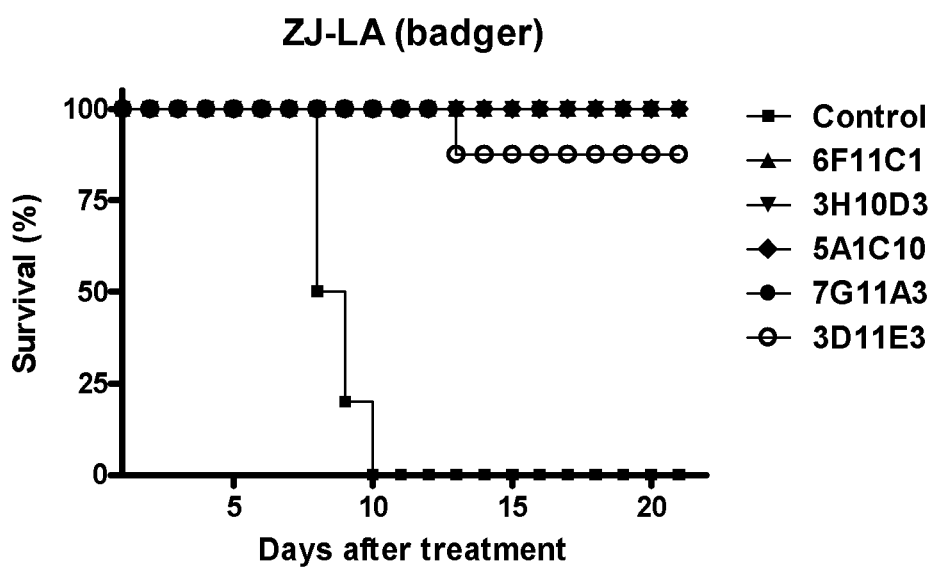
Figure 5A:
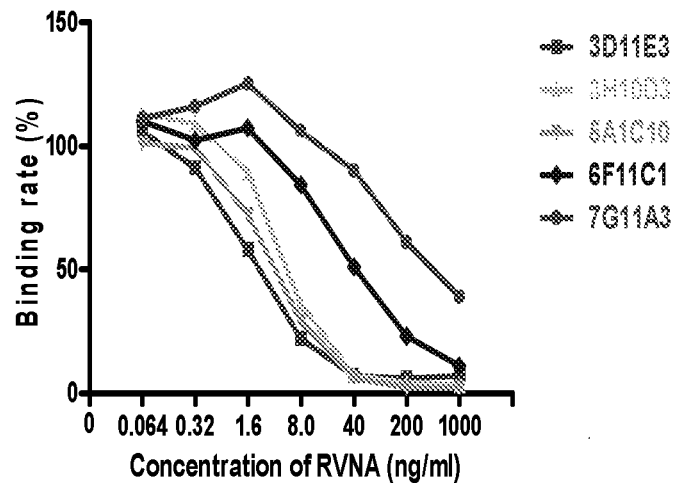
FIGS. 5A-5O are a series of graphs depicting exemplary results of a set of competition experiments performed using a CLEIA format. RVNAs 3D11E3, 3H10D3, 5A1C10, 6F11C1 and 7G11A3 compete with each other for binding to rabies virus glycoprotein (RVGP). The five illustrative RVNAs were allowed to bind to glycoprotein competing with 3D11E3-HRP (FIGS. 5A-5C), 3H10D3-HRP (FIGS. 5D-5F), 5A1C10-HRP (FIGS. 5G-5I), 6F11C1-HRP (FIGS. 5J-5L) and 7G11A3-HRP (FIGS. 5M-5O).
Figure 5B:
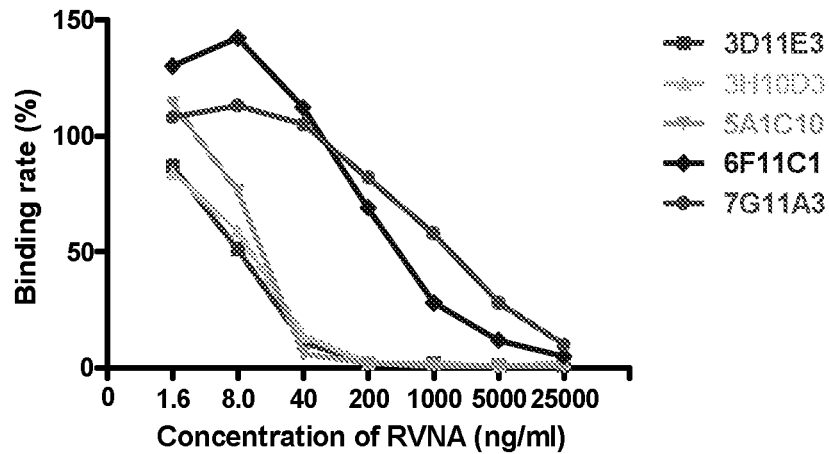
Figure 5C:
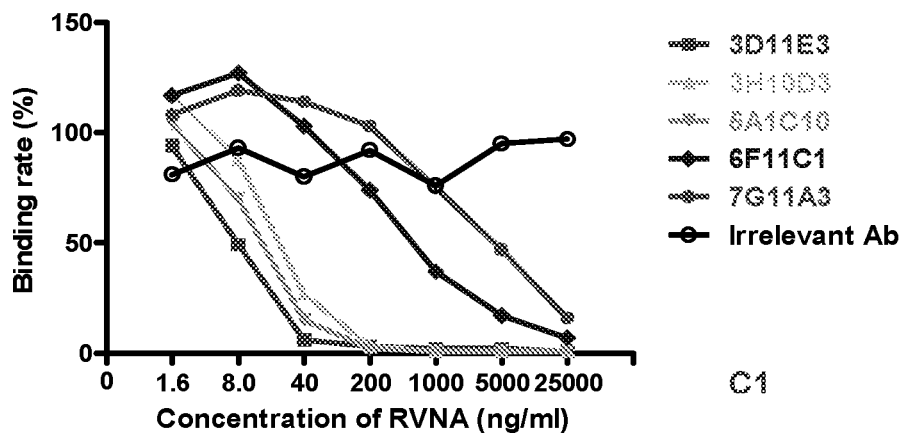
Figure 5D:
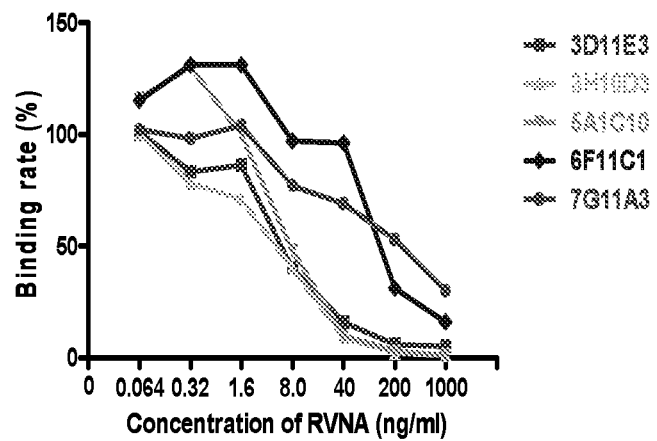
Figure 5G:
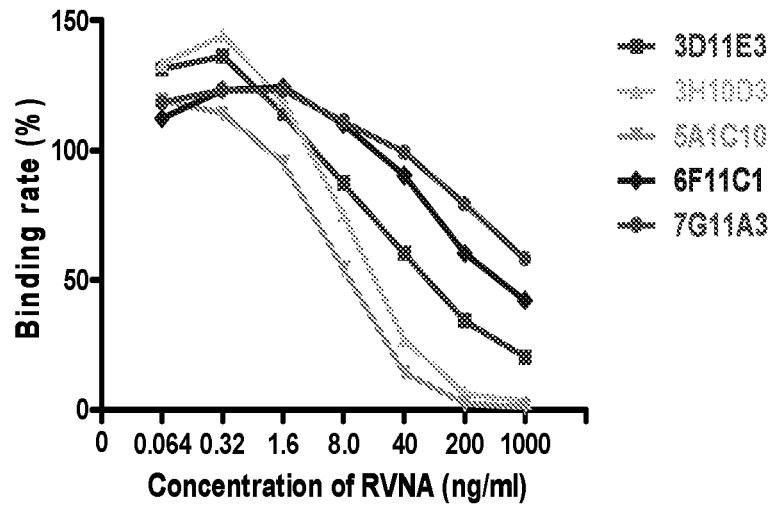
Figure 5H:
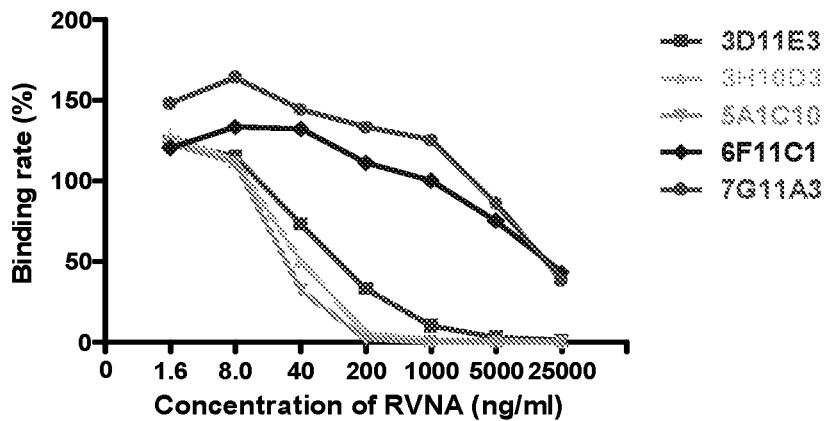
Figure 5I:
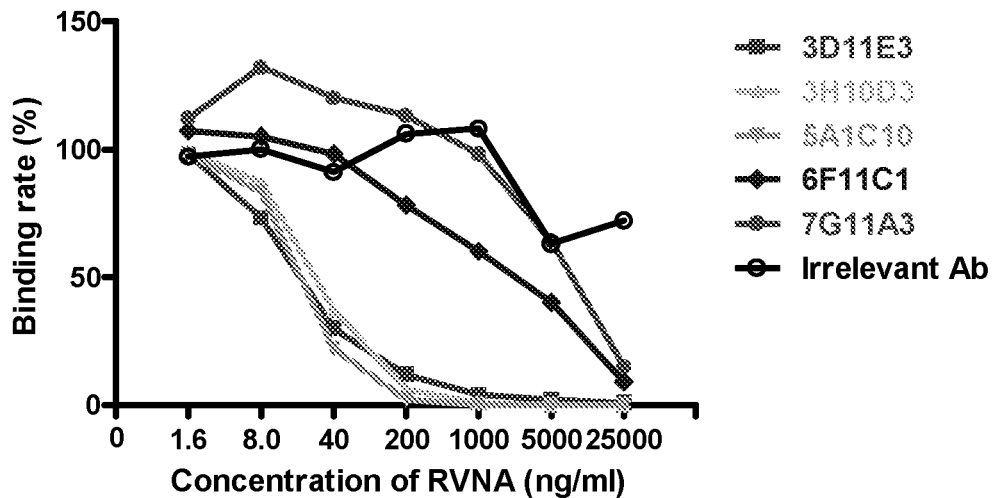
Figure 5J:
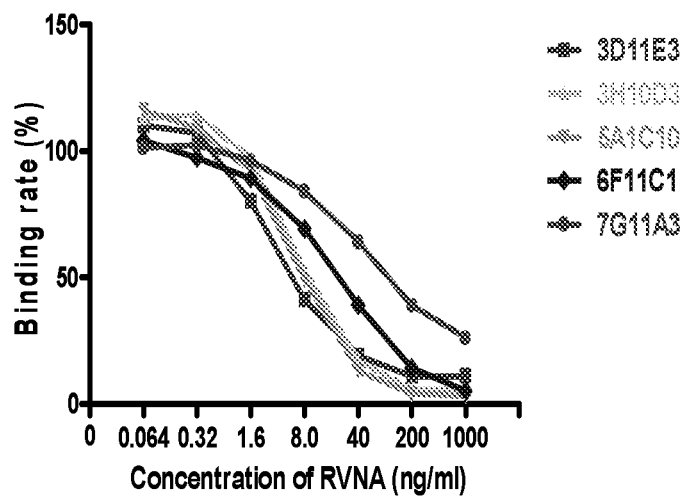
Figure 5K:
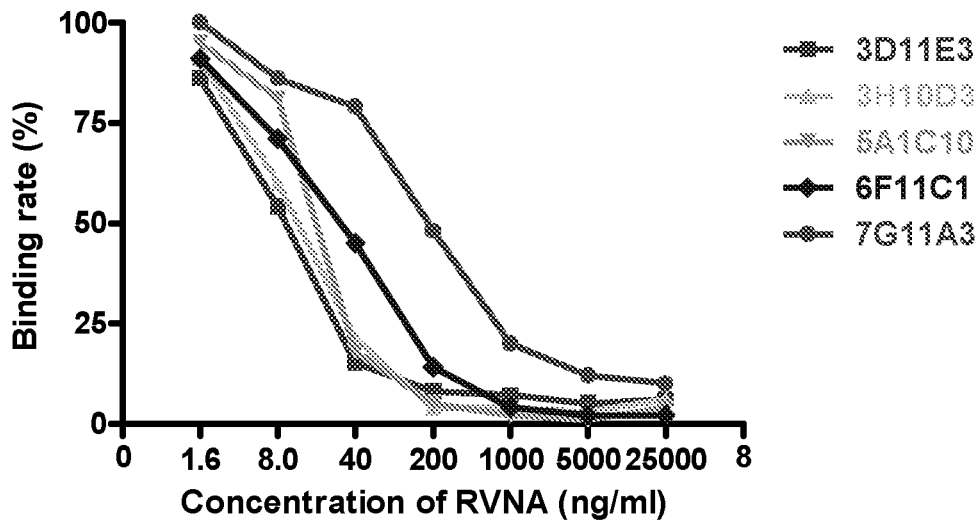
Figure 5L:
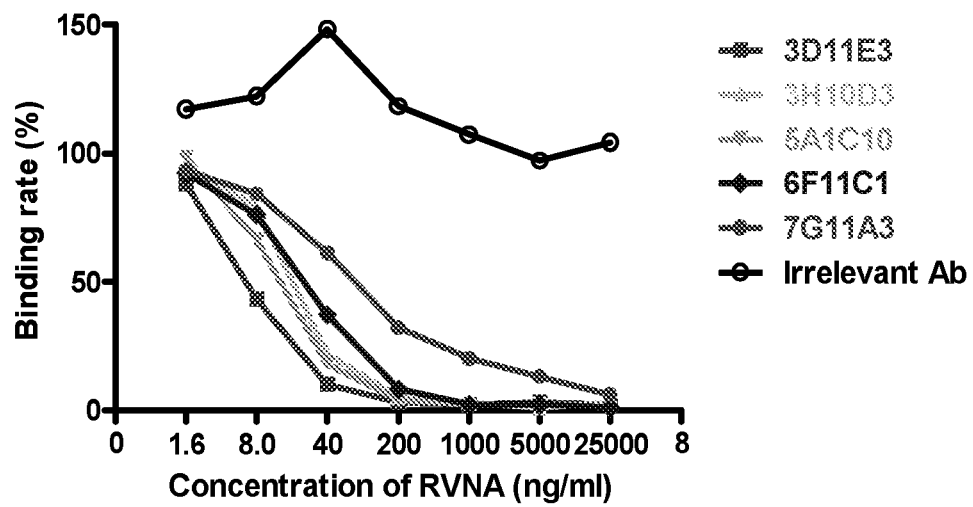
Figure 5M:
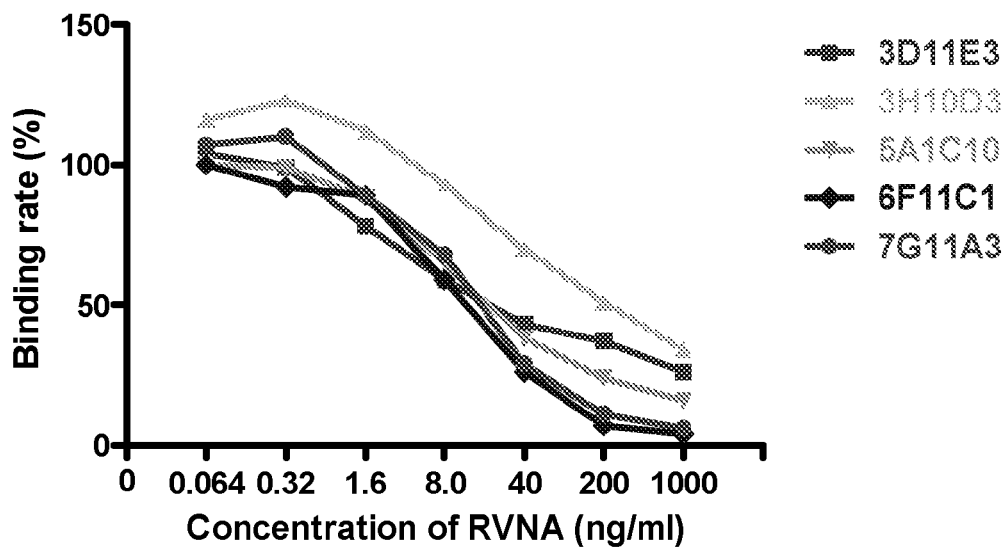
Figure 5N:
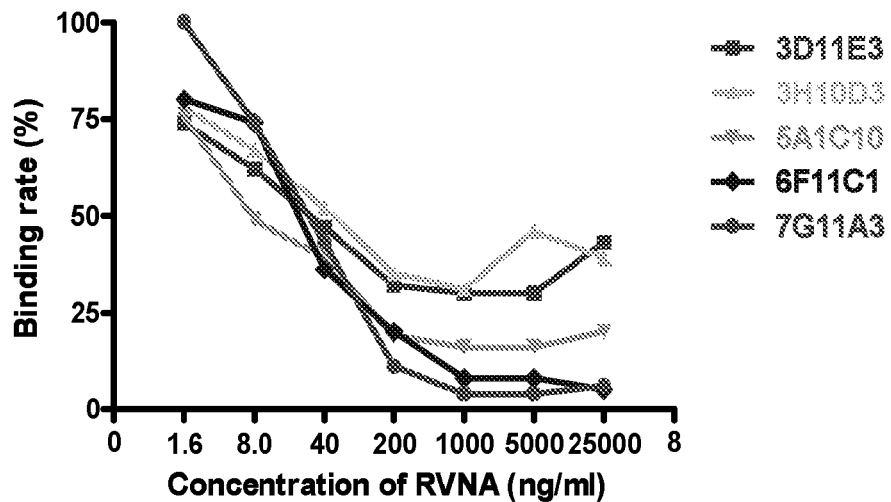
Figure 5O:
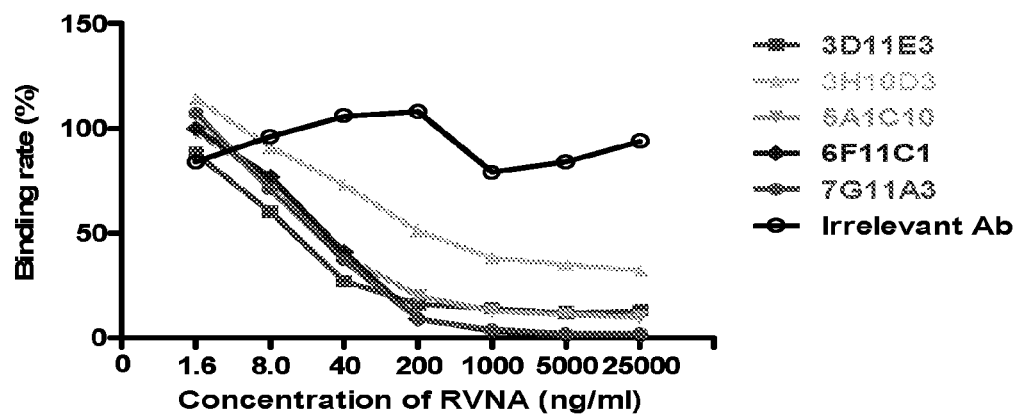

To identify the characteristics of the glycoprotein epitope that was recognized by 3D11E3, 3H10D3, 5A1C10, 6F11C1 and 7G11A3, Western analysis and CLEIA were performed. For the Western Blot, the reduced and non-reduced glycoproteins were separated by SDS-PAGE electrophoresis, and probed with the five RVNAs (FIG. 2). For the RVNAs, 1 µg/mL of the antibody was used. The secondary antibody was Goat anti-mouse Ig(H+L)-HRP, diluted 1:2000. It was found that the rabies virus glycoprotein can be recognized by all 5 RVNAs under non-reducing condition. However, only 3D11E3, 3H10D3 and 5A1C10 can recognize the reduced glycoprotein. The results confirmed that the epitope recognized by 3D11E3, 3H10D3 or 5A1C10 was a linear epitope while the epitope recognized by 6F11C1 or 7G11A3 was a conformational epitope.

The five RVNAs bind to the rabies virus glycoprotein (RVGP) which was treated with different buffers. The glycoprotein was dissolved in carbonate buffer (CB), carbonate buffer including 0.1% sodium dodecyl sulfate (CB+0.1% wt/vol SDS) and carbonate buffer including 0.1% Sodium dodecyl sulfate and 0.1% β-Mercaptoethanol (CB+0.1% wt/vol SDS+β-ME), respectively and then coated the microplate. The five RVNAs were diluted to 10000, 2000, 400, 80, 16, 3.2 and 0.64 ng/mL and then reacted with the RVGP. Goat anti-mouse IgG2a-HRP and goat anti-mouse IgG2b-HRP diluted 1:2000 were used as the enzyme conjugate of secondary antibody. The chemiluminescence signal (RLU) is shown in FIG. 3A-E. The results indicate that the epitope that was recognized by 6F11C1 or 7G11A3 was more sensitive to SDS than that recognized by 3D11E3, 3H10D3 or 5A1C10. Thus, the results obtained from the two methods were consistent each other that 3D11E3, 3H10D3 and 5A1C10 recognized linear epitopes and 6F11C1 and 7G11A3 recognized conformational epitopes.

These results show that anti-rabies antibodies of the present technology neutralize rabies virus infectivity, and that they are useful in methods relating to rabies virus neutralization, including methods for treating or preventing rabies infection in a subject in need thereof, and methods for providing post-exposure protection against rabies virus to a subject in need thereof.

Example 4

Breadth of Neutralization Against a Panel of Rabies Viruses

To analyze the breadth of neutralization, the coverage of the five RVNAs (3D11E3, 3H10D3, 5A1C10, 6F11C1 and 7G11A3) against a representative panel of 10 street rabies viruses (RVs) were determined by mouse neutralization test (MNT) (See Hasse, et al., 13(2) J. Biol. Stand. 123-28 (1985). The results were shown in FIG. 4I-J. and summarized in Table 5. All of the RVNAs produced neutralizing protection against most of the RVs. Although a small minority of subjects in the experimental group died, death occurred at least 2 days later than the control group (FIG. 4). Overall, the results indicated that all of the five RVNAs can potently neutralize the entire panel of RVs.

TABLE 5

Breadth of the neutralization against the street rabies viruses.

| Lyssavirus | 6F11C1 | 3H10D3 | 5A1C10 | 7G11A3 | 3D11E3 | Control |
|---|---|---|---|---|---|---|
| Dog, BD06, Hebei | ★ | ★ | 7/8 | 6/8 | 4/8 | 0/8 |
| Dog, GN07, Guangdong | ★ | ★ | ★ | 7/8 | 7/8 | 0/8 |
| Dog, ZJ-HZ09, Zhejiang | ★ | ★ | 6/8 | 7/8 | 6/8 | 0/8 |
| Dog, SC-CD09, Sichuan | ★ | ★ | ★ | ★ | ★ | 0/8 |
| Ferret Badger, ZJ-LA, Zhejiang | ★ | ★ | ★ | ★ | 7/8 | 0/8 |
| Ferret Badger, JX08-45, Jiangxi | ★ | ★ | 7/8 | ★ | ★ | 0/8 |
| Ferret Badger, JX09-27, Jiangxi | ★ | 7/8 | ★ | ★ | ★ | 0/8 |
| Human, HN35, Hunan | 7/8 | ★ | ★ | ★ | ★ | 0/8 |
| Human, YN1, Yunnan | 7/8 | 7/8 | ★ | 7/8 | 7/8 | 0/8 |
| Deer, DRV, Jilin | ★ | ★ | ★ | ★ | 7/8 | 0/8 |

Figure 6A:
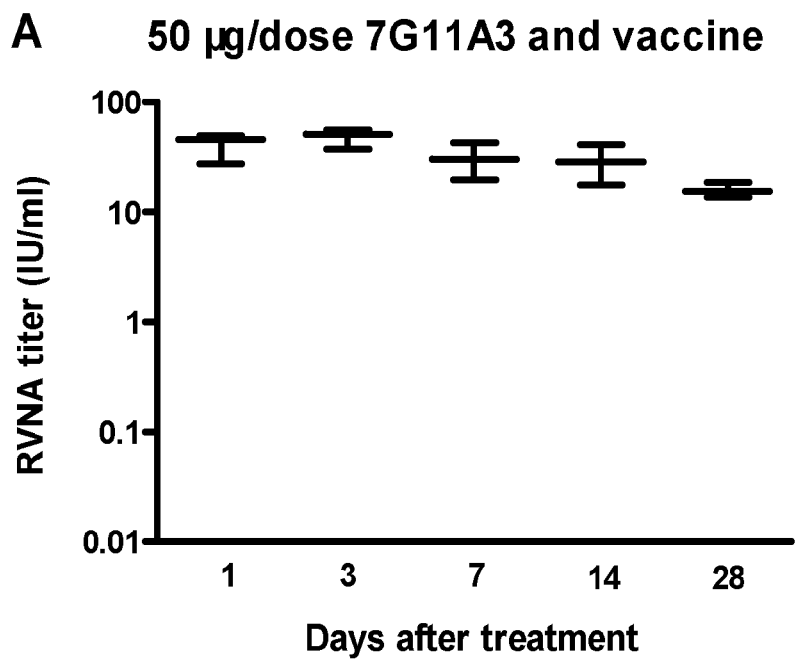
Figure 6B:
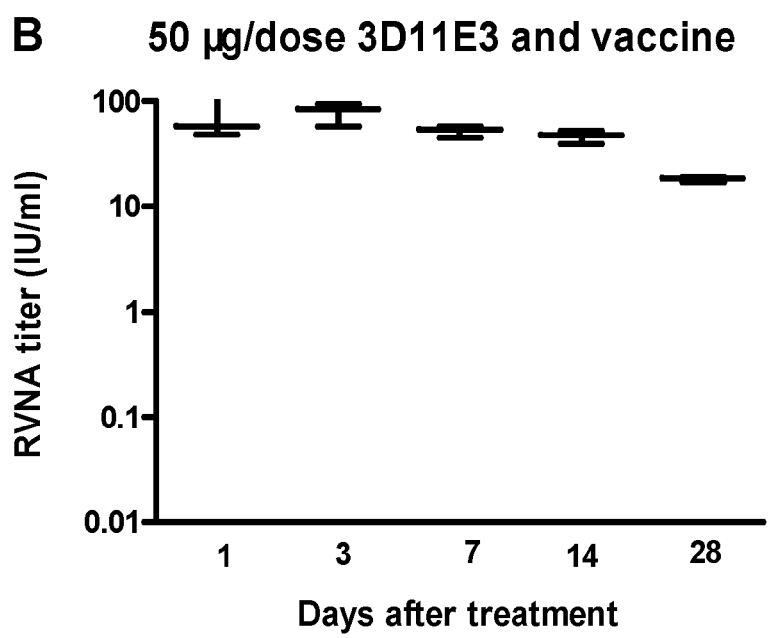
Figure 6C:
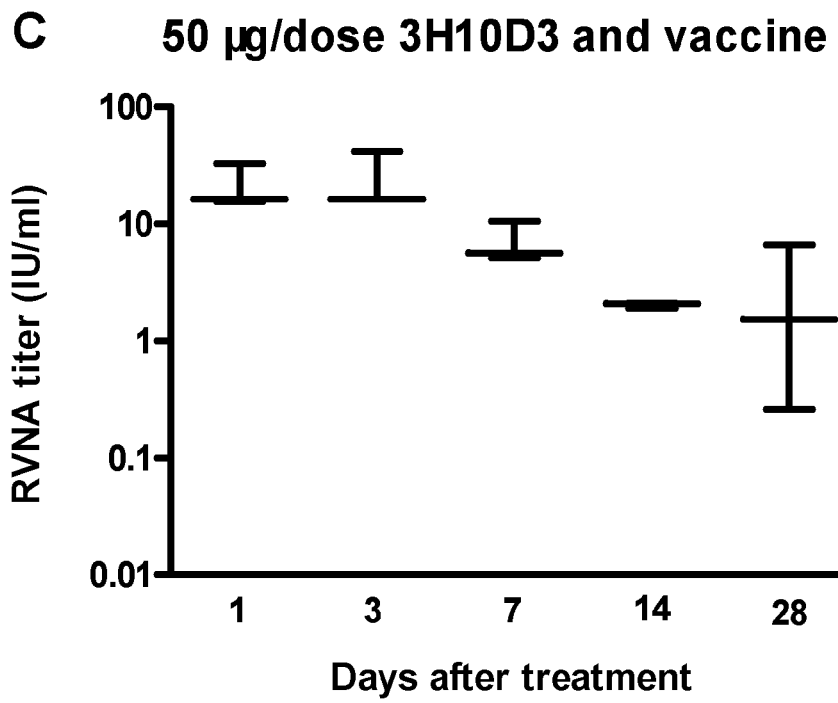
Figure 6D:
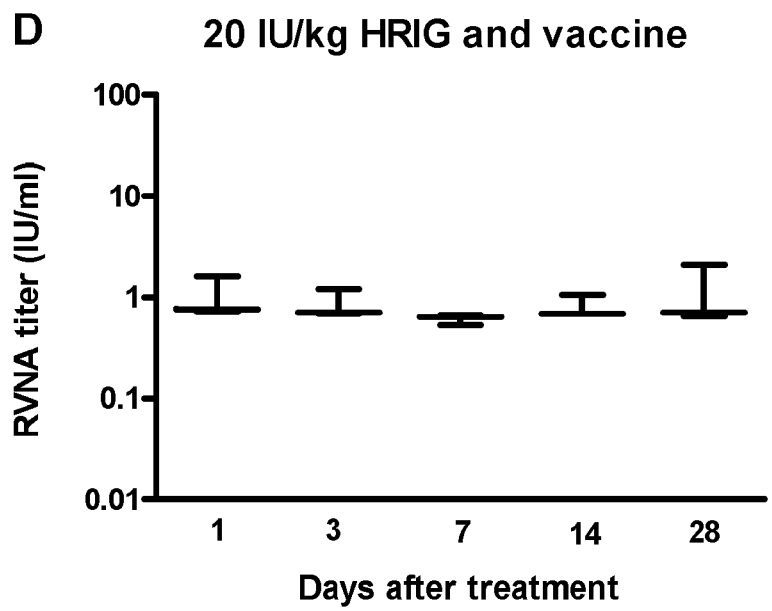
Figure 6E:
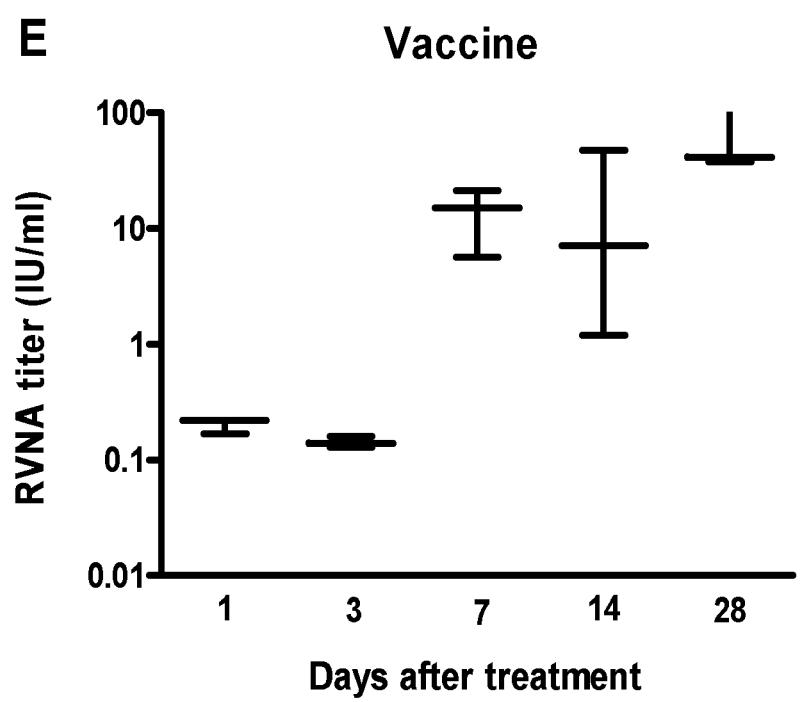

Data reflects survival of subjects 20 days following inoculation with rabies virus; Numerator indicates the number of surviving subjects in each group; Star (★) indicates survival of all 8 subjects in the group These results show that anti-rabies antibodies of the present technology neutralize rabies virus infectivity, and that they are useful in methods relating to rabies virus neutralization, including methods for treating or preventing rabies infection in a subject in need thereof, and methods for providing post-exposure protection against rabies virus to a subject in need thereof.

Example 5

Competition Between Anti-Rabies Neutralizing Antibodies

To investigate whether the antibodies 3D11E3, 3H10D3, 5A1C10, 6F11C1 and 7G11A3 compete with each other for binding to rabies virus glycoprotein, a set of competition experiments was performed using CLEIA (FIG. 5A-O). Briefly, a 96-well microplate was coated with rabies virus glycoprotein diluted to 1:500 in PBS. Fifty microliters (50 μL) diluted anti-rabies antibody and 50 μL anti-rabies mAb-HRP were added to each well and incubated at 37° C. for 1 hour. After the incubation, the plate was washed with washing solution and 50 μL mixed chemiluminescence substrate solution was added. The plate was kept in a dark room for 3 minutes and then the chemiluminescence intensity was measured.

The RLU of the well which had no anti-rabies mAb and only had anti-rabies mAb-HRP conjugate was defined as B0. The RLU of the other wells which had both anti-rabies mAb and anti-rabies mAb-HRP conjugate was defined as B. The binding rate was obtained by dividing B0 by B. The non-specific antibody did not block the binding of the five HRP-labeled RVNA (FIG. 5C, F, I, L, O), thereby serving as the negative control. The lower the binding rate was, the greater the competition of the RVNA with the HRP-labeled RVNA was. The results showed that 7G11A3 did not substantially effect the binding of 3D11A3-HRP (FIG. 5A, B, C), 3H10D3-HRP (FIG. 5D, E, F), 5A1C10-HRP (FIG. 5G, H, I) or 6F11C1-HRP (FIG. 5J, K, L) to the glycoprotein. The competition of 3H10D3 or 3D11E3 was minor compared with that of the other three RVNAs for the binding of 7G11A3-HRP to RVGP (FIG. 5M, N, O). Overall, the competition between 3D11E3, 3H10D3, and 7G11A3 was relatively minor compared to the other parings. On this basis, 3D11E3, 3H10D3, and 7G11A3 were selected for further experiments.

Example 6

Vaccine Immunogenicity in Non-Challenged Syrian Hamsters Treated with 3D11E3, 3H10D3, 7G11A3, or Human Rabies Virus Immunoglobulin During post-exposure prophylaxis (PEP), there exists the possibility that the simultaneous administration of RVNAs and vaccine decreases the ability of the vaccine to induce the threshold levels of neutralization antibodies required for protection. Therefore, it is important to evaluate the degree of the interference of the mAb treatment to vaccination. To determine the effect of the RVNA on vaccine potency, an in vivo animal experiment was performed in the absence of RV (FIG. 6). For PEP, BALB/c mice were administered 50 μg/dose RVNA plus vaccine or 20 IU/kg human rabies immunoglobulin (BRIG) plus vaccine. Control mice were administered vaccine only. There were 6 mice in each experimental group. On days 1, 3, 7, 14 and 28, blood was collected from the orbit. Pairs of samples were pooled in each group, yielding a total of three replicate serum samples for each condition. RVNA titers were measured 1, 3, 7, 14, and 28 days post-treatment. The results are summarized in FIG. 6.

On days 1 and 3, serum RVNA titers were high in mice that received 50 μg/dose RVNA (FIG. 6A-C). Titers were lower in subjects administered 20 IU/kg HRIG together with vaccine, but were still within the WHO requirement of >0.5 IU/mL (FIG. 6D). Titers were not detected in subjects administered only vaccine (FIG. 6E). RVNA titers in mice that received 50 μg/dose 7G11A3 (FIG. 6A) or 50 μg/dose 3D11E3 (FIG. 6B)

remained high during the 7-28 day period, and were higher than or equivalent to that of subjects administered only vaccine (FIG. 6E). However, RVNA titers in mice that received 50 µg/dose 3H10D3 decreased markedly from day 7 to day 28 (FIG. 6C). This result indicated that 7G11A3 and 3D11E3 did not interfere with the capacity of the vaccine to induce production of a neutralizing antibody, and 3H10D3 reduces the efficacy of the vaccine.

These results show that anti-rabies antibodies of the present technology neutralize rabies virus infectivity without reducing the immunogenicity of a rabies vaccine. As such, they are useful in methods relating to rabies virus neutralization in conjunction with the administration of a rabies vaccine, including methods for treating or preventing rabies infection in a subject in need thereof and methods for providing post-exposure protection against rabies infection to a subject in need thereof.

Example 7

Figure 7:
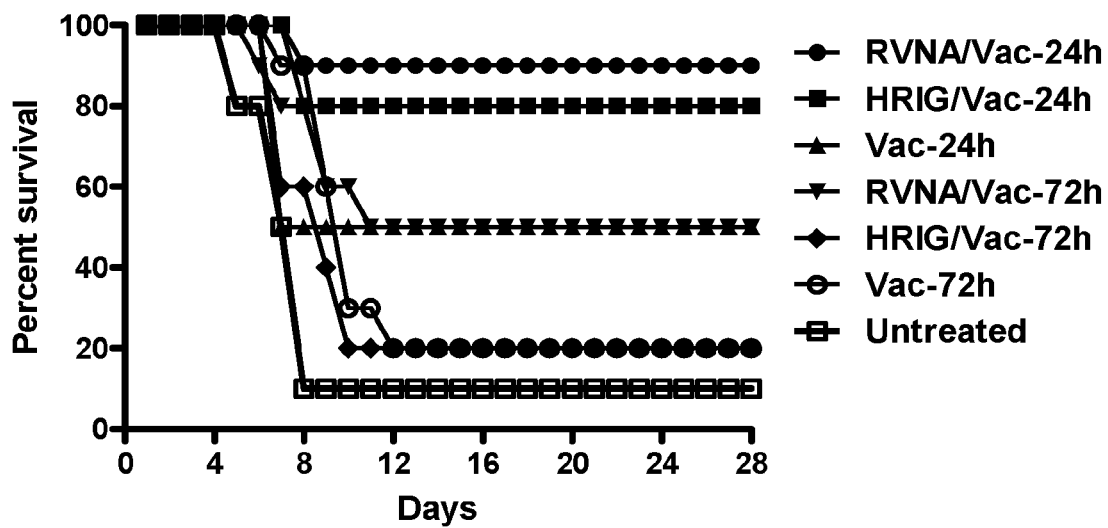
FIG. 7 is a graph showing Kaplan-Meier survival curves for Syrian hamsters (n=10 per group) challenged with dog street rabies virus (BD06).

In Vivo Neutralizing Performance of Anti-Rabies mAbs Cocktail Compared with Polyclonal HRIG To evaluate the in vivo neutralizing performance of a 3D11E3/7G11A3 cocktail, a Syrian hamster study was performed. Hamsters (n=10 per group) were infected with dog street RV (BD06) on day −1. Animals were vaccinated with rabies vaccine (Rabipur®, Chiron Behring GmbH & Co., Liederbach, Germany), human diploid cell vaccine (HDCV; Imovax®, Sanofi Pasteur, Swiftwater, Pa., USA) on day 0 and then treated with 3D11E3/7G11A3 cocktail consisting of equal amounts of 3D11E3 and 7G11A3 (0.5 mg/kg) or 20 IU/kg human rabies immune globulin (*Shuanglin Pharmaceutical*) with 24 hour or 72 hour decay, administered at the site of virus inoculation (i.e., right gastrocnemius). Additional doses of vaccine were administered in the left gastrocnemius muscle on days 3, 7, 14, and 28. Control groups received vaccine alone or were untreated. Hamsters were examined daily, and if they showed clinical signs of rabies infection they were euthanized. Clinical signs of rabies include: lethargy, fever, vomiting, and anorexia. Signs progress within days to cerebral dysfunction, cranial nerve dysfunction, ataxia, weakness, paralysis, seizures, difficulty breathing, difficulty swallowing, excessive salivation, abnormal behavior, aggression, and/or self-mutilation. The results are summarized in FIG. 7.

The untreated negative control group had a survival rate of 10%, indicating that viral infection was effective. With 24 hour decay, subjects administered vaccine together with the 3D11E3/7G11A3 cocktail displayed a survival rate of 90% (9/10), and those administered the vaccine together with BRIG displayed a survival rate of 80% (8/10). By contrast, with a 72 hour decay, subjects administered vaccine together with the 3D11E3/7G11A3 cocktail and BRIG dropped to 50% (5/10) and 20% (2/10), respectively.

These results show that a combination of anti-rabies antibodies of the present technology neutralize rabies virus infectivity, and that they are useful in methods relating to rabies virus neutralization, including methods for treating or preventing rabies infection in a subject in need thereof and methods for providing post-exposure protection against rabies infection to a subject in need thereof.

Example 8

Generation of Chimeric and Humanized 3D11E3-1A9 Antibodies

This Example describes the preparation of chimeric and humanized forms of the 3D11E3-1A9 antibody described in Examples 2-7 above.

Cloning and Sequencing of Mouse 1A9 Variable Region Genes.

Mouse CT.RV 3D11E3 1A9 (referred to as "1A9" in this Example) hybridoma cells were grown in Hybridoma-SFM (Invitrogen, Carlsbad, Calif.) containing 12% fetal bovine serum (FBS; HyClone, Logan, Utah) at 37° C. in a 7.5% $CO_2$ incubator. Total RNA was extracted from approximately $10^7$ hybridoma cells using TRIzol reagent (Invitrogen) according to the supplier's protocol. Oligo dT-primed cDNA for 5'-RACE was synthesized using the SMARTer RACE cDNA Amplification Kit (Clontech, Mountain View, Calif.) following the supplier's protocol. The variable region cDNAs for 1A9 heavy and light chains were amplified by polymerase chain reaction (PCR) with Phusion DNA polymerase (New England Biolabs, Beverly, Mass.) using 3' primers that anneal respectively to the mouse gamma-2a and kappa chain constant regions, and the 5'-RACE primer (Universal Primer A Mix or Nested Universal Primer A) provided in the SMARTer RACE cDNA Amplification Kit. For PCR amplification of heavy chain variable region ($V_H$), two 3' primers were used. They have the sequence 5'-GCCAGTGGATAGAC-CGATGG-3' (SEQ ID NO: 1) and 5'-ACAGTCACT-GAGCTGC-3' (SEQ ID NO: 2). For PCR amplification of light chain variable region ($V_L$), the 3' primer has the sequence 5'-GATGGATACAGTTGGTGCAGC-3' (SEQ ID NO: 3). The amplified $V_H$ and $V_L$ cDNAs were cloned into the pCR4Blunt-TOPO vector (Invitrogen) for sequence determination. DNA sequencing was carried out at Tocore (Menlo Park, Calif.). Several heavy and light chain clones were sequenced and unique sequences homologous to typical mouse heavy and light chain variable regions were identified. No unusual features were noticed in the mature 1A9 $V_H$ and $V_L$ amino acid sequences.

The nucleotide sequence (SEQ ID NO: 4) of mouse 1A9 $V_H$ cDNA is shown in Table 6 along with the deduced amino acid sequence (SEQ ID NO: 5). The signal peptide sequence is in italic. The N-terminal amino acid residue (E) of the mature $V_H$ is double-underlined. CDR sequences according to the definition of Kabat et al. (Sequences of Proteins of Immunological Interests, Fifth edition, NIH Publication No. 91-3242, U.S. Department of Health and Human Services, 1991) are underlined.

TABLE 6

Nucleotide (SEQ ID NO: 4) and Amino Acid (SEQ ID NO: 5) Sequences of Murine 1A9 $V_H$ cDNA ATGGGAGGGATCTGGATCTTTCTCTTCCTCCTGTCAGGAACTGCAGGTGCCCACTCTGAG
*M  G  G  I  W  I  F  L  F  L  L  S  G  T  A  G  A  H  S*  <u>E</u>

ATCCAGCTGCAGCAGACTGGACCTGAGCTGGTGAAGCCTGGGGCTTCAGTGAAGATATCC
 I  Q  L  Q  Q  T  G  P  E  L  V  K  P  G  A  S  V  K  I  S

TABLE 6-continued

Nucleotide (SEQ ID NO: 4) and Amino Acid (SEQ ID NO: 5) Sequences of Murine 1A9 V$_H$ cDNA

```
TGCAAGGCTTCTGGTTATTCATTCACTGACTACATCATGCTCTGGGTGAAGCAGAGCCAT
 C   K   A   S   G   Y   S   F   T   D   Y   I   M   L   W   V   K   Q   S   H

GGAAAGAGCCTTGAGTGGATTGGAGATATTTATCCTTACTATGGTAGTACTAGCTACAAT
 G   K   S   L   E   W   I   G   D   I   Y   P   Y   Y   G   S   T   S   Y   N

CTGAAGTTCAAGGGCAAGGCCACATTGACTGTAGACAAATCTTCCAGCACAGCCTACATG
 L   K   F   K   G   K   A   T   L   T   V   D   K   S   S   S   T   A   Y   M

CAGCTCAACAGTCTGACATCTGAGGACTCTGCAGTCTATTACTGTGCAAGGCAGGGCGGG
 Q   L   N   S   L   T   S   E   D   S   A   V   Y   Y   C   A   R   Q   G   G

GATGGTAACTACGTCCTCTTTGACTACTGGGGCCAAGGCACCACTCTCACAGTCTCCTCA
 D   G   N   Y   V   L   F   D   Y   W   G   Q   G   T   T   L   T   V   S   S
```

The nucleotide sequence (SEQ ID NO: 6) of mouse 1A9V$_L$ cDNA is shown in Table 7 along with the deduced amino acid sequence (SEQ ID NO: 7). The signal peptide sequence is in italic. The N-terminal amino acid residue (D) of the mature V$_L$ is double-underlined. CDR sequences according to the definition of Kabat et al. (1991) are underlined.

TABLE 7

Nucleotide (SEQ ID NO: 6) and Amino Acid (SEQ ID NO: 7) Sequences of Murine 1A9 V$_L$ cDNA

```
ATGGAGTCACAGACTCAGGTCTTTGTATACATGTTGCTGTGGTTGTCTGGTGTTGATGGA
 M   E   S   Q   T   Q   V   F   V   Y   M   L   L   W   L   S   G   V   D   G

GACATTGTGATGACCCAGTCTCAAAAATTCATGTCCACATCAGTAGGAGACAGGGTCAGC
 D   I   V   M   T   Q   S   Q   K   F   M   S   T   S   V   G   D   R   V   S

GTCACCTGCAAGGCCAGTCAGAATGTGGGTACTACTGTTGCCTGGTATCAACAGAAACCA
 V   T   C   K   A   S   Q   N   V   G   T   T   V   A   W   Y   Q   Q   K   P

GGACAATCTCCTAAAGCACTGATTTACTCGGCATCCTACCGGTACAGTGGAGTCCCTGAT
 G   Q   S   P   K   A   L   I   Y   S   A   S   Y   R   Y   S   G   V   P   D

CGCTTCACAGGCAGTGGATCTGGGACAGATTTCACTCTCACCATCAGCAATGTGCAGTCT
 R   F   T   G   S   G   S   G   T   D   F   T   G   T   I   S   N   V   Q   S

GAAGACTTGGCAGAATATTTCTGTCAGCAATATAACAGCTATCCATTCACGTTCGGCTCG
 E   D   L   A   E   Y   F   C   Q   Q   Y   N   S   Y   P   F   T   Y   G   S

GGGACAAAGTTGGAAATAAAA
 G   T   K   L   E   I   K
```

Construction of Chimeric 1A9 IgG1/κ Antibody.

A gene encoding 1A9 V$_H$ was generated as an exon including a splice donor signal and appropriate flanking restriction enzyme sites by PCR using 1A9 V$_H$ cDNA as a template, 5'-GCAACTAGTACCACCATGGGAGGGATCTGGATC-3' (SEQ ID NO: 8) (SpeI site is underlined) as a 5' primer, and 5'-GGGAAGCTTGTTTTAAGGACTCACCTGAGGAGACTGTGAGAGTGGTGCC-3' (SEQ ID NO: 9) (HindIII site is underlined) as a 3' primer. The nucleotide sequence (SEQ ID NO: 10) of the designed Ch1A9 V$_H$ gene flanked by SpeI and HindIII sites (underlined) is shown in Table 8 along with the deduced amino acid sequence (SEQ ID NO: 11). The signal peptide sequence is in italic. The N-terminal amino acid residue (E) of the mature V$_H$ is double-underlined. CDR sequences according to the definition of Kabat et al. (1991) are underlined. The intron sequence is in italic.

TABLE 8

Nucleotide (SEQ ID NO: 10) and Amino Acid (SEQ ID NO: 11) Sequences of Chimeric 1A9 V$_H$ cDNA

```
ACTAGTACCACCATGGGAGGGATCTGGATCTTTCTCTTCCTCCTGTCAGGAACTGCAGGT
            M   G   G   I   W   I   F   L   F   L   L   S   G   T   A   G

GCCCACTCTGAGATCCAGCTGCAGCAGACTGGACCTGAGCTGGTGAAGCCTGGGGCTTCA
 A   H   S   E   I   Q   L   Q   Q   T   G   P   E   L   V   K   P   G   A   S

GTGAAGATATCCTGCAAGGCTTCTGGTTATTCATTCACTGACTACATCATGCTCTGGGTG
 V   K   I   S   C   K   A   S   G   Y   S   F   T   D   Y   I   M   L   W   V
```

TABLE 8-continued

Nucleotide (SEQ ID NO: 10) and Amino Acid (SEQ ID NO: 11) Sequences of Chimeric 1A9 $V_H$ cDNA

```
AAGCAGAGCCATGGAAAGAGCCTTGAGTGGATTGGAGATATTTATCCTTACTATGGTAGT
 K  Q  S  H  G  K  S  L  E  W  I  G  D  I  Y  P  Y  Y  G  S

ACTAGCTACAATCTGAAGTTCAAGGGCAAGGCCACATTGACTGTAGACAAATCTTCCAGC
 T  S  Y  N  L  K  F  K  G  K  A  T  L  T  V  D  K  S  S  S

ACAGCCTACATGCAGCTCAACAGTCTGACATCTGAGGACTCTGCAGTCTATTACTGTGCA
 T  A  Y  M  Q  L  N  S  L  T  S  E  D  S  A  V  Y  Y  C  A

AGGCAGGGCGGGGATGGTAACTACGTCCTCTTTGACTACTGGGGCCAAGGCACCACTCTC
 R  Q  G  G  D  G  N  Y  V  L  F  D  Y  W  G  Q  G  T  T  L

ACAGTCTCCTCAGGTGAGTCCTTAAAACAAGCTT
 T  V  S  S
```

Likewise, a gene encoding Ch1A9 $V_L$ was generated as an exon including a splice donor signal and appropriate flanking restriction enzyme sites by PCR using Ch1A9 $V_L$ cDNA as a template, 5'-GCTGCTAGCACCACCATGGAGTCACAGACTCAG-3' (SEQ ID NO: 12) (NheI site is underlined) as a 5' primer, and 5'-GGGGAATTCGCAAAAGTCTACTTACGTTTTATTTCCAACTTTGTCCCCGA-3' (SEQ ID NO: 13) (EcoRI site is underlined) as a 3' primer.

The nucleotide sequence (SEQ ID NO: 14) of the designed Ch1A9 $V_L$ gene flanked by NheI and EcoRI sites (underlined) is shown in Table 9 along with the deduced amino acid sequence (SEQ ID NO: 15). The signal peptide sequence is in italic. The N-terminal amino acid residue (D) of the mature $V_L$ is double-underlined. CDR sequences according to the definition of Kabat et al. (1991) are underlined. The intron sequence is in italic.

Figure 8:
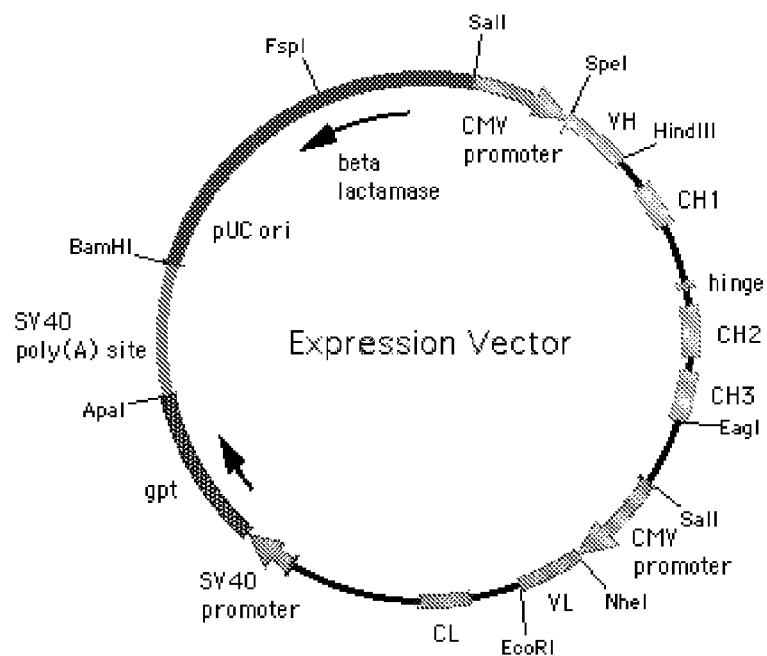
FIG. 8 is a schematic representation of the expression vector pCH1A9.

The splice donor signals of the Ch1A9 $V_H$ and $V_L$ exons were derived from the mouse germline 1112 and Jκ4 sequences, respectively. PCR-amplified fragments were gel-purified using NucleoSpin Extraction II Kit (Macherey-Nagel, Bethlehem, Pa.) and cloned into the pCR4Blunt-TOPO vector for sequence confirmation. The correct V fragments were digested with SpeI and HindIII (for $V_H$) or NheI and EcoRI (for $V_L$), gel-purified and cloned into a mammalian expression vector carrying human gamma-1 and kappa constant regions for production of chimeric Ch1A9 IgG1/κ antibody. The schematic structure of the resulting expression vector, pCh1A9, is shown in FIG. 8.

Design of Humanized 1A9 $V_H$ and $V_L$ Genes.

CDR sequences together with framework amino acid residues important for maintaining the CDR structure were grafted from 1A9 $V_H$ and $V_L$ into the corresponding selected human framework sequences. Human $V_H$ sequences homologous to the 1A9 $V_H$ frameworks were searched for within the GenBank database, and the $V_H$ sequence encoded by the human DA980102 cDNA (DA980102 $V_H$) (GenBank accession number; Kimura et al., Genome Res. 16:55-65, 2006) was chosen as an acceptor for humanization. The CDR sequences of 1A9 $V_H$ were first transferred to the corresponding positions of DA980102 $V_H$.

Based on the homology search with the 1A9 $V_L$ framework sequences, the human Vκ region encoded by the CB958542

TABLE 9

Nucleotide (SEQ ID NO: 14) and Amino Acid (SEQ ID NO: 15) Sequences of Chimeric 1A9 $V_L$ cDNA

```
GCTAGCACCACCATGGAGTCACAGACTCAGGTCTTTGTATACATGTTGCTGTGGTTGTCT
          M  E  S  Q  T  Q  V  F  V  Y  M  L  L  W  L  S

GGTGTTGATGGAGACATTGTGATGACCCAGTCTCAAAAATTCATGTCCACATCAGTAGGA
 G  V  D  G  D  I  V  M  T  Q  S  Q  K  F  M  S  T  S  V  G

GACAGGGTCAGCGTCACCTGCAAGGCCAGTCAGAATGTGGGTACTACTGTTGCCTGGTAT
 D  R  V  S  V  T  C  K  A  S  Q  N  V  G  T  T  V  A  W  Y

CAACAGAAACCAGGACAATCTCCTAAAGCACTGATTTACTCGGCATCCTACCGGTACAGT
 Q  Q  K  P  G  Q  S  P  K  A  L  I  Y  S  A  S  Y  R  Y  S

GGAGTCCCTGATCGCTTCACAGGCAGTGGATCTGGGACAGATTTCACTCTCACCATCAGC
 G  V  P  D  R  F  T  G  S  G  S  G  T  D  F  T  L  T  I  S

AATGTGCAGTCTGAAGACTTGGCAGAATATTTCTGTCAGCAATATAACAGCTATCCATTC
 N  V  Q  S  E  D  L  A  E  Y  F  C  Q  Q  Y  N  S  Y  P  F

ACGTTCGGCTCGGGGACAAAGTTGGAAATAAAACGTAAGTAGACTTTTGCGAATTC
 T  F  G  S  G  T  L  E  I  K
``` cDNA (CB958542 $V_L$) (GenBank accession number; NIH-MGC EST Sequencing Project, 1999) was chosen as an acceptor for humanization. CDR sequences of 1A9 $V_L$ were first transferred to the corresponding positions of CB958542 $V_L$. Next, at framework position 46, an amino acid residue from mouse 1A9 $V_L$ was substituted for the corresponding human residue. While A1a at position 46 in mouse 1A9 $V_L$ is located at a framework position important for the formation of the CDR structure, detailed analysis of the 1A9 variable regions that an amino acid residue at position 46 in Hu1A9

V$_L$1 could be replaced with the human corresponding residue, Val, in CB958542 V$_L$ without losing the antigen-binding affinity. In order to further reduce potential immunogenicity of humanized 1A9 antibody, a second humanized V$_L$ (Hu1A9 V$_L$2) was designed, in which Ala at position 46 in Hu1A9 V$_L$1 was replaced with Val.

Construction of Humanized 1A9 V$_H$ and V$_L$ Genes.

A gene encoding Hu1A9 V$_H$ was designed as an exon including a signal peptide, a splice donor signal, and appropriate restriction enzyme sites for subsequent cloning into a mammalian expression vector. The splice donor signal of the Hu1A9 V$_H$ exon was derived from the human germline JH1 sequence. Since the signal peptide encoded by the mouse 1A9 V$_H$ gene was predicted to be suboptimal for precise cleavage by the SIG-Pred signal peptide prediction software, the signal peptide sequence of the human DA980102 V$_H$ gene was used in Hu1A9 V$_H$.

The Hu1A9 V$_H$ and V$_L$ genes were constructed by GenScript USA (Piscataway, N.J.). After digestion with SpeI and HindIII (for V$_H$) or NheI and EcoRI (for V$_L$), Hu1A9 V$_H$ and V$_L$ genes were subcloned into corresponding sites in a mammalian expression vector for production in the human IgG1/κ form. The resultant expression vector, pHu1A9-1, expresses a humanized antibody containing the Hu1A9 V$_H$ and V$_L$1 regions (Hu1A9-1). Likewise, pHu1A9-2 expresses a humanized antibody containing Hu1A9 V$_H$ and V$_L$2 (Hu1A9-2).

The nucleotide sequence (SEQ ID NO: 16) of the Hu1A9 V$_H$ gene flanked by SpeI and HindIII sites (underlined) is shown in Table 10 along with the deduced amino acid sequence (SEQ ID NO: 17). The signal peptide sequence is in italic. The N-terminal amino acid residue (Q) of the mature V$_H$ is double-underlined. CDR sequences according to the definition of Kabat et al. (1991) are underlined. The intron sequence is in italic.

TABLE 10

Nucleotide (SEQ ID NO: 16) and Amino Acid (SEQ ID NO: 17) Sequences of Humanized Hu1 A9 V$_H$ Gene

```
ACTAGTACCACCATGGACTGGACCTGGAGGATCCTCTTTTTGGTGGCAGCAGCCACAGGT
        M   D   W   T   R   I   I   L   F   L   V   A   A   A   T   G

GCCCACTCCCAGGTCCAGCTTGTGCAGTCTGGGGCTGAAGTGAAAAAGCCTGGGGCCTCA
 A   H   S   Q   V   Q   L   V   Q   S   G   A   E   V   K   K   P   G   A   S

GTGAAGGTTTCCTGCAAGGCTTCTGGATACTCATTCACTGACTATATCATGCTTTGGGTG
 V   K   V   S   C   K   A   S   G   Y   S   F   T   D   Y   I   M   L   W   V

CGCCAGGCCCCTGGACAAAGGCTTGAGTGGATTGGAGATATCTATCCTTACTATGGCAGT
 R   Q   A   P   G   Q   R   L   E   W   I   G   D   I   Y   P   Y   Y   G   S

ACAAGCTATAATCTGAAGTTCAAGGGCAAGGCCACCCTCACCGTCGACACATCCGCGAGC
 T   S   Y   N   L   K   F   K   G   K   A   T   L   T   V   D   T   S   A   S

ACAGCCTACATGGAGCTCAGCAGCCTGAGATCTGAAGACACCGCTGTGTATTACTGTGCC
 T   A   Y   M   E   L   S   S   L   R   S   E   D   T   A   V   Y   Y   C   A

AGGCAGGGCGGCGATGGAAACTACGTCCTCTTTGACTACTGGGGCCAGGGAACCCTGGTC
 R   Q   G   G   D   G   N   Y   V   L   F   D   Y   W   G   Q   G   T   L   V

ACCGTCTCCTCAGGTGAGTCTGCTGTACTAAGCTT
 T   V   S   S
```

Each of the genes encoding Hu1A9 V$_L$1 and V$_L$2 was designed as an exon including a signal peptide, a splice donor signal, and appropriate restriction enzyme sites for subsequent cloning into a mammalian expression vector. The splice donor signal of the exons was derived from the human germline Jκ2 sequence. The signal peptide sequence in each of the humanized Hu1A9 V$_L$1 and V$_L$2 exons was derived from the corresponding mouse 1A9 V$_L$ sequence.

The nucleotide sequence (SEQ ID NO: 18) of the Hu1A9 V$_L$1 gene flanked by NheI and EcoRI sites (underlined) is shown in Table 11 along with the deduced amino acid sequence (SEQ ID NO: 19). The signal peptide sequence is in italic. The N-terminal amino acid residue (D) of the mature V$_L$ is double-underlined. CDR sequences according to the definition of Kabat et al. (1991) are underlined. The intron sequence is in italic.

TABLE 11

Nucleotide (SEQ ID NO: 18) and Amino Acid (SEQ ID NO: 19) Sequences of Humanized Hu1A9 V$_L$1 Gene

```
GCTAGCACCACCATGGAGTCACAGACTCAGGTCTTTGTGTACATGTTGCTGTGGTTGTCT
        M   E   S   Q   T   Q   V   F   V   Y   M   L   L   W   L   S

GGTGTTGATGGAGACATTCAGATGACCCAGTCTCCATCCTCCCTGTCCGCATCAGTCGGA
 G   V   D   G   D   I   Q   M   T   Q   S   P   S   S   L   S   A   S   V   G

GACAGGGTCACCATCACCTGCAAGGCCAGTCAGAATGTGGGTACTACTGTTGCCTGGTAT
 D   R   V   T   I   T   C   K   A   S   Q   N   V   G   T   T   V   A   W   Y

CAACAGAAACCAGGAAAAGCCCCTAAAGTCCTGATTTACTCCGCATCCTATCGGTACAGT
 Q   Q   K   P   G   K   A   P   K   V   L   I   Y   S   A   S   Y   R   Y   S
```

TABLE 11-continued

Nucleotide (SEQ ID NO: 18) and Amino Acid (SEQ ID NO: 19) Sequences of Humanized Hu1A9 V$_L$1 Gene

```
GGAGTCCCTTCACGCTTCAGTGGCAGTGGATCTGGGACAGATTTCACTCTCACCATCAGC
 G  V  P  S  R  F  S  G  S  G  S  G  T  D  F  T  L  T  I  S

AGTCTGCAGCCTGAAGACTTTGCAACTTATTACTGTCAGCAATATAACAGCTATCCATTC
 S  L  Q  P  E  D  F  A  T  Y  Y  C  Q  Q  Y  N  S  Y  P  F

ACGTTCGGCCAGGGGACAAAGTTGGAAATCAAACGTAAGTACTTTTTTCCGAATTC
 T  F  G  Q  G  T  K  L  E  I  K
```

The nucleotide sequence (SEQ ID NO: 20) of the Hu1A9 V$_L$2 gene flanked by NheI and EcoRI sites (underlined) is shown in Table 12 along with the deduced amino acid sequence (SEQ ID NO: 21). The signal peptide sequence is in italic. The N-terminal amino acid residue (D) of the mature V$_L$ is double-underlined. CDR sequences according to the definition of Kabat et al. (1991) are underlined. The intron sequence is in italic.

TABLE 12

Nucleotide (SEQ ID NO: 20) and Amino Acid (SEQ ID NO: 21) Sequences of Humanized 1A9 V$_L$2 Gene

```
GCTAGCACCACCATGGAGTCACAGACTCAGGTCTTTGTGTACATGTTGCTGTGGTTGTCT
         M  E  S  Q  T  Q  V  F  V  Y  M  L  L  W  L  S

GGTGTTGATGGAGACATTCAGATGACCCAGTCTCCATCCTCCCTGTCCGCATCAGTCGGA
 G  V  D  G  D  I  Q  M  T  Q  S  P  S  S  L  S  A  S  V  G

GACAGGGTCACCATCACCTGCAAGGCCAGTCAGAATGTGGGTACTACTGTTGCCTGGTAT
 D  R  V  T  I  T  C  K  A  S  Q  N  V  G  T  T  V  A  W  Y

CAACAGAAACCAGGAAAAGCCCCTAAAGTCCTGATTTACTCCGCATCCTATCGGTACAGT
 Q  Q  K  P  G  K  A  P  K  V  L  I  Y  S  A  S  Y  R  Y  S

GGAGTCCCTTCACGCTTCAGTGGCAGTGGATCTGGGACAGATTTCACTCTCACCATCAGC
 G  V  P  S  R  F  S  G  S  G  S  G  T  D  F  T  G  T  I  S

AGTCTGCAGCCTGAAGACTTTGCAACTTATTACTGTCAGCAATATAACAGCTATCCATTC
 S  L  Q  P  E  D  F  A  T  Y  Y  C  Q  Q  Y  N  S  Y  P  F

ACGTTCGGCCAGGGGACAAAGTTGGAAATCAAACGTAAGTACTTTTTTCCGAATTC
 T  F  G  Q  G  T  K  L  E  I  K
```

Generation of NS0 Stable Transfectants Producing Chimeric and Humanized 1A9 IgG1/κ Antibodies.

To obtain cell lines stably producing Ch1A9, Hu1A9-1 and Hu1A9-2 antibodies, the expression vectors pCh1A9, pHu1A9-1 and pHu1A9-2, respectively, were introduced into the chromosome of a mouse myeloma cell line NS0 (European Collection of Animal Cell Cultures, Salisbury, Wiltshire, UK). NS0 cells were grown in DME medium containing 10% FBS at 37° C. in a 7.5% CO$_2$ incubator. Stable transfection into NS0 was carried out by electroporation as described in Bebbington et al. (Bio/Technology 10: 169-175, 1992). Before transfection, each expression vector was linearized using FspI. Approximately 10$^7$ cells were transfected with 20 µg of linearized plasmid, suspended in DME medium containing 10% FBS, and plated into several 96-well plates. After 48 hr, selection media (DME medium containing 10% FBS, HT media supplement (Sigma, St. Louis, Mo.), 0.25 mg/ml xanthine and 1 µg/ml mycophenolic acid) was applied. Approximately 10 days after the initiation of selection, culture supernatants were assayed for antibody production.

Expression of Ch1A9, Hu1A9-1 and Hu1A9-2 antibodies was measured by sandwich ELISA. In a typical experiment, an ELISA plate was coated overnight at 4° C. with 100 µl/well of ½,000-diluted goat anti-human IgG Fcγ-chain-specific polyclonal antibody (Sigma) in PBS, washed with Wash Buffer (PBS containing 0.05% Tween 20), and blocked for 0.5 hr at room temperature with 300 µl/well of Block Buffer (PBS containing 2% Skim Milk and 0.05% Tween 20). After washing with Wash Buffer, 100 µl/well of samples appropriately diluted in ELISA Buffer (PBS containing 1% Skim Milk and 0.025% Tween 20) were applied to the ELISA plate. An appropriate humanized IgG1/κ antibody was used as a standard. After incubating the ELISA plate for 1 hr at room temperature and washing with Wash Buffer, bound antibodies were detected using 100 µl/well of ½,000-diluted HRP-conjugated goat anti-human kappa chain polyclonal antibody (SouthernBiotech). After incubating for 0.5 hr at room temperature and washing with Wash Buffer, color development was performed by adding 100 µl/well of ABTS substrate (bioWORLD, Dublin, Ohio). Color development was stopped by adding 100 µl/well of 2% oxalic acid. Absorbance was read at 405 nm. NS0 stable transfectants producing a high level of Ch1A9, Hu1A9-1 and Hu1A9-2 antibodies (NS0-Ch1A9 1C11, NS0-Hu1A9-1 3F9, and NS0-Hu1A9-2 3C9, respectively) were adapted to growth in serum-free media using Hybridoma-SFM.

The authenticity of heavy and light chains produced in NS0-Ch1A9 1C11, NS0-Hu1A9-1 3F9, and NS0-Hu1A9-2 3C9 was confirmed by cDNA sequencing. The obtained nucleotide sequence of the coding region for each of Ch1A9 heavy chain, Ch1A9 light chain, Hu1A9-1 heavy chain, Hu1A9-1 light chain, Hu1A9-2 heavy chain, and Hu1A9-2 light chain matched perfectly with the corresponding sequence in the pCh1A9, pHu1A9-1 or pHu1A9-2 vector (Table 13).

TABLE 13

Sequence of coding regions of pCh1A9 Heavy and Light Chains

| Description | Nucleotide Sequence | Amino Acid Sequence |
|---|---|---|
| Coding region of gamma-1 heavy chain in pCh1A9 | SEQ ID NO: 22 | SEQ ID NO: 23 |
| Coding region of kappa light chain in pCh1A9 | SEQ ID NO: 24 | SEQ ID NO: 25 |
| Coding region of gamma-1 heavy chain in pHu1A9-1 and pHu1A9-2 | SEQ ID NO: 26 | SEQ ID NO: 27 |
| Coding region of kappa light chain in pHu1A9-1 | SEQ ID NO: 28 | SEQ ID NO: 29 |
| Coding region of kappa light chain in pHu1A9-2 | SEQ ID NO: 30 | SEQ ID NO: 31 |

Example 9

Characterization of Ch1A9, Hu1A9-1 and Hu1A9-2 Antibodies

NS0-Ch1A9 1C11, NS0-Hu1A9-1 3F9, and NS0-Hu1A9-2 3C9 cells were grown in Hybridoma-SFM in a roller bottle to the density of about $10^6$/ml, fed with $\frac{1}{10}^{th}$ volume of 60 mg/ml of Ultrafiltered Soy Hydrolysate (Irvine Scientific, Santa Ana, Calif.) dissolved in SFM4MAb media (HyClone), and grown further until the cell viability became less than 50%. After centrifugation and filtration, culture supernatant was loaded onto a protein-A Sepharose column (HiTrap MABSelect SuRe, GE Healthcare, Piscataway, N.J.). The column was washed with PBS before the antibody was eluted with 0.1 M glycine-HCl (pH 3.0). After neutralization with 1 M Tris-HCl (pH 8), the buffer of eluted antibody was changed to PBS by dialysis. Antibody concentration was determined by measuring absorbance at 280 nm (1 mg/ml=1.4 OD). The yield was 8.2 mg for Ch1A9 (from 1000 ml culture supernatant), 7.7 mg for Hu1A9-1 (from 500 ml) and 10.8 mg for Hu1A9-2 (from 500 ml).

Figure 9:
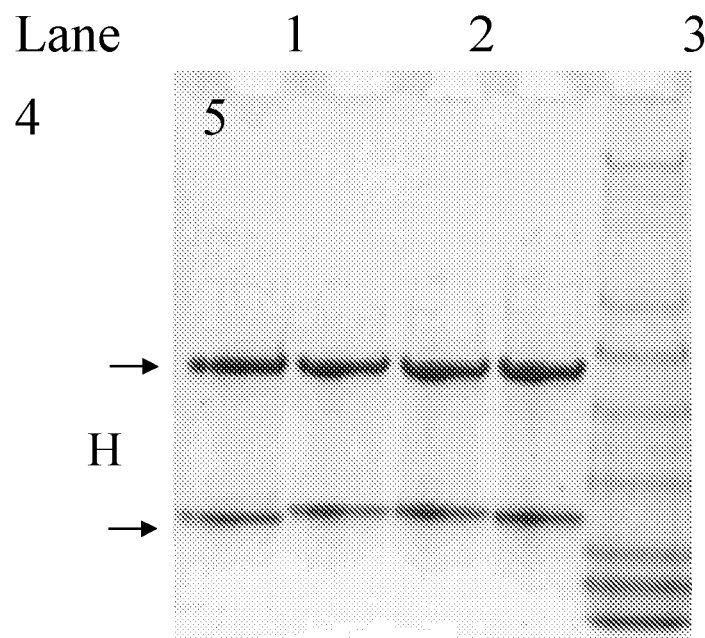
FIG. 9 is a SDS PAGE analysis of CT.RV 3D11E3 1A9 (lane 1), Ch1A9 (lane 2), Hu1A9-1 (lane 3) and Hu1A9-2 (lane 4) antibodies. Invitrogen SeeBlue® Plus2 Prestained Standard (Invitrogen, Grand Island, N.Y., USA; Cat # LC5925) was used as molecular weight standards (lane 5).

Purified Ch1A9, Hu1A9-1 and Hu1A9-2 were characterized by SDS-PAGE according to standard procedures. Analysis under reducing conditions indicated that each of the three antibodies is comprised of a heavy chain with a molecular weight of about 50 kDa and a light chain with a molecular weight of about 25 kDa (FIG. 9). The purity of each antibody appeared to be more than 95%.

Figure 10:
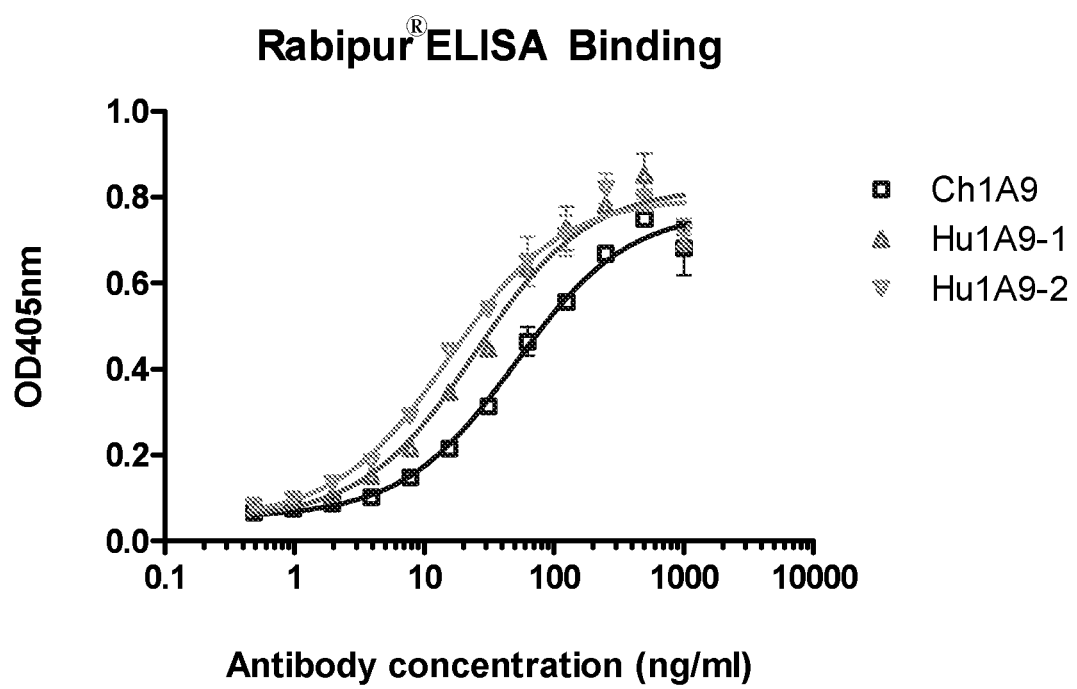
FIG. 10 is a graph of an ELISA analysis showing the binding of Ch1A9, Hu1A9-1 and Hu1A9-2 antibodies to Inactivated Rabies Virus Vaccine (Rabipur®, Chiron Behring GmbH & Co., Liederbach, Germany).
Figure 11:
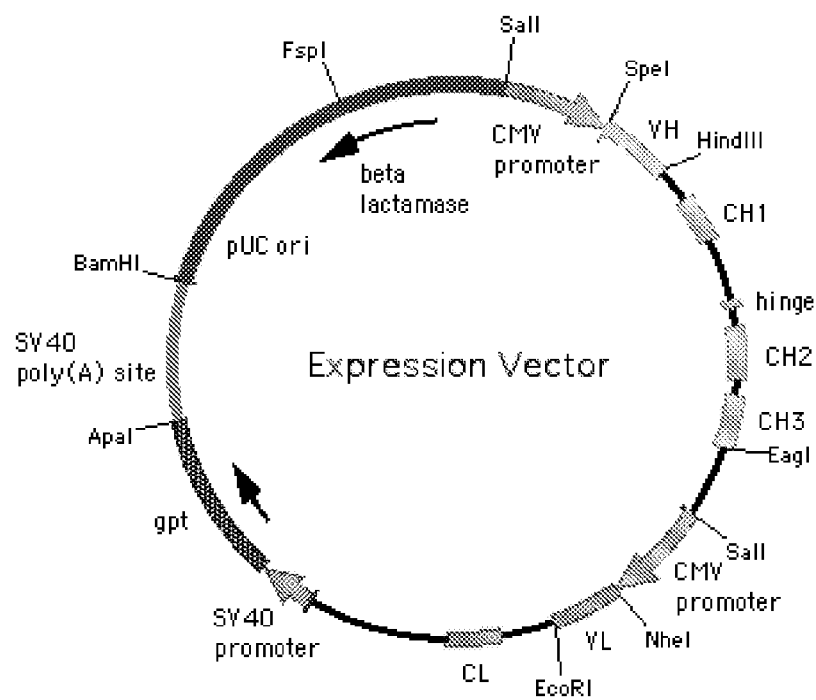
FIG. 11 is a schematic representation of the expression vector pCh2G11.

Antigen binding of Ch1A9, Hu1A9-1 and Hu1A9-2 antibodies was examined by ELISA. In a typical experiment, an ELISA plate was coated with 100 µl/well of $\frac{1}{500}$-diluted Inactivated Rabies Virus Vaccine (Rabipur®, Chiron Behring GmbH & Co., Liederbach, Germany) in 0.2 M sodium bicarbonate buffer (pH 9.4) overnight at 4° C., washed with Wash Buffer, and blocked for 0.5 hr at room temperature with 300 µl/well of Block Buffer. After washing with Wash Buffer, 100 µl/well of samples appropriately diluted in ELISA Buffer were applied to the ELISA plate. After incubating the ELISA plate for 1 hr at room temperature and washing with Wash Buffer, bound antibodies were detected using 100 µl/well of $\frac{1}{2,000}$-diluted HRP-conjugated goat anti-human IgG, Fcγ-chain-specific polyclonal antibody (Jackson ImmunoResearch, West Grove, Pa., USA). After incubating for 0.5 hr at room temperature and washing with Wash Buffer, color development was performed by adding 100 µl/well of ABTS substrate. Color development was stopped by adding 100 µl/well of 2% oxalic acid. Absorbance was read at 405 nm. $EC_{50}$ values calculated using GraphPad Prism (GraphPad Software, San Diego, Calif.) were 0.052 µg/ml for Ch1A9, 0.025 µg/ml for Hu1A9-1, and 0.016 µg/ml for Hu1A9-2 (FIG. 10). This result indicates that both Hu1A9-1 and Hu1A9-2 retain the antigen binding affinity of chimeric 1A9 antibody.

These results show that anti-rabies antibodies of the present technology specifically bind rabies virus glycoprotein, and that they are useful in methods related to such specific binding, including methods for detecting rabies virus glycoprotein in a sample, or treating or preventing rabies infection in a subject in need thereof and methods for providing post-exposure protection against rabies infection to a subject in need thereof.

Example 10

Generation of Humanized 2G11 Antibody

This Example describes the preparation of chimeric and humanized forms of the 7G11A3 2G11 antibody described in Examples 1-6 above.

Cloning and Sequencing of Mouse 2G11 Variable Region Genes.

Mouse CT.RV 7G11A3 2G11 (referred to as 2G11 in this Example) hybridoma cells were grown in Hybridoma-SFM (Invitrogen, Carlsbad, Calif.) containing 12% fetal bovine serum (FBS; HyClone, Logan, Utah) at 37° C. in a 7.5% $CO_2$ incubator. Total RNA was extracted from approximately $10^7$ hybridoma cells using TRIzol reagent (Invitrogen) according to the supplier's protocol. Oligo dT-primed cDNA for 5'-RACE was synthesized using the SMARTer RACE cDNA Amplification Kit (Clontech, Mountain View, Calif.) following the supplier's protocol. The variable region cDNAs for 2G11 heavy and light chains were amplified by polymerase chain reaction (PCR) with Phusion DNA polymerase (New England Biolabs, Beverly, Mass.) using 3' primers that anneal respectively to the mouse gamma-2a and kappa chain constant regions, and the 5'-RACE primer (Universal Primer A Mix or Nested Universal Primer A) provided in the SMARTer RACE cDNA Amplification Kit. For PCR amplification of heavy chain variable region ($V_H$), the 3' primer has sequence of SEQ ID NO: 1. For PCR amplification of light chain variable region ($V_L$), the 3' primer has the sequence of SEQ ID NO: 3. The amplified $V_H$ and $V_L$ cDNAs were cloned into the pCR4Blunt-TOPO vector (Invitrogen) for sequence determination. DNA sequencing was carried out at Tocore (Menlo Park, Calif.). Several heavy and light chain clones were sequenced and unique sequences homologous to typical mouse heavy and light chain variable regions were identified.

The nucleotide sequence (SEQ ID NO: 32) of mouse 2G11 $V_H$ cDNA is shown in Table 14 along with the deduced amino acid sequence (SEQ ID NO: 33). The signal peptide sequence is in italic. The N-terminal amino acid residue (E) of the mature $V_H$ is double-underlined. CDR sequences according to the definition of Kabat et al. (Sequences of Proteins of Immunological Interests, Fifth edition, NIH Publication No. 91-3242, U.S. Department of Health and Human Services, 1991) are underlined.

TABLE 14

Nucleotide (SEQ ID NO: 32) and amino acid (SEQ ID NO: 33) sequences of the Murine 2G11 V<sub>H</sub> cDNA

```
ATGAACTTTGTGCTCAGCCTGATTTTCCTTGCCCTCATTTTAAGAGGTGTCCCGTGTGAA
 M  N  F  V  L  S  L  I  F  L  A  L  I  L  R  G  V  P  C  E

GTGCAGCTGGTGGAGTCTGGGGGAGGCTTAGTGAAGCCTGGAGGGTCCCTGATACTCTCC
 V  Q  L  V  E  S  G  G  G  L  V  K  P  G  G  S  L  I  L  S

TGTGCAGCCTCAGGATTCACTTTCAGTGGCTTTGCCATGTCTTGGGTTCGCCAGACTCCG
 C  A  A  S  G  F  T  F  S  G  F  A  M  S  W  V  R  Q  T  P

GAGAAGAGGCTGGAGTGGGTCGCAACCATTAGTAGTGGTGGTACTTATACCTACTCTCCA
 E  K  R  L  E  W  V  A  T  I  S  S  G  G  T  Y  T  Y  S  P

GACAGTGTGATGGGTCGATTCACCATCTCCAGAGACAATGCCAAGAACACCCTGTACCTG
 D  S  V  M  G  R  F  T  I  S  R  D  N  A  K  N  T  L  Y  L

CAAATGAGCAGTCTGAGGTCTGAGGACACGGCCATGTATTACTGTGCAAGACGATTACGT
 Q  M  S  S  L  R  S  E  D  T  A  M  Y  Y  C  A  R  R  L  R

CGGAATTACTACTCTATGGACTACTGGGGTCAAGGAACCTCAGTCACCGTCTCCTCA
 R  N  Y  Y  S  M  D  Y  W  G  Q  G  T  S  V  T  V  S  S
```

The nucleotide sequence (SEQ ID NO: 34) of mouse 2G11 V<sub>L</sub> cDNA is shown in Table 15 along with the deduced amino acid sequence (SEQ ID NO: 35). Amino acid residues are shown in single letter code. The signal peptide sequence is in italic. The N-terminal amino acid residue (D) of the mature V<sub>L</sub> is double-underlined. CDR sequences according to the definition of Kabat et al. (1991) are underlined.

TABLE 15

Nucleotide (SEQ ID NO: 34) and amino acid (SEQ ID NO: 35) sequences of the Murine 2G11 V<sub>L</sub> cDNA

```
ATGAAGCTGCCTGTTCTGCTAGTGGTGCTGCTATTGTTCACGAGTCCAGCCTCAAGCAGT
 M  K  L  P  V  L  L  V  V  L  L  L  F  T  S  P  A  S  S  S

GATGTTGTTCTGACCCAAGCTCCACTCTCTCTGCCTGTCAATATTGGAGATCAAGCCTCT
 D  V  V  L  T  Q  A  P  L  S  L  P  V  N  I  G  D  Q  A  S

ATCTCTTGCAAGTCTACTAAGAGTCTTCTGAATAGTGATGGATTCACTTATTTGGACTGG
 I  S  C  K  S  T  K  S  L  L  N  S  D  G  F  T  Y  L  D  W

TACCTGCAGAAGCCAGGCCAGTCTCCACAGCTCCTAATATATTTGGTTTCTAATCGATTT
 Y  L  Q  K  P  G  Q  S  P  Q  L  L  I  Y  L  V  S  N  R  F

TCTGGAGTTCCAGACAGGTTCAGTGGCAGTGGGTCAGGAACAGATTTCACACTCAAGATC
 S  G  V  P  D  R  F  S  G  S  G  S  G  T  D  F  T  L  K  I

AGCAGAGTGGAGGCTGAGGATTTGGGAATTTATTTTTGCTTCCAGAGTAACTATCTTCCA
 S  R  V  E  A  E  D  L  G  I  Y  F  C  F  Q  S  N  Y  L  P

TTCACGTTCGGCTCGGGGACAAAGTTGGAAATAAAA
 F  T  F  G  S  G  T  K  L  E  I  K
```

Construction of Chimeric 2G11 IgG1/κ Antibody.

A gene encoding 2G11 V<sub>H</sub> was generated as an exon including a splice donor signal and appropriate flanking restriction enzyme sites by PCR using 2G11 V<sub>H</sub> cDNA as a template, 5'-GCAACTAGTACCACCATGAACTTTGT-GCTCAGC-3' (SEQ ID NO: 37) as a 5' primer, and 5'-GG-GAAGCTTGAGAGGCCATTCTTACCTGAG-GAGACGGTGACTGAGGT-3' (SEQ ID NO: 37) as a 3' primer. Nucleotide sequence (SEQ ID NO: 38) of the designed 2G11 V<sub>H</sub> gene flanked by SpeI and HindIII sites (underlined) is shown in Table 16 along with the deduced amino acid sequence (SEQ ID NO: 39). The signal peptide sequence is in italic. The N-terminal amino acid residue (E) of the mature V<sub>H</sub> is double-underlined. CDR sequences according to the definition of Kabat et al. (1991) are underlined. The intron sequence is in italic.

TABLE 16

Nucleotide (SEQ ID NO: 38) and amino acid (SEQ ID NO: 39) sequence of the Chimeric 2G11 V<sub>H</sub> Gene

```
ACTAGTACCACCATGAACTTTGTGCTCAGCCTGATTTTCCTTGCCCTCATTTTAAGAGGT
           M  N  F  V  L  S  L  I  F  L  A  L  I  L  R  G
```

TABLE 16-continued

Nucleotide (SEQ ID NO: 38) and amino acid (SEQ ID NO: 39) sequence of the Chimeric 2G11 V_H Gene

```
GTCCCGTGTGAAGTGCAGCTGGTGGAGTCTGGGGGAGGCTTAGTGAAGCCTGGAGGGTCC
 V  P  C  E  V  Q  L  V  E  S  G  G  G  L  V  K  P  G  G  S

CTGATACTCTCCTGTGCAGCCTCAGGATTCACTTTCAGTGGCTTTGCCATGTCTTGGGTT
 L  I  L  S  C  A  A  S  G  F  T  F  S  G  F  A  M  S  W  V

CGCCAGACTCCGGAGAAGAGGCTGGAGTGGGTCGCAACCATTAGTAGTGGTGGTACTTAT
 R  Q  T  P  E  K  R  L  E  W  V  A  T  I  S  S  G  G  T  Y

ACCTACTCTCCAGACAGTGTGATGGGTCGATTCACCATCTCCAGAGACAATGCCAAGAAC
 T  Y  S  P  D  S  V  M  G  R  F  T  I  S  R  D  N  A  K  N

ACCCTGTACCTGCAAATGAGCAGTCTGAGGTCTGAGGACACGGCCATGTATTACTGTGCA
 T  L  Y  L  Q  M  S  S  L  R  S  E  D  T  A  M  Y  Y  C  A

AGACGATTACGTCGGAATTACTACTCTATGGACTACTGGGGTCAAGGAACCTCAGTCACC
 R  R  L  R  R  N  Y  Y  S  M  D  Y  W  G  Q  G  T  S  V  T

GTCTCCTCAGGTGAGTCCTTAAAAGCTT
 V  S  S
```

Figure 13:
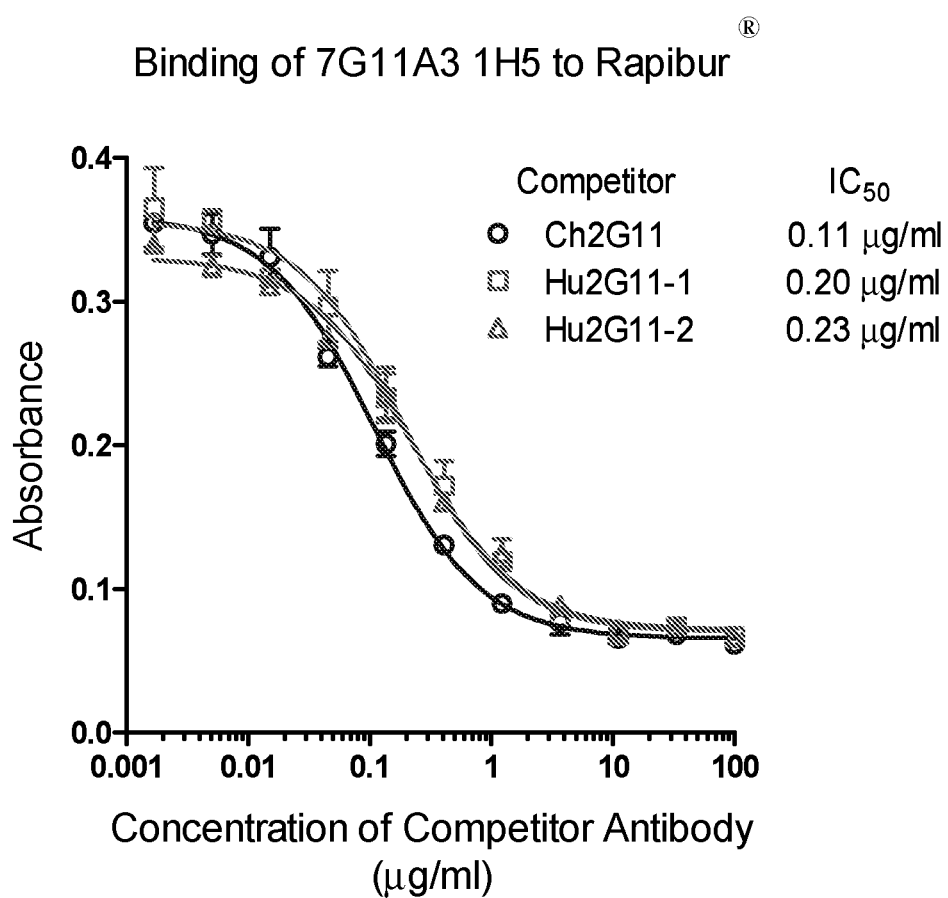
FIG. 13 is a graph of a competitive ELISA showing the binding of Ch2G11, Hu2G11-1 and Hu2G11-2 antibodies to Inactivated Rabies Virus Vaccine (Rabipur®, Chiron Behring GmbH & Co., Liederbach, Germany). An ELISA plate was coated with Rabipur®. Binding of mouse 7G11A3 1H5 to Rabipur® was examined in the presence of various concentrations of Ch2G11, Hu2G11-1 or Hu2G11-2. Bound mouse 7G11A3 1H5 was detected by HRP-conjugated goat anti-mouse IgG, Fcγ-chain-specific, human IgG-absorbed, polyclonal antibody.

Likewise, a gene encoding 2G11 V_L was generated as an exon including a splice donor signal and appropriate flanking restriction enzyme sites by PCR. Nucleotide sequence (SEQ ID NO: 40) of the designed 2G11 V_L gene flanked by NheI and EcoRI sites (underlined) is shown in Table 17 along with the deduced amino acid sequence (SEQ ID NO: 41). The signal peptide sequence is in italic. The N-terminal amino acid residue (D) of the mature V_L is double-underlined. CDR sequences according to the definition of Kabat et al. (1991) are underlined. The intron sequence is in italic.

antibody. The schematic structure of the resulting expression vector, pCh2G11, is shown in FIG. 13.

Design of Humanized 2G11 V_H and V_L Genes.

CDR sequences together with framework amino acid residues important for maintaining the CDR structure were grafted from 2G11 V_H and V_L into the corresponding selected human framework sequences. Human V_H sequences homologous to the 2G11 V_H frameworks were searched for within the GenBank database, and the V_H sequence encoded by the human U96282 cDNA (U96282 V_H) (GenBank accession

TABLE 17

Nucleotide (SEQ ID NO: 40) and amino acid sequence (SEQ ID NO: 41) of the Chimeric 2G11 V_L Gene

```
GCTAGCACCACCATGAAGCTGCCTGTTCTGCTAGTGGTGCTGCTATTGTTCACGAGTCCA
         M  K  L  P  V  L  L  V  V  L  L  L  F  T  S  P

GCCTCAAGCAGTGATGTTGTTCTGACCCAAGCTCCACTCTCTCTGCCTGTCAATATTGGA
 A  S  S  S  D  V  V  L  T  Q  A  P  L  S  L  P  V  N  I  G

GATCAAGCCTCTATCTCTTGCAAGTCTACTAAGAGTCTTCTGAATAGTGATGGATTCACT
 D  Q  A  S  I  S  C  K  S  T  K  S  L  L  N  S  D  G  F  T

TATTTGGACTGGTACCTGCAGAAGCCAGGCCAGTCTCCACAGCTCCTAATATATTTGGTT
 Y  L  D  W  Y  L  Q  K  P  G  Q  S  P  Q  L  L  I  Y  L  V

TCTAATCGATTTTCTGGAGTTCCAGACAGGTTCAGTGGCAGTGGGTCAGGAACAGATTTC
 S  N  R  F  S  G  V  P  D  R  F  S  G  S  G  S  G  T  D  F

ACACTCAAGATCAGCAGAGTGGAGGCTGAGGATTTGGGAATTTATTTTTGCTTCCAGAGT
 T  L  K  I  S  R  V  E  A  E  D  L  G  I  Y  F  C  F  Q  S

AACTATCTTCCATTCACGTTCGGCTCGGGGACAAAGTTGGAAATAAAACGTAAGTAGACT
 N  Y  L  P  F  T  F  G  S  G  T  K  L  E  I  K

TTTGCGAATTC
```

The splice donor signals of the 2G11 V_H and V_L exons were derived from the mouse germline JH2 and Jκ4 sequences, respectively. PCR-amplified fragments were gel-purified using NucleoSpin Extraction II Kit (Macherey-Nagel, Bethlehem, Pa.) and cloned into the pCR4Blunt-TOPO vector for sequence confirmation. The correct V fragments were digested with SpeI and HindIII (for V_H) or NheI and EcoRI (for V_L), gel-purified and cloned into a mammalian expression vector carrying human gamma-1 and kappa constant regions for production of chimeric 2G11 (Ch2G11) IgG1/κ number; Rassenti and Kipps, J. Exp. Med. 185:1435-1445, 1997) was chosen as an acceptor for humanization. The CDR sequences of 2G11 V_H were transferred to the corresponding positions of U96282 V_H. No substitution of human framework amino acid residues was predicted to be needed to maintain the CDR structure.

While the three-dimensional model of the mouse 2G11 variable regions indicated that an amino acid residue at position 19 of V_H is located away from the CDR and should not affect the formation of the CDR structure, the presence of an isoleucine residue at this position, rather than a typical lysine or arginine residue, is unusual and could influence the functional and/or biochemical nature of the antibody. The second humanized $V_H$ was therefore designed in which an arginine residue in Hu2G11 $V_H$ 1 at position 19 was replaced by an isoleucine residue.

Based on the homology search with the 2G11 $V_L$ framework sequences, the human Vκ region encoded by the X72466 cDNA (X72466 $V_L$) (GenBank accession number; Klein et al., Eur. J. Immunol. 23:3248-3262, 1993) was chosen as an acceptor for humanization. CDR sequences of 2G11 $V_L$ were first transferred to the corresponding positions of X72466 $V_L$. No substitution of human framework amino acids was predicted to be needed to maintain the CDR structure.

Construction of Humanized 2G11 $V_H$ and $V_L$ Genes.

Each of the genes encoding Hu2G11 $V_H$1 and $V_H$2 was designed as an exon including a signal peptide, a splice donor signal, and flanking SpeI and HindIII sites for subsequent cloning into a mammalian expression vector. The splice donor signal used in the Hu2G11 $V_H$1 and $V_H$2 exons was derived from the human germline JH3 sequence. Since the signal peptide encoded by the mouse 2G11 $V_H$ gene was predicted to be suboptimal for precise cleavage by the SIG-Pred signal peptide prediction software, the signal peptide sequence of the human U96282 $V_H$ gene was used in Hu2G11 $V_H$1 and $V_H$2.

A gene encoding Hu2G11 $V_L$ was designed as an exon including a signal peptide, a splice donor signal, and flanking NheI and EcoRI sites for subsequent cloning into a mammalian expression vector. The splice donor signal was derived from the human germline Jκ4 sequence. The signal peptide encoded by the mouse 2G11 $V_L$ gene was predicted to be suboptimal for precise cleavage by the SIG-Pred signal peptide prediction software, so that the signal peptide sequence of the human X72466 $V_L$ gene was used in Hu2G11 $V_L$.

The Hu2G11 $V_H$1, $V_H$2 and $V_L$ genes were constructed by GenScript USA (Piscataway, N.J.). After digestion with SpeI and HindIII (for $V_H$) or NheI and EcoRI (for $V_L$), Hu2G11 $V_H$1, $V_H$2 and $V_L$ genes were subcloned into corresponding sites in a mammalian expression vector for antibody production in the human IgG1/κ form. The resultant expression vector, pHu2G11-1, expresses a humanized antibody containing Hu2G11 $V_H$1 and $V_L$ (Hu2G11-1). Likewise, pHu2G11-2 expresses a humanized antibody containing Hu2G11 $V_H$2 and $V_L$ (Hu2G11-2).

The nucleotide sequence (SEQ ID NO: 42) of the Hu2G11 $V_H$2 (also called $V_H$R19I) gene flanked by SpeI and HindIII sites (underlined) is shown in Table 18 along with the deduced amino acid sequence (SEQ ID NO: 43). The signal peptide sequence is in italic. The N-terminal amino acid residue (E) of the mature $V_H$ is double-underlined. CDR sequences according to the definition of Kabat et al. (1991) are underlined. The boxed amino acid location indicates the difference between Hu2G11 $V_H$1 and $V_H$2. The intron sequence is in italic.

TABLE 18

Nucleotide (SEQ ID NO: 42) and amino acid sequence (SEQ ID NO: 43) of the Humanized 2G11 $V_H$ Gene

```
ACTAGTACCACCATGGAATTGGGGCTGAGCTGGGTTTTCCTTGTTGCTATTCTGGAAGGC
         M  E  L  G  L  S  W  V  F  L  V  A  I  L  E  G

GTCCAGTGTGAAGTGCAGCTCGTGGAGTCTGGGGGAGGCCTCGTCCAGCCTGGGGGCTCC
 V  Q  C  E  V  Q  L  V  E  S  G  G  G  L  V  Q  P  G  G  S

CTGATCCTCTCCTGTGCAGCCTCTGGATTCACCTTTAGTGGCTTTGCCATGAGCTGGGTC
 L  I  L  S  C  A  A  S  G  F  T  F  S  G  F  A  M  S  W  V

CGCCAGGCTCCAGGGAAGGGGCTCGAGTGGGTTGCCACCATTAGTAGTGGCGGAACTTAT
 R  Q  A  P  G  K  G  L  E  W  V  A  T  I  S  S  G  G  T  Y

ACCTACTCTCCAGACTCTGTGATGGGCCGATTCACCATCTCCAGAGACAACGCCAAGAAC
 T  Y  S  P  D  S  V  M  G  R  F  T  I  S  R  D  N  A  K  N

TCACTGTATCTGCAAATGAACAGCCTGAGAGCCGAGGACACAGCTGTGTATTACTGTGCC
 S  L  Y  L  Q  M  N  S  L  R  A  E  D  T  A  V  Y  Y  C  A

AGACGACTGCGTCGGAATTACTACTCTATGGACTACTGGGGCCAAGGGACAATGGTCACC
 R  R  L  R  R  N  Y  Y  S  M  D  Y  W  G  Q  G  T  M  V  T

GTCTCCTCAGGTAAGATGGGCTTTCCTAAGCTT
 V  S  S
```

The nucleotide sequence (SEQ ID NO: 44) of the Hu2G11 $V_L$ gene flanked by NheI and EcoRI sites (underlined) is shown in Table 19 along with the deduced amino acid sequence (SEQ ID NO: 45). The signal peptide sequence is in italic. The N-terminal amino acid residue (D) of the mature $V_L$ is double-underlined. CDR sequences according to the definition of Kabat et al. (1991) are underlined. The intron sequence is in italic.

TABLE 19

Nucleotide (SEQ ID NO: 44) and amino acid sequence (SEQ ID NO: 45) of the Humanized 2G11 $V_L$ Gene

```
GCTAGCACCACCATGAGGCTCCCTGCTCAGCTCCTGGGGCTGCTGATGCTCTGGGTCTCT
      M  R  L  P  A  Q  L  L  G  L  L  M  L  W  V  S
```

TABLE 19-continued

Nucleotide (SEQ ID NO: 44) and amino acid sequence (SEQ ID NO: 45)
of
the Humanized 2G11 V_L Gene

```
GGATCCAGTGGGGATATTGTGATGACTCAGTCTCCACTCTCCCTGCCCGTCACCCCTGGA
 G  S  S  G  D  I  V  M  T  Q  S  P  L  S  L  P  V  T  P  G

GAGCCTGCCTCCATCTCCTGCAAGTCTACTAAGAGCCTCCTGAATAGTGATGGATTCACT
 E  P  A  S  I  S  C  K  S  T  K  S  L  L  N  S  D  G  F  T

TATTTGGATTGGTACCTGCAGAAGCCAGGGCAGTCTCCACAGCTCCTGATCTATTTGGTT
 Y  L  D  W  Y  L  Q  K  P  G  Q  S  P  Q  L  L  I  Y  L  V

TCTAATCGGTTTTCCGGGGTCCCAGACAGATTCAGTGGCAGTGGATCAGGCACAGATTTT
 S  N  R  F  S  G  V  P  D  R  F  S  G  S  G  T  D  F

ACACTGAAAATCAGCAGAGTGGAGGCTGAGGATGTTGGCGTTTATTACTGCTTCCAAAGT
 T  L  K  I  S  R  V  E  A  E  D  V  G  V  Y  Y  C  F  Q  S

AACTATCTTCCTTTCACTTTCGGCGGCGGAACCAAAGTCGAGATCAAACGTAAGTGCACT
 N  Y  L  P  F  T  F  G  G  G  T  K  V  E  I  K

TTCCTAGAATTC
```

Generation of NS0 Stable Transfectants Producing Chimeric and Humanized 2G11 IgG1/κ Antibodies.

To obtain cell lines stably producing Ch2G11, Hu2G11-1 and Hu2G11-2 antibodies, the expression vectors pCh2G11, pHu2G11-1 and pHu2G11-2, respectively, were introduced into the chromosome of a mouse myeloma cell line NS0 (European Collection of Animal Cell Cultures, Salisbury, Wiltshire, UK). NS0 cells were grown in DME medium containing 10% FBS at 37° C. in a 7.5% $CO_2$ incubator. Stable transfection into NS0 was carried out by electroporation as described in Bebbington et al. (Bio/Technology 10: 169-175, 1992). Before transfection, each expression vector was linearized using FspI. Approximately $10^7$ cells were transfected with 20 μg of linearized plasmid, suspended in DME medium containing 10% FBS, and plated into several 96-well plates. After 48 hr, selection media (DME medium containing 10% FBS, HT media supplement (Sigma, St. Louis, Mo.), 0.25 mg/ml xanthine and 1 μg/ml mycophenolic acid) was applied. Approximately 10 days after the initiation of selection, culture supernatants were assayed for antibody production.

Expression of Ch2G11, Hu2G11-1 and Hu2G11-2 antibodies was measured by sandwich ELISA. In a typical experiment, an ELISA plate was coated overnight at 4° C. with 100 μl/well of ½,000-diluted goat anti-human IgG Fcγ-chain-specific polyclonal antibody (Sigma) in PBS, washed with Wash Buffer (PBS containing 0.05% Tween 20), and blocked for 0.5 hr at room temperature with 300 μl/well of Block Buffer (PBS containing 2% Skim Milk and 0.05% Tween 20). After washing with Wash Buffer, 100 μl/well of samples appropriately diluted in ELISA Buffer (PBS containing 1% Skim Milk and 0.025% Tween 20) were applied to the ELISA plate. An appropriate humanized IgG1/κ antibody was used as a standard. After incubating the ELISA plate for 1 hr at room temperature and washing with Wash Buffer, bound antibodies were detected using 100 μl/well of ½,000-diluted HRP-conjugated goat anti-human kappa chain polyclonal antibody (SouthernBiotech, Birmingham, Ala., USA). After incubating for 0.5 hr at room temperature and washing with Wash Buffer, color development was performed by adding 100 μl/well of ABTS substrate (bioWORLD, Dublin, Ohio). Color development was stopped by adding 100 μl/well of 2% oxalic acid. Absorbance was read at 405 nm. NS0 stable transfectants producing a high level of Ch2G11, Hu2G11-1 and Hu2G11-2 antibodies (NS0-Ch2G11 1E7, NS0-Hu2G11-1 1E5, and NS0-Hu2G11-2 1A7, respectively) were adapted to growth in serum-free media using Hybridoma-SFM.

The authenticity of heavy and light chains produced in NS0-Ch2G11 1E7, NS0-Hu2G11-1 1E5, and NS0-Hu2G11-2 1A7 was confirmed by cDNA sequencing. The obtained nucleotide sequence of the coding region for each of Ch2G11 heavy chain, Ch2G11 light chain, Hu2G11-1 heavy chain, Hu2G11-1 light chain, Hu2G11-2 heavy chain, and Hu2G11-2 light chain are shown in Tables 24-28. The sequences matched perfectly with the corresponding sequence in the pCh2G11, pHu2G11-1 or pHu2G11-2 vector.

TABLE 20

Sequence of coding regions of pCh2G11 Heavy and Light Chains

| Description | Nucleotide Sequence | Amino Acid Sequence |
|---|---|---|
| Coding region of gamma-1 heavy chain in pCh2G11 | SEQ ID NO: 46 | SEQ ID NO: 47 |
| Coding region of kappa light chain in pCh2G11 | SEQ ID NO: 48 | SEQ ID NO: 49 |
| Coding region of gamma-1 heavy chain in pCh2G11-1 | SEQ ID NO: 50 | SEQ ID NO: 51 |
| Coding region of gamma-1 heavy chain in pCh2G11-2 | SEQ ID NO: 52 | SEQ ID NO: 53 |
| Coding region of kappa light chain in pCh2G11-1 and pCh2G11-2 | SEQ ID NO: 54 | SEQ ID NO: 55 |

Example 11

Purification of Ch2G11, Hu2G11-1 and Hu2G11-2 Antibodies

NS0-Ch2G11 1E7, NS0-Hu2G11-1 1E5, and NS0-Hu2G11-2 1A7 cells were grown in Hybridoma-SFM in a roller bottle to the density of about $10^6$/ml, fed with $\frac{1}{10}^{th}$ volume of 60 mg/ml of Ultrafiltered Soy Hydrolysate (Irvine Scientific, Santa Ana, Calif.) dissolved in SFM4MAb media (HyClone), and grown further until the cell viability became less than 50%. After centrifugation and filtration, culture supernatant was loaded onto a protein-A Sepharose column (HiTrap MABSelect SuRe, GE Healthcare, Piscataway, N.J.). The column was washed with PBS before the antibody was eluted with 0.1 M glycine-HCl (pH 3.0). After neutralization with 1 M Tris-HCl (pH 8), the buffer of eluted antibody was changed to PBS by dialysis. Antibody concentration was determined by measuring absorbance at 280 nm (1 mg/ml=1.4 OD). The yield was 2.8 mg for Ch2G11 (from 500 ml culture supernatant), 3.4 mg for Hu2G11-1 (from 500 ml) and 1.1 mg for Hu2G11-2 (from 500 ml).

Figure 12:
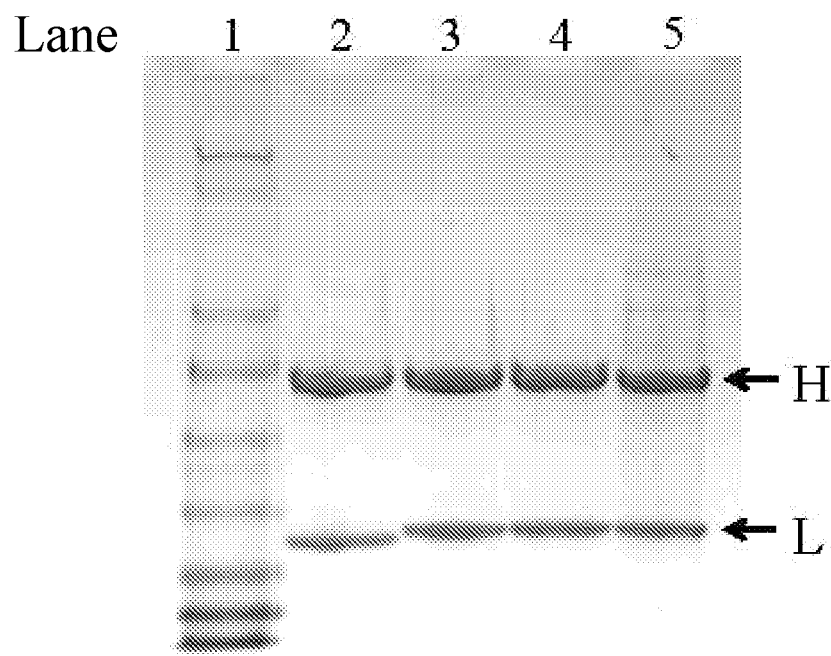
FIG. 12 is SDS PAGE analysis of CT.RV 7G11A3 1H5 (lane 2), Ch2G11 (lane 3), Hu2G11-1 (lane 4) and Hu2G11-2 (lane 5) antibodies. Samples (5 μg each) were run on a 4-20% SDS PAGE gel under reducing conditions. Invitrogen SeeBlue® Plus2 Prestained Standard (Invitrogen, Grand Island, N.Y., USA; Cat # LC5925) was used as molecular weight standards (lane 1). H and L denote the position of heavy and light chains, respectively.

Purified Ch2G11, Hu2G11-1 and Hu2G11-2 antibodies were characterized by SDS-PAGE according to standard procedures. Analysis under reducing conditions indicated that each of the three antibodies is comprised of a heavy chain with a molecular weight of about 50 kDa and a light chain with a molecular weight of about 25 kDa (FIG. 12). The purity of each antibody appeared to be more than 90%.

Example 12

Characterization of Ch2G11, Hu2G11-1 and Hu2G11-2 Antibodies

Antigen binding of Ch2G11, Hu2G11-1 and Hu2G11-2 antibodies was examined by a competitive binding ELISA. An ELISA plate was coated with 100 μl/well of 1/200-diluted Inactivated Rabies Virus Vaccine (Rabipur®, Chiron Behring GmbH & Co., Liederbach, Germany) in 0.2 M sodium bicarbonate buffer (pH 9.4) overnight at 4° C., washed with Wash Buffer (PBS), and blocked with 300 μl/well of Block Buffer (3% BSA PBS) for 0.5 hr at room temperature. After washing with Wash Buffer, a mixture of mouse 7G11A3 1H5 antibody (0.2 μg/ml; supplied by Asia Vision) and competitor antibody (Ch2G11, Hu2G11-1 or Hu2G11-2; starting at a final concentration of 100 μg/ml and serial 3-fold dilutions) in ELISA buffer was applied at 100 μl/well in duplicate. After incubating the ELISA plate for 1 hr at room temperature and washing with Wash Buffer, bound mouse 7G11A3 1H5 antibodies were detected using 100 μl/well of 1/2,000-diluted HRP-conjugated goat anti-mouse IgG, Fcγ-chain-specific, human IgG-absorbed, polyclonal antibody (Jackson ImmunoResearch, West Grove, Pa.). After incubating for 0.5 hr at room temperature and washing with Wash Buffer, color development was performed by adding 100 μl/well of ABTS substrate and stopped by 100 μl/well of 2% oxalic acid. Absorbance was read at 405 nm. $IC_{50}$ values calculated using GraphPad Prism (GraphPad Software, San Diego, Calif.) were 0.11 μg/ml for Ch2G11, 0.20 μg/ml for Hu2G11-1, and 0.23 μg/ml for Hu2G11-2 (FIG. 13). This result indicates that both Hu2G11-1 and Hu2G11-2 retain the antigen binding affinity of mouse 2G11 antibody.

Figure 14A:
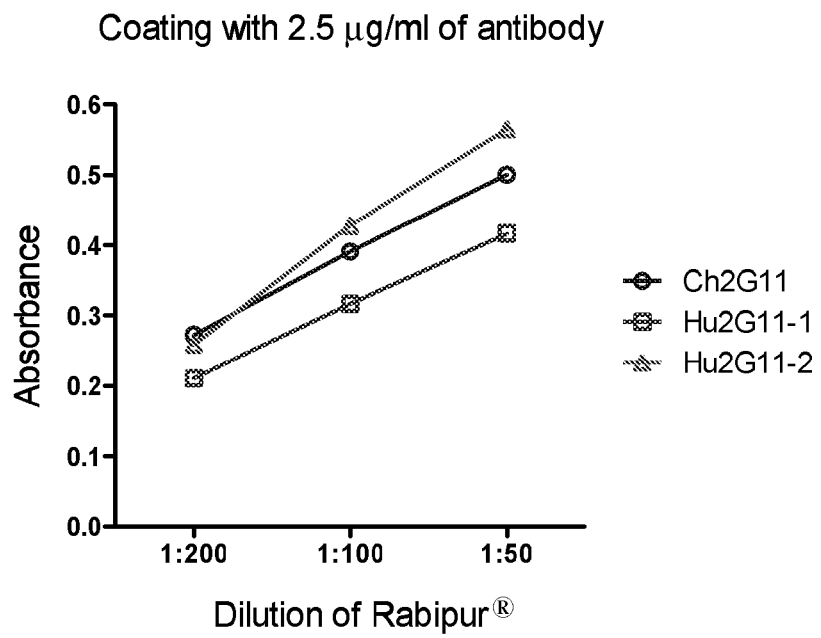
FIGS. 14A and 14B are graphs of an ELISA analysis of the binding of Ch2G11, Hu2G11-1 and Hu2G11-2 antibodies to Inactivated Rabies Virus Vaccine (Rabipur®, Chiron Behring GmbH & Co., Liederbach, Germany). ELISA plates were coated with 2.5 μg/ml (FIG. 14A) or 1.0 μg/ml (FIG. 14B) Ch2G11, Hu2G11-1 or Hu2G11-2. Rabipur® captured by coated antibodies was detected by HRP-conjugated 3D10.
Figure 14B:
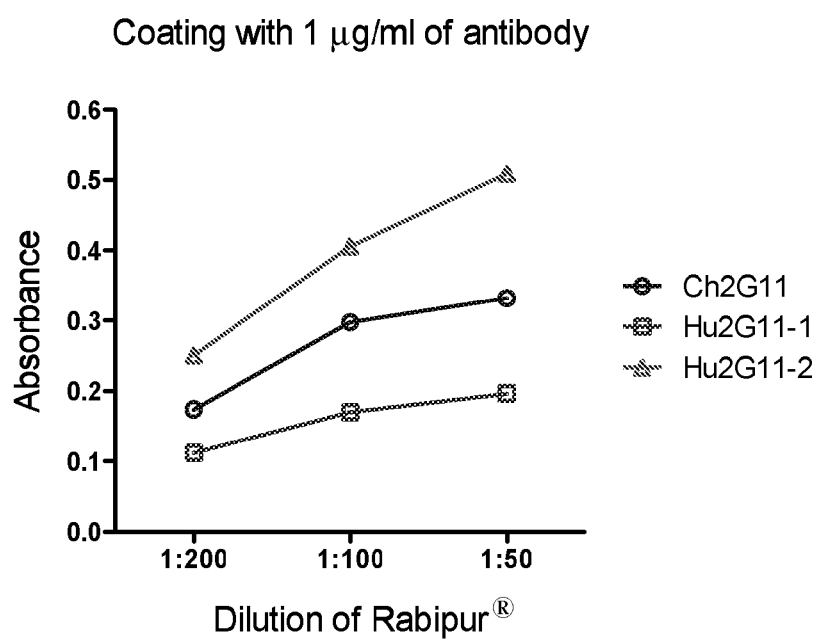
Figure 15A:
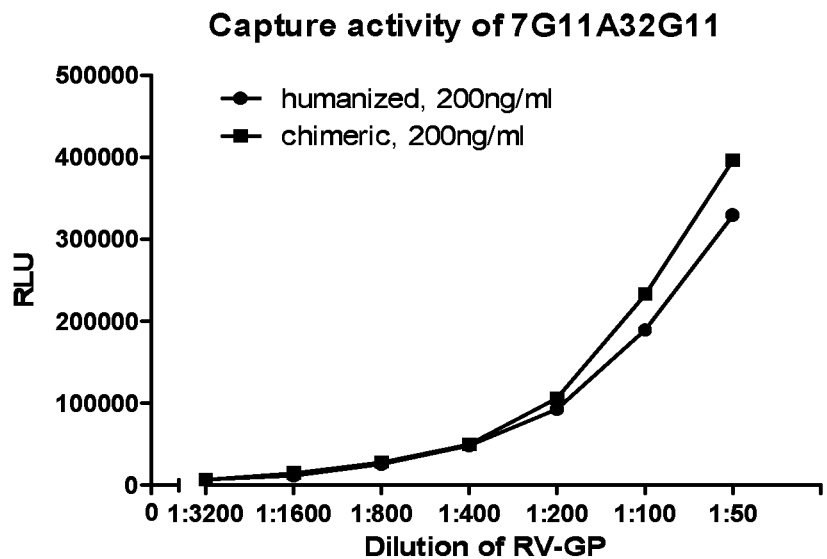
Figure 15B:
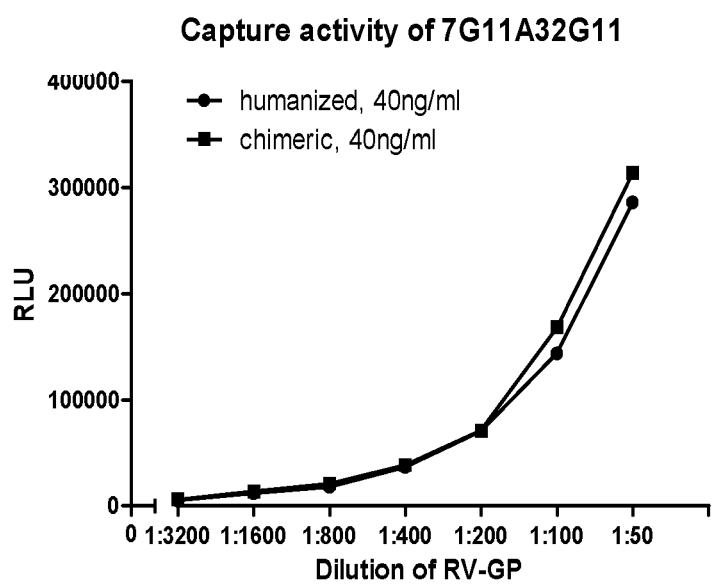
Figure 15E:
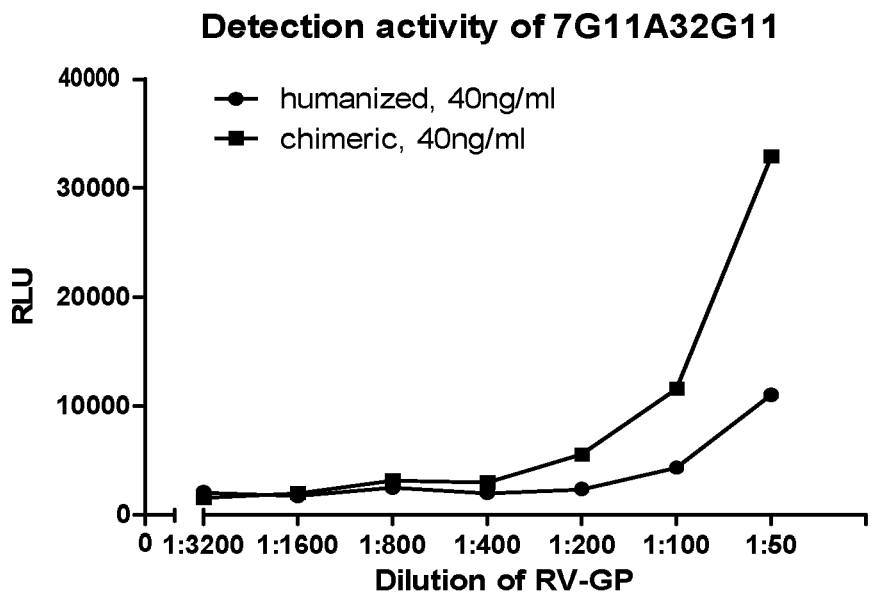
Figure 15F:
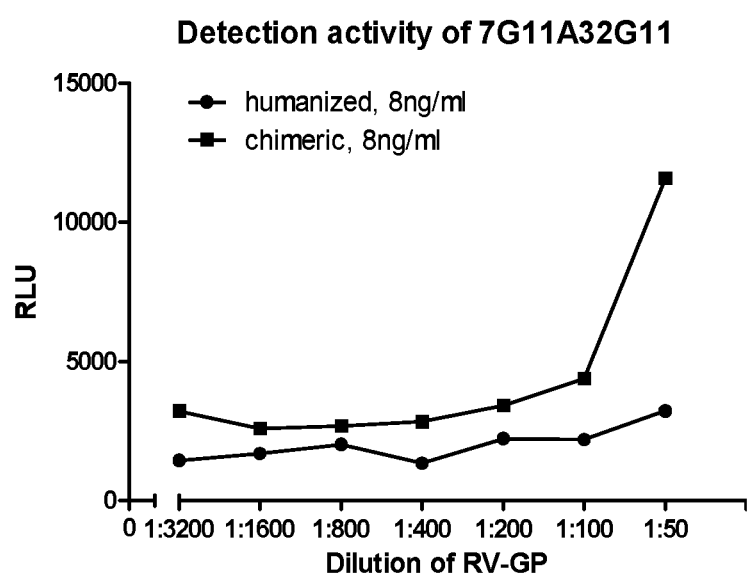
Figure 16A:
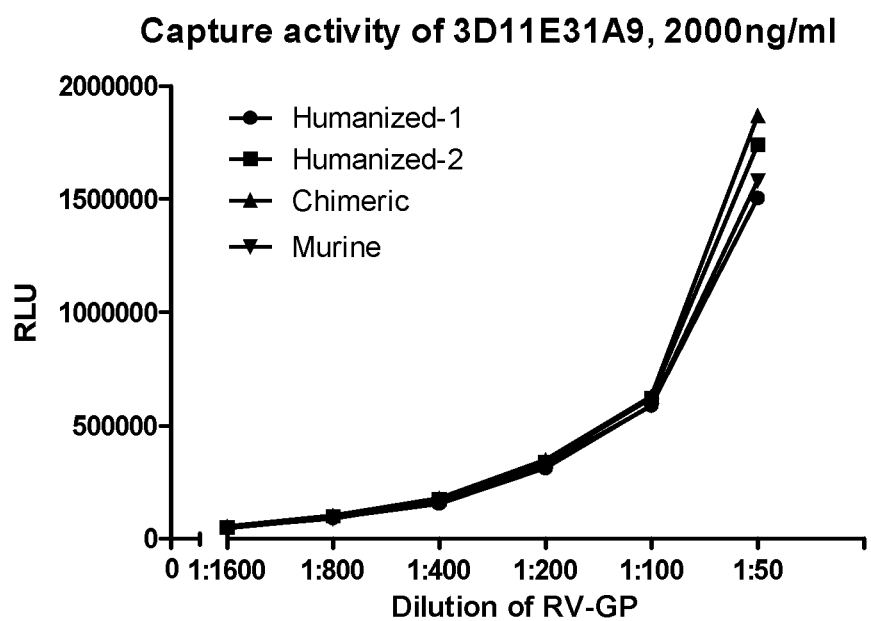
FIGS. 16A-16J are a series of binding curves of the humanized, chimeric, and murine 1A9 RVNAs to RV glycoprotein as determined by CLEIA. The chimeric and humanized 1A9 were used as capture and detection antibody, respectively. The glycoprotein was diluted to 1:50, 1:100, 1:200, 1:400, 1:800 and 1:1600 and then added in the micro-plate. Murine RV 3D10-HRP and mouse anti-human IgG-HRP were used as the enzyme conjugate. Related luminescence unit (RLU) represents the chemiluminescence signal.
Figure 16B:
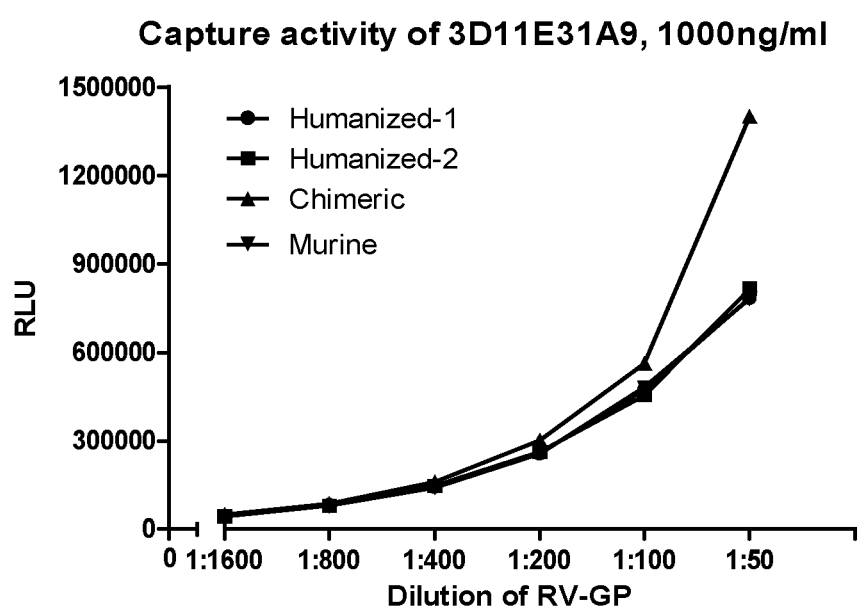
Figure 16C:
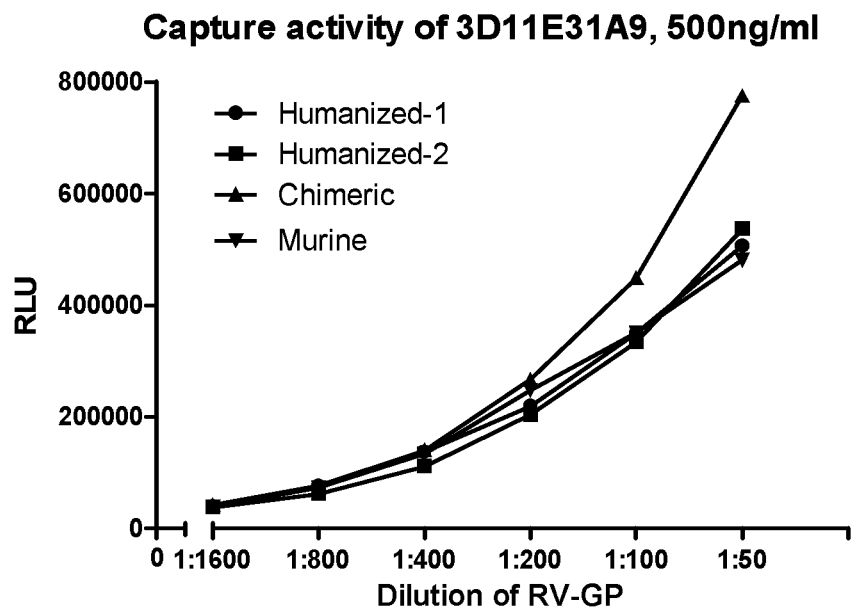
Figure 16D:
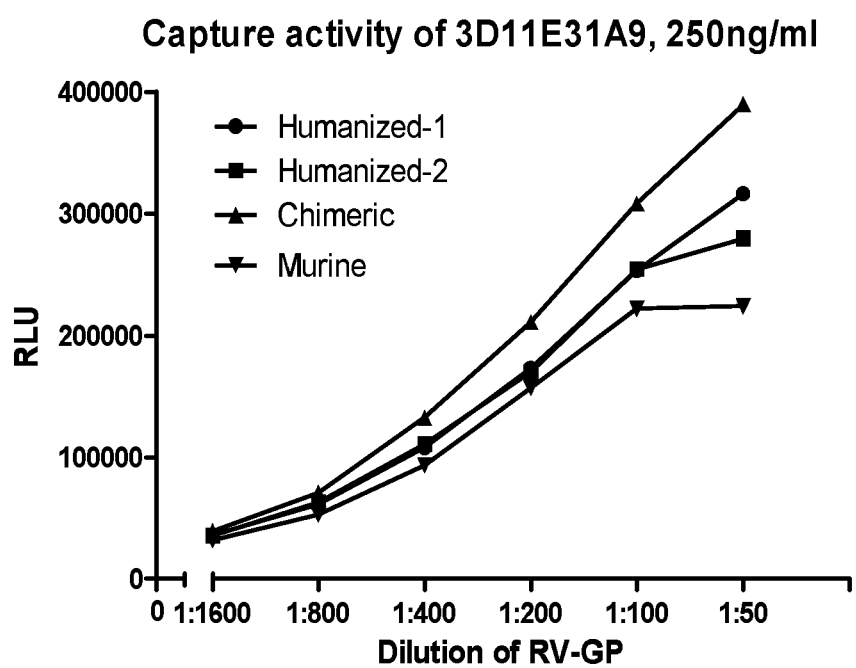
Figure 16E:
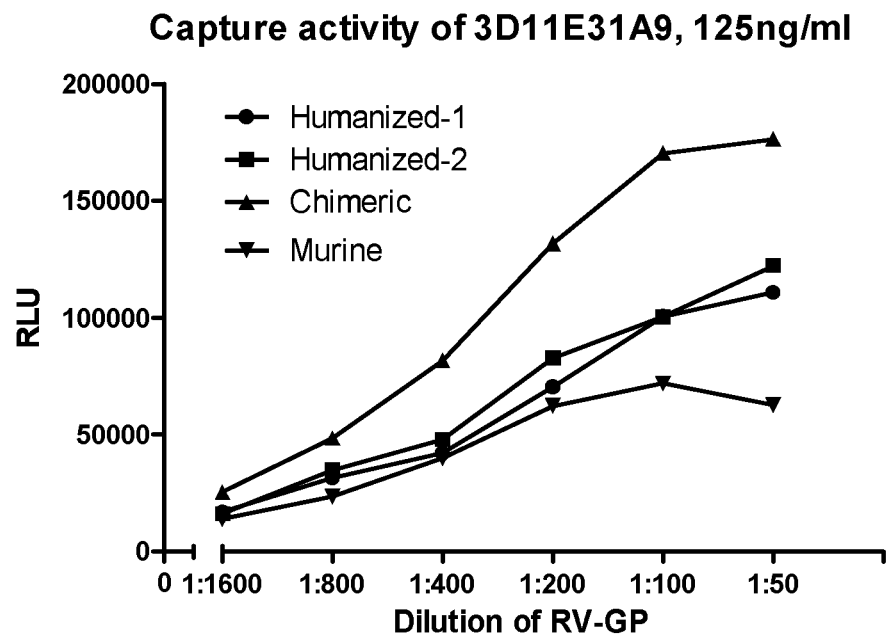
Figure 16F:
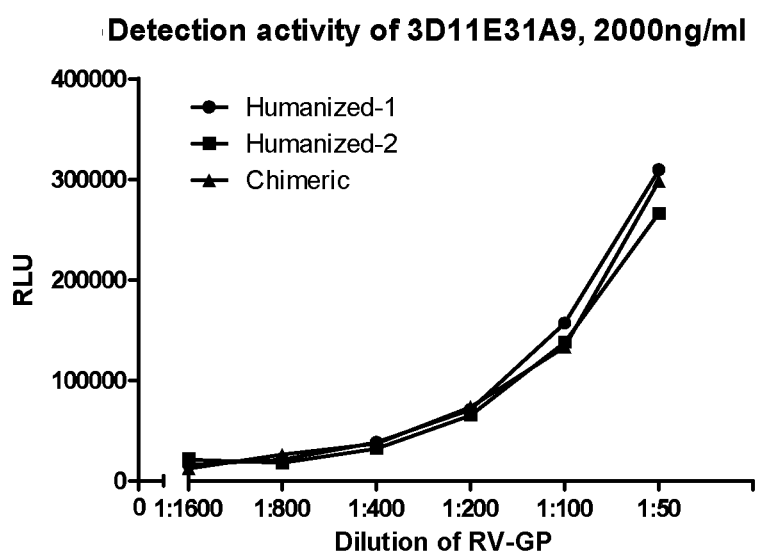
Figure 16G:
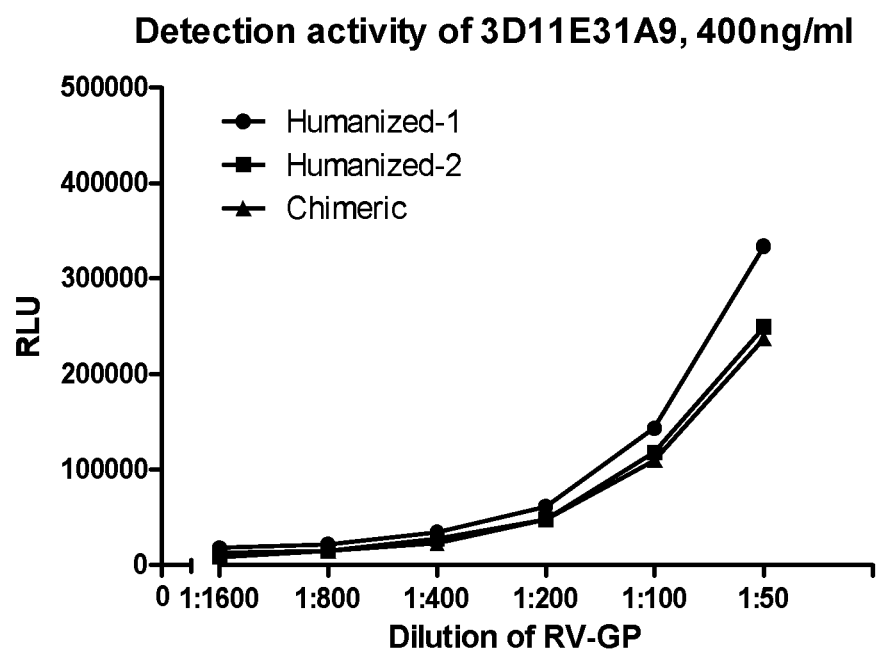
Figure 16H:
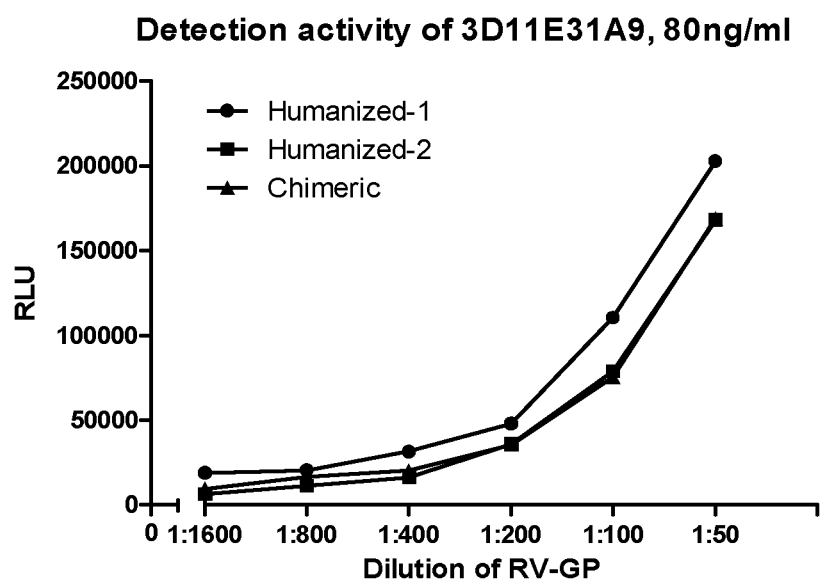
Figure 16I:
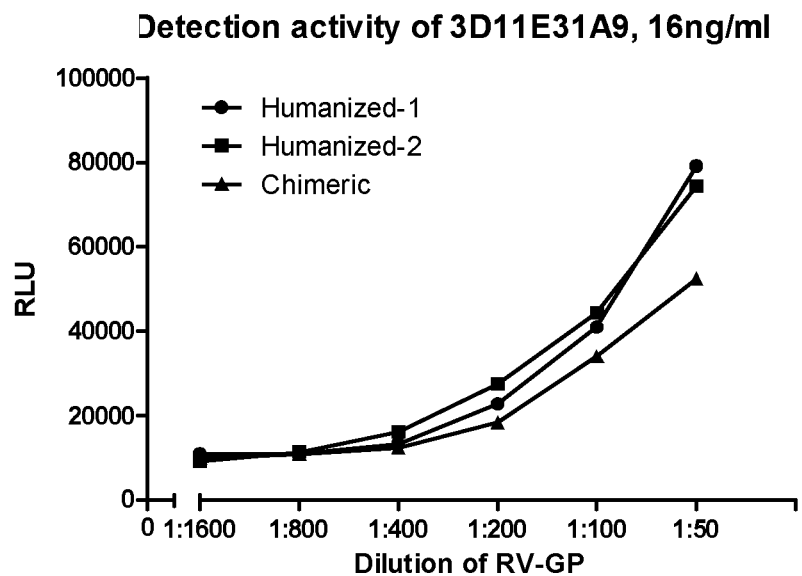
Figure 16J:
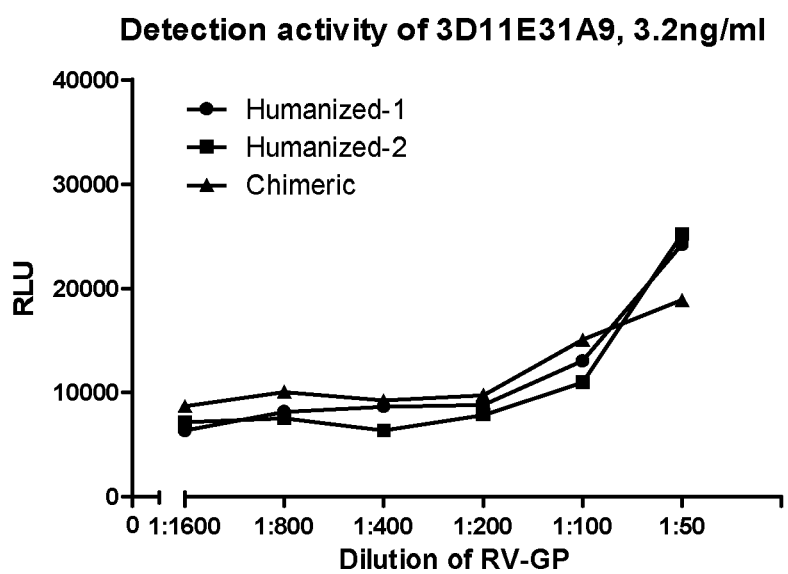
Figure 17A:
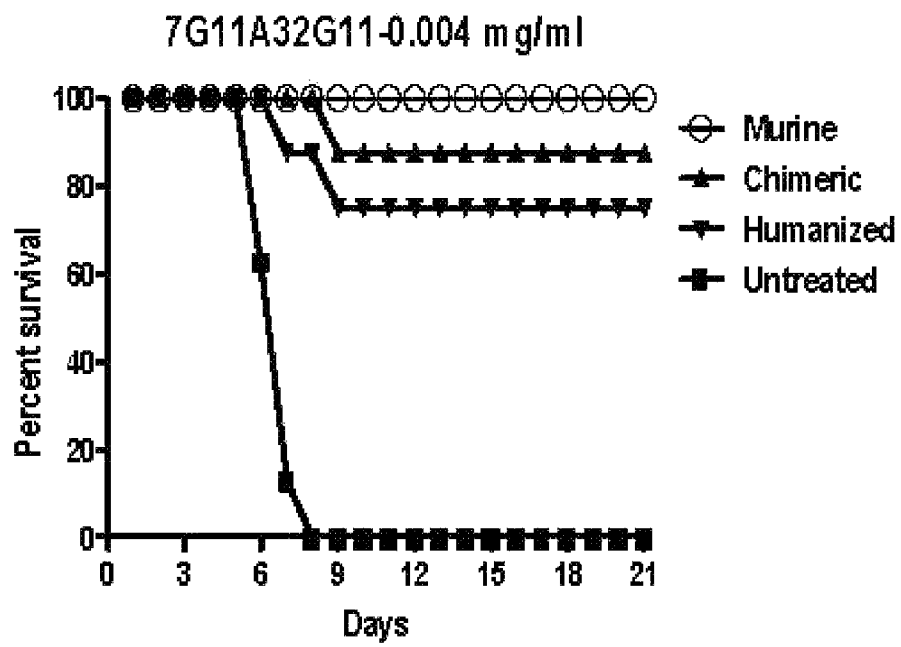
FIGS. 17A-17F are a series of graphs showing the percent survival of BALB/C mice in MNT experiments. Kaplan-Meier survival curves are shown for days 0 to 21.
Figure 17B:
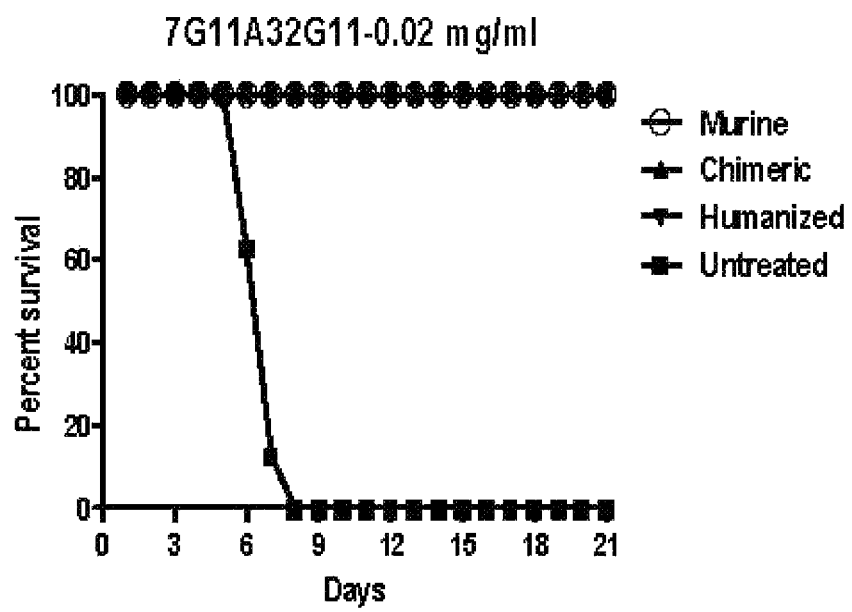
Figure 17C:
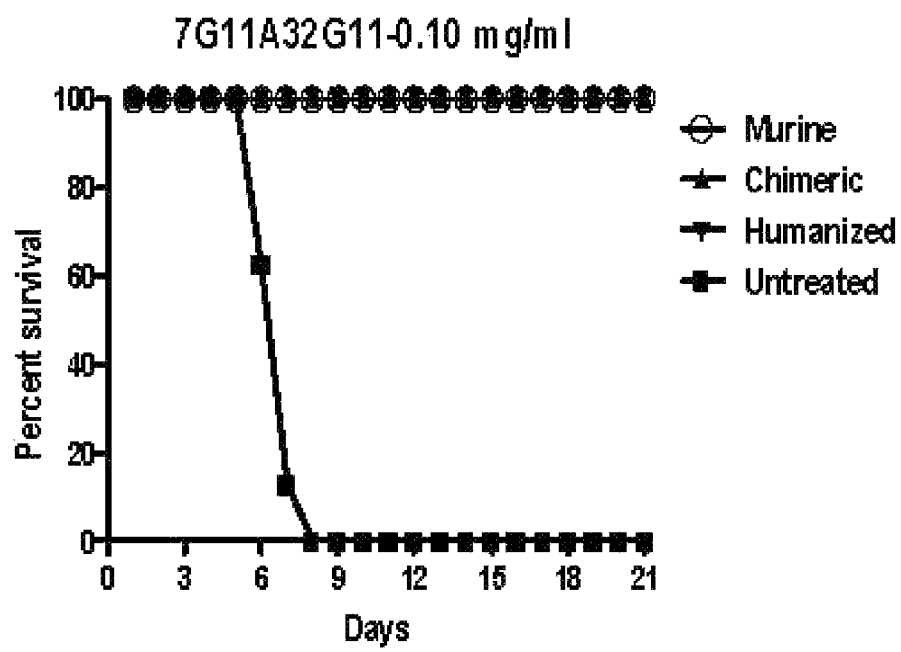
Figure 17D:
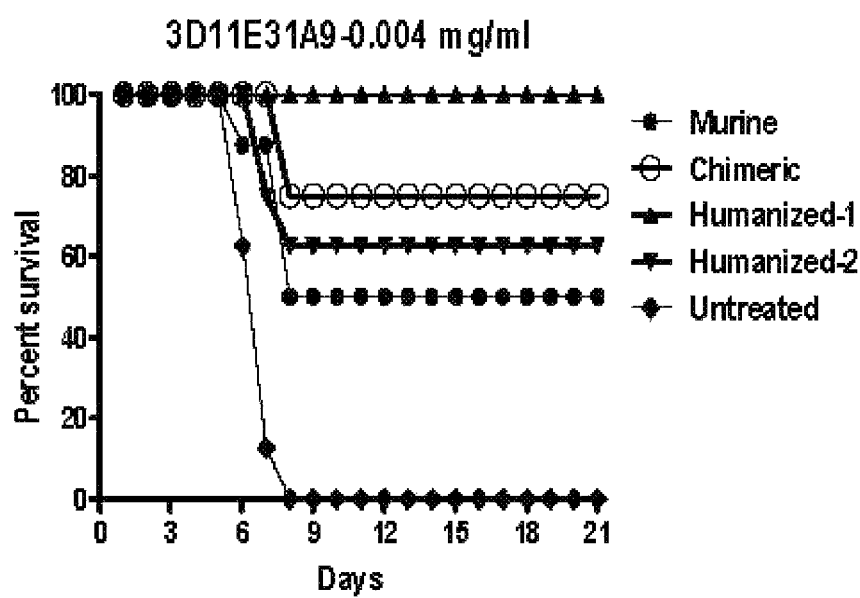
Figure 17E:
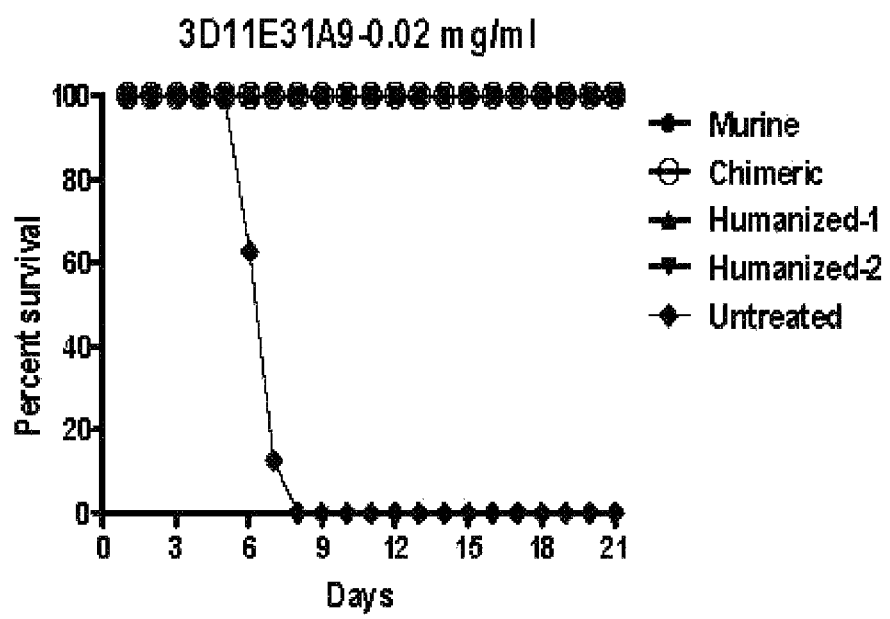
Figure 17F:
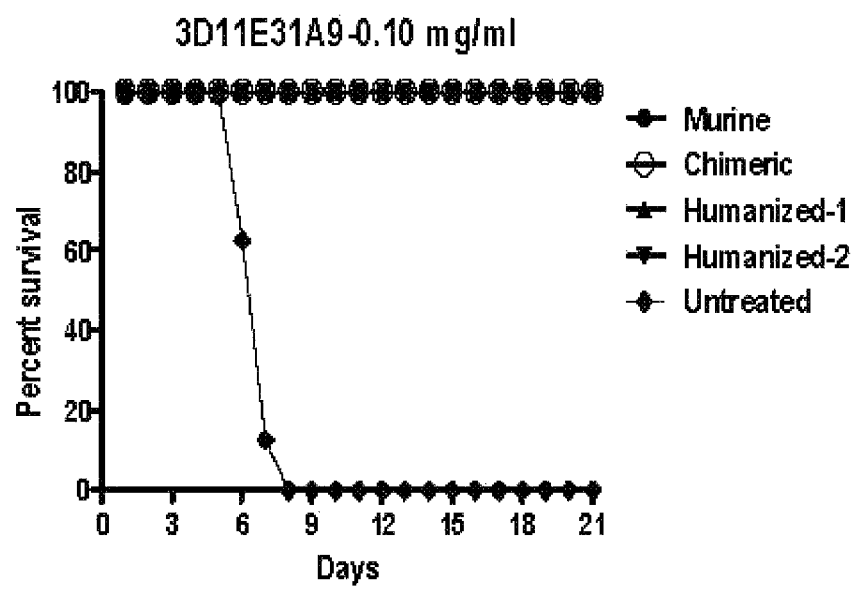

Antigen binding of Ch2G11, Hu2G11-1 and Hu2G11-2 was also examined by ELISA as described below. An ELISA plate was coated with 1 or 2.5 μg/ml of Ch2G11, Hu2G11-1 or Hu2G11-2 in PBS overnight at 4° C. and blocked as described above. After washing with Wash Buffer, 100 μl/well of 1/50, 1/100 or 1/200-diluted Rabipur® in ELISA buffer was added and incubated for 1 hr at room temperature. After washing with Wash Buffer, Rabipur® captured by each test antibody was detected by using 100 μl/well of 1/1,000-diluted HRP-conjugate mouse monoclonal antibody 3D10 supplied by Asia Vision. After incubating for 0.5 hr at room temperature and washing with Wash Buffer, color development was performed as described above. Absorbance was read at 405 nm. The order of the signal from higher to lower was Hu2G11-2, Ch2G11 and Hu2G11-1 (FIG. 14), suggesting that Hu2G11-2 may bind to the antigen better than Hu2G11-1 does.

These results show that anti-rabies antibodies of the present technology specifically bind rabies virus glycoprotein, and that they are useful in methods related to such specific binding, including methods for detecting rabies virus glycoprotein in a sample, or treating or preventing rabies infection in a subject in need thereof and methods for providing post-exposure protection against rabies infection to a subject in need thereof.

Example 13

Binding Activity of Humanized RVNAs

The binding activity of humanized RVNAs to RV glycoprotein was studied in this Example. The humanized RVNA and other biological materials used in the examples are shown in Table 21. Animals used in these studies included BALB/c mice, female, 6~8 weeks, weighing 20 to 30 grams, SPF grade and Syrian hamsters, 2~3 months, weighing 100 grams, SPF grade.

TABLE 21

Bioreagents

| Category | Name | Con. (mg/ml) |
| --- | --- | --- |
| Murine anti-rabies antibody | m-G11 | 2.3 |
| Chimeric anti-rabies antibody | Ch2G11 | 0.5 |
| Humanized anti-rabies antibody | Hu2G11 | 1.0 |
| Murine anti-rabies antibody | m-1A9 | 1.9 |
| Chimeric anti-rabies antibody | Ch1A9 | 1.0 |
| Humanized anti-rabies antibody | Hu1A9-1 | 1.4 |
| Humanized anti-rabies antibody | Hu1A9-2 | 1.8 |
| Murine anti-rabies antibody | RV-3D1 0A6 | 1.2 |
| Enzyme conjugate | 3D10A6-HRP | — |
| Secondary antibody | Mouse anti human IgG 3G2 | 1.35 |
| Secondary antibody | Mouse anti human IgG 3G2-HRP | — |
| Rabies globulin | Human rabies immune globulin | 100 IU/ml |
| Rabies vaccine | Rabies vaccine | — |

The binding of humanized and chimeric RVNAs 2G11 to RV glycoprotein was determined by CLEIA (FIG. 15). The chimeric and humanized versions of 2G11 were used as the capture (FIGS. 15A-C) and detection (FIGS. 15 D-F) antibodies, respectively. RVGP was diluted to 1:50, 1:100, 1:200, 1:400, 1:800 and 1:1600 and then added in the micro-plate. Murine RV 3D10-HRP and mouse anti-human IgG-HRP were used as the enzyme conjugate. RLU (related luminescence unit) represents the chemiluminescence signal. This result indicated that the binding activity of the chimeric Ch2G11 to RVGP was better than that of the humanized.

The binding of the humanized, chimeric and murine RVNAs 1A9 to RVGP was determined by CLEIA (FIG. 16). The chimeric and humanized 1A9 were used as capture (FIGS. 16A-E) and detection (FIGS. 16F-J) antibodies, respectively. RVGP was diluted to 1:50, 1:100, 1:200, 1:400, 1:800 and 1:1600 and then added in the micro-plate. Murine RV 3D10-HRP and mouse anti-human IgG-HRP were used as the enzyme conjugate. RLU (related luminescence unit) represents the chemiluminescence signal. The result showed that binding activity of the chimeric Ch1A9 was superior to that of the humanized.

These results show that anti-rabies antibodies of the present technology specifically bind rabies virus glycoprotein, and that they are useful in methods related to such specific binding, including methods for detecting rabies virus glycoprotein in a sample, or treating or preventing rabies infection in a subject in need thereof and methods for providing post-exposure protection against rabies infection to a subject in need thereof.

Example 14

In Vitro Neutralizing Potency of the Humanized RVNAs

The in vitro neutralizing potency of the RVNAs were measured by rapid fluorescence focus inhibition test (RFFIT) and fluorescent antibody virus neutralization test (FAVN) using CVS-11 rabies virus. The results are shown in Table 22. The results of the two methods were in agreement that the in vitro neutralizing potency level of the humanized 2G11 was lower than that of the murine and the chimeric 2G11, the humanized Hu1A9-1 has the best in vitro neutralizing activity of all the four 1A9 antibodies.

TABLE 22

In vitro neutralizing potency of the humanized RVNAs measured by RFFIT and FAVN

| No. | Name | Neutralization potency (IU/mg) | |
|---|---|---|---|
| | | RFFIT | FAVN |
| 1 | m-G11 | 1667 | 8309 |
| 2 | Ch2G11 | 1261 | 8309 |
| 3 | Hu2G11 | 1261 | 2631 |
| 4 | m-1A9 | 1261 | 308 |
| 5 | Ch1A9 | 1261 | 533 |
| 6 | Hu1A9-1 | 2289 | 2104 |
| 7 | Hu1A9-2 | 1306 | 405 |

To compare the neutralization activity of the humanized 7G11A32G11 or 3D11E31A9 with the murine and the chimeric RVNA, a mouse neutralization test (MNT) was performed. 100 $LD_{50}$/0.03 ml CVS-11 rabies virus was neutralized by the equal volume of the RVNAs at 37° C. for 1 hour and then injected in the brain of the BALB/C mice (n=8 per group). Control group was injected with non-neutralizing virus. The mice were examined daily, and if they showed clinical signs of rabies infection they were euthanized. The BALB/C mice' survival was observed (FIG. 17). All of the control animals died within 9 days, proving that the experiment was effective. There was no difference of the percent survival between the murine and the humanized group when the concentration of the RVNA was higher than 0.02 mg/mL. However, the neutralizing performance of the murine 2G11 was superior to the chimeric and the humanized when the dose decreased to 0.004 mg/mL. Increasing the treatment amounts of the humanized 7G11A32G11 may help improve its neutralizing performance. In addition, the survival rate of the mice that were treated with 0.004 mg/mL humanized Hu1A9-1 or murine m-A19 reached 100% (8/8) and 50% (4/8), respectively.

These results show that anti-rabies antibodies of the present technology neutralize rabies virus infectivity, and that they are useful in methods relating to rabies virus neutralization, including methods for treating or preventing rabies infection in a subject in need thereof, and methods for providing post-exposure protection against rabies virus to a subject in need thereof.

Example 15

Post-Exposure Protection Performance of the Two Humanized RVNAs

Figure 18A:
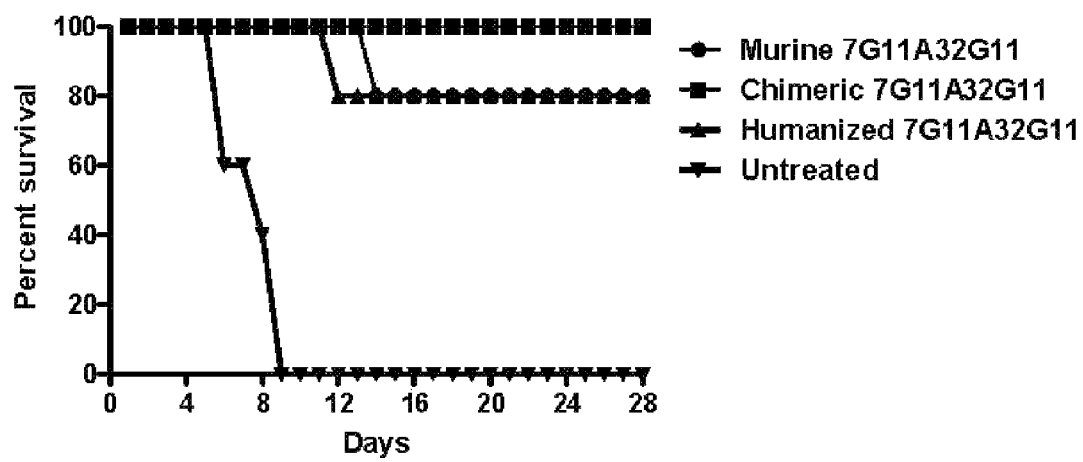
FIGS. 18A-18B are a series of graphs showing the percent survival of Syrian hamsters (n=5 per group) that were challenged with dog street RV (BD06) on day-1. Kaplan-Meier survival curves are shown for days 0 to 28.
Figure 18B:
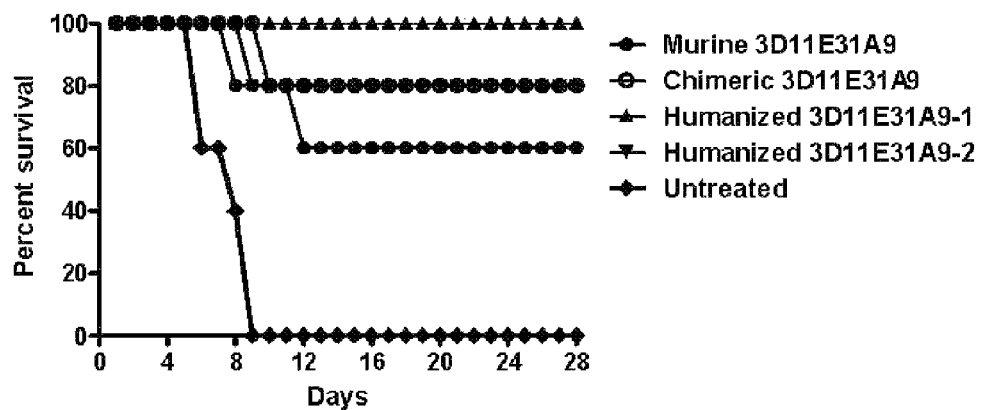

To evaluate the post-exposure protection performance of the humanized 2G11 and 1A9, a Syrian hamster study was performed that the humanized RVNA was compared with the murine and the chimeric RVNA. Hamsters (n=5 per group) were infected with dog street RV (BD06) on day-1. Animals were treated with the equal amounts of murine, chimeric or humanized 2G11 or 1A9 (1 mg/kg) with 16 hour decay, administered at the site of virus inoculation (i.e., right gastrocnemius). The control group was untreated. Hamsters were examined daily, and if they showed clinical signs of rabies infection they were euthanized. The Syrian hamsters' survival was observed (FIG. 18). All of the untreated animals died within 9 days, proving that the experiment was effective. For 2G11, there was no difference of the percent survival between the murine and the humanized group. However, the survival rate of the hamsters that were treated with the humanized 1A9-1 or the murine 1A9 reached 100% (5/5) and 60% (3/5), respectively.

These results show that anti-rabies antibodies of the present technology provide post-exposure protection against rabies infection, and that they are useful in methods relating to such protection, including methods for treating or preventing rabies infection in a subject in need thereof and methods for providing post-exposure protection against rabies virus to a subject in need thereof.

Example 16

Vaccine Immunogenicity in Animals Treated with Hu2G11-1/Hu1A9-2 Cocktail or HRIG To evaluate the post-exposure protection performance of a cocktail of humanized Hu2G11-1/Hu1A9-2, an animal study was performed. Monolayers of neuroblastoma cells were infected with challenge virus standard-11 (CVS-11) or other viruses at a multiplicity of infection (MOI) of 0.3 for 15 min at 37° C./0.5% CO2. The virus inoculum was then removed, fresh medium was added to the cells, and incubation was continued for 40 h at 37° C./0.5% CO2. The culture supernatants were collected and stored at −80° C. until further use. Standard RFFITs for neutralization were performed as described above. To determine the neutralizing potency of each rabies virus neutralizing antibody (RVNA), their 50% neutralizing titers were compared with the 50% neutralizing titer of standard (standard GB), which is defined as 21.4 IU/mL.

Figure 19:
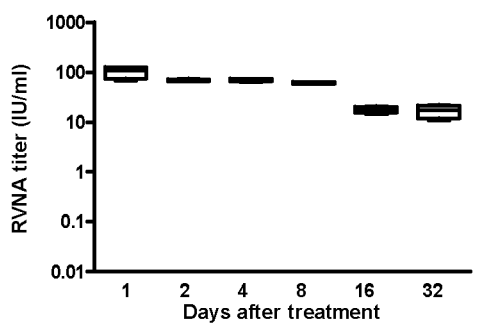
FIG. 19 is a series of graphs showing serum RVNA titers in nonchallenged BALB/c mice. The mice in each treatment group (n=8 per group) were vaccinated with rabies vaccine and treated with (1) 5000 IU/kg Hu2G11-1/Hu1A9-2 cocktail, (2) 1000 IU/kg Hu2G11-1/Hu1A9-2 cocktail, (3) 200 IU/kg Hu2G11-1/Hu1A9-2 cocktail, or (4) 20 IU/kg human rabies immune globulin (BRIG) on day 0, the mice in the control group (5) only received vaccine, and the mice only received PBS was the negative control (6).
Figure 19:
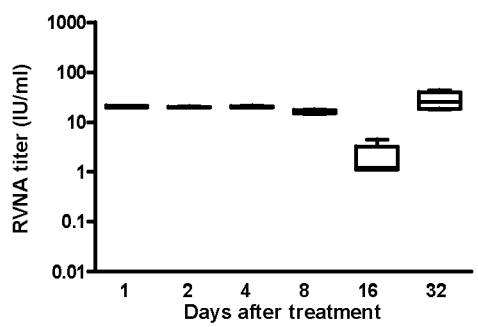
Figure 19:
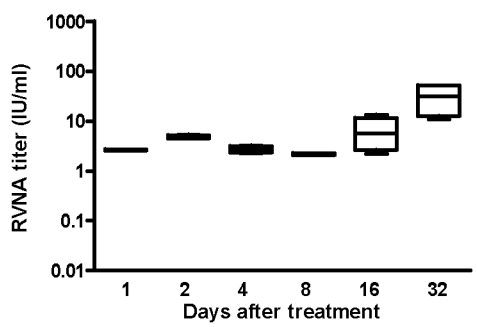
Figure 19:
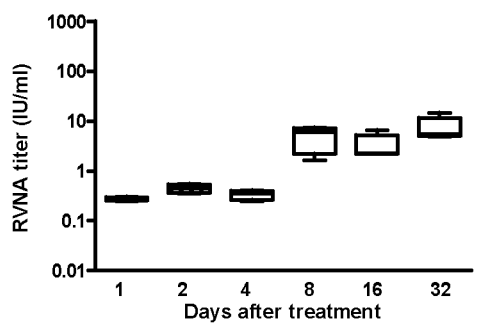
Figure 19:
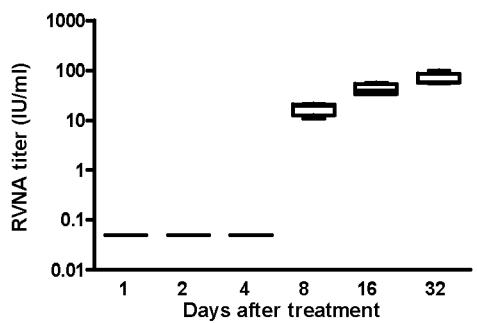
Figure 19:
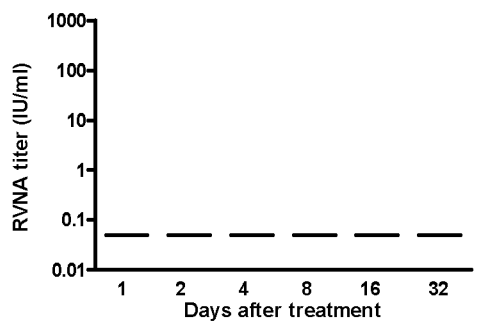

During post-exposure prophylaxis (PEP), there is the possibility that the simultaneous administration of RVNAs and vaccine decreases the ability of the vaccine to induce the threshold levels of neutralization antibodies required for protection. Therefore, it is critical to evaluate the degree of the interference of the Hu2G11-1/Hu1A9-2 cocktail treatment to vaccination. To determine the effect of the Hu2G11-1/Hu1A9-2 cocktail on vaccine potency, an in vivo animal experiment was performed in the absence of RV (FIG. 19). For PEP, BALB/c mice were administered three doses of Hu2G11-1/Hu1A9-2 cocktail plus vaccine or 20 IU/kg BRIG plus vaccine. The three doses of Hu2G11-1/Hu1A9-2 cocktail were 5000 IU/kg, 1000 IU/kg or 200 IU/kg, respectively. The mice which were only administered vaccine were used as control. There were 8 mice in each experimental group. Also, 6 mice which were only administered PBS were used as negative control. On days 1, 2, 4, 8, 16 and 32, blood was collected from mice orbit. 8 mice sera were mixed to 4 sera in each experiment group and then determined the serum RVNA titer. On day 1, day 2 and day 4, serum RVNA titers were high in mice that received Hu2G11-1/Hu1A9-2 cocktail, were lower in mice that received 20 IU/kg HRIG (only 2 sera can meet the requirement of WHO, 0.5 IU/mL) and could not be detected in mice that only vaccinated. RVNA titer in mice that received Hu2G11-1/Hu1A9-2 cocktail remained high level during 8-32 days, higher than or equivalent with the RVNA titer in mice that received HRIG. This result indicated that Hu2G11-1/Hu1A9-2 cocktail did not interfere with the vaccine to induce neutralization antibody. In addition, RVNA titer in mice that received Hu2G11-1/Hu1A9-2 cocktail showed an obvious dose dependent effect during 8-32 days: the higher the dose of the received Hu2G11-1/Hu1A9-2 cocktail, the higher the RVNA titer induced in the mice.

These results show that anti-rabies antibodies of the present technology provide post-exposure protection against rabies infection, and that they are useful in methods relating to such protection, including methods for treating or preventing rabies infection in a subject in need thereof and methods for providing post-exposure protection against rabies virus to a subject in need thereof.

Example 17

Figure 20:
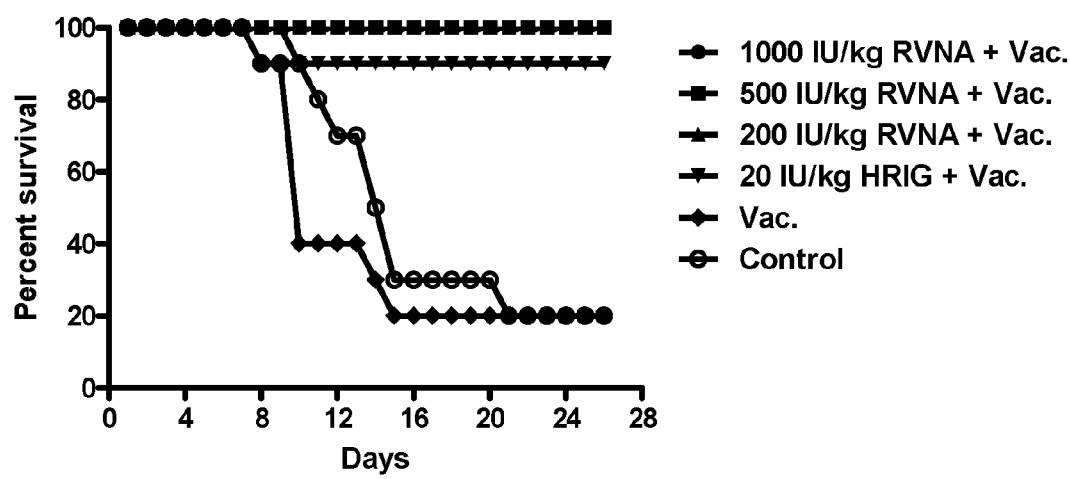
FIG. 20 is a graph showing a comparison between an RVNA cocktail and BRIG with vaccine in Syrian hamsters.

In Vivo Neutralizing Performance of Hu2G11-1/Hu1A9-2 Cocktail Compared with Polyclonal HRIG These To evaluate the in vivo neutralizing performance of the Hu2G11-1/Hu1A9-2 cocktail, a Syrian hamster study was performed. Hamsters (n=10 per group) were infected with dog street RV (BD06). Animals were vaccinated with rabies vaccine (Rabipur, Chiron Behring) on day 0 and then treated with 1000, 500, 200 IU/kg Hu2G11-1/Hu1A9-2 cocktail or 20 IU/kg human rabies immune globulin (*Shuanglin Pharmaceutical*) with 24 hour decay, administered at the site of virus inoculation (i.e., right gastrocneimus). Additional doses of vaccine were administered in the left gastrocneimus muscle on days 3, 7, 14, and 28. Control groups received vaccine alone or untreated. Hamsters were examined daily, and if they showed clinical signs of rabies infection they were euthanized. The Syrian hamsters' survival was observed (FIG. 20). The negative control group had a survival rate of 20%, proving that the experiment was effective. With 24 hour decay, the closed survival rates can be observed that treatment of hamsters with vaccine and Hu2G11-1/Hu1A9-2 cocktail resulted in the survival rate of 100% (10/10) and the survival rate of the hamsters that were treated with vaccine and BRIG was 90% (9/10). This result illustrated that the in vivo neutralizing potency of the Hu2G11-1/Hu1A9-2 cocktail was very strong.

These results show that a combination of anti-rabies antibodies of the present technology neutralize rabies virus infectivity, and that they are useful in methods relating to rabies virus neutralization, including methods for treating or preventing rabies infection in a subject in need thereof and methods for providing post-exposure protection against rabies infection to a subject in need thereof.

Example 18

Post-Exposure Protection Performance of the Two Humanized RVNAs in Human Subjects This example will demonstrate the post-exposure protection performance of the humanized 2G11 and 1A9 in human subjects exposed to rabies virus. Humans exposed to or suspected of being exposed to rabies virus are administered chimeric or humanized 2G11 or 1A9 (1 mg/kg) with 16 hour decay, administered at the site of virus inoculation (i.e., the site of an animal bite). It is expected that treated subjects will display a 100% survival rate, will display fewer or no clinical symptoms of rabies than untreated subjects, and will display a faster and more complete recovery from the rabies exposure than untreated subjects.

These results will show that anti-rabies antibodies of the present technology provide post-exposure protection against rabies infection in humans, and that they are useful in methods relating to such protection, including methods for treating or preventing rabies infection in a subject in need thereof and methods for providing post-exposure protection against rabies virus to a subject in need thereof.

Example 19

In Vivo Neutralizing Performance of Hu2G11-1/Hu1A9-2 Cocktail Compared with Polyclonal HRIG This example will demonstrate the in vivo neutralizing performance of the Hu2G11-1/Hu1A9-2 cocktail in human subjects exposed to rabies virus. Humans exposed to or suspected of being exposed to rabies virus are administered 1000, 500, 200 IU/kg Hu2G11-1/Hu1A9-2 cocktail with 24 hour decay, administered at the site of virus inoculation (i.e., the site of an animal bite). It is expected that treated subjects will display a 100% survival rate, will display fewer or no clinical symptoms of rabies than untreated subjects, and will display a faster and more complete recovery from the rabies exposure than untreated subjects.

These results will show that a combination of anti-rabies antibodies of the present technology neutralize rabies virus infectivity, and that they are useful in methods relating to rabies virus neutralization, including methods for treating or preventing rabies infection in a subject in need thereof and methods for providing post-exposure protection against rabies infection to a subject in need thereof.

EQUIVALENTS

The present technology is not to be limited in terms of the particular embodiments described in this application, which are intended as single illustrations of individual aspects of the present technology. Many modifications and variations of this technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this technology is not limited to particular methods, reagents, compounds compositions or biological systems, which can, of course, vary. It is also to be understood that the terminology used herein is for the purpose of describing particular embodiments only, and is not intended to be limiting. Other embodiments are set forth within the following claims.

All references cited herein are incorporated herein by reference in their entireties and for all purposes to the same extent as if each individual publication, patent, or patent application was specifically and individually incorporated by reference in its entirety for all purposes.

What is claimed is:

1. An isolated antibody that binds to rabies virus glycoprotein wherein:

a. the antibody comprises heavy chain CDR sequences: DYIML (SEQ ID NO:56), DIYPYYGSTSYNLKFKG (SEQ ID NO:57), and QGGDGNYVLFDY (SEQ ID NO:58), corresponding to CDR1, CDR2, and CDR3, respectively, and comprises light chain CDR sequences: KASQNVGTTVA (SEQ ID NO:62), SASYRYS (SEQ ID NO:63), and QQYNSYPFT (SEQ ID NO:64), corresponding to CDR1, CDR2, and CDR3, respectively; or b. the antibody comprises heavy chain CDR sequences: GFAMS (SEQ ID NO:59), TISSGGTYTYSPDSVMG (SEQ ID NO:60), and RLRRNYYSMDY (SEQ ID NO:61), corresponding to CDR1, CDR2, and CDR3, respectively, and comprises light chain CDR sequences: KSTKSLLNSDGFTYLD (SEQ ID NO:65), LVSNRFS (SEQ ID NO:66), and FQSNYLPFT (SEQ ID NO:67), corresponding to CDR1, CDR2, and CDR3, respectively.

2. The isolated antibody of claim 1, wherein the antibody is capable of reducing the infectivity of rabies virus and does not interfere with the immunogenicity of a rabies vaccine.

3. The isolated antibody of claim 1, wherein the antibody is selected from a group consisting of a monoclonal antibody, a murine antibody, a chimeric antibody, and a humanized antibody.

4. A pharmaceutical composition comprising the antibody of claim 1 and a pharmaceutically acceptable carrier.

5. The pharmaceutical composition of claim 4 comprising a cocktail of antibodies wherein a first antibody comprises heavy chain CDR sequences: DYIML (SEQ ID NO:56), DIYPYYGSTSYNLKFKG (SEQ ID NO:57), and QGGDGNYVLFDY (SEQ ID NO:58), corresponding to CDR1, CDR2, and CDR3, respectively, and comprises light chain CDR sequences: KASQNVGTTVA (SEQ ID NO:62), SASYRYS (SEQ ID NO:63), corresponding to CDR1, CDR2, and CDR3, respectively, and QQYNSYPFT (SEQ ID NO:64); and wherein a second antibody comprises heavy chain CDR sequences: GFAMS (SEQ ID NO:59), TISSGGTYTYSPDSVMG (SEQ ID NO:60), and RLRRNYYSMDY (SEQ ID NO:61), corresponding to CDR1, CDR2, and CDR3, respectively, and comprises light chain CDR sequences: KSTKSLLNSDGFTYLD (SEQ ID NO:65), LVSNRFS (SEQ ID NO:66), and FQSNYLPFT (SEQ ID NO:67), corresponding to CDR1, CDR2, and CDR3, respectively.

6. A method for treating rabies infection in a subject in need thereof comprising administering to the subject an effective amount of the antibody of claim 1.

7. The method of claim 6, wherein the antibody is selected from a group consisting of a monoclonal antibody, a murine antibody, a chimeric antibody, and a humanized antibody.

8. The method of claim 6, wherein the antibody is administered to the subject before, after, or simultaneously with a rabies vaccine.

9. The method of claim 6, wherein the antibody is administered to the subject before, after, or simultaneously with an anti-rabies immunoglobulin.

10. A kit for treating or detecting rabies virus in a sample comprising the antibody of claim 1 and instructions for use.

11. The kit of claim 10, wherein the antibody is coupled to one or more detectable labels.

12. The kit of claim 10, further comprising a secondary antibody that binds specifically to the rabies virus glycoprotein antibody.

13. An isolated nucleic acid encoding the antibody of claim 1.

14. A host cell comprising the isolated nucleic acid of claim 13.

* * * * *